US009120858B2

(12) United States Patent
Quadros et al.

(10) Patent No.: US 9,120,858 B2
(45) Date of Patent: Sep. 1, 2015

(54) ANTIBODIES TO THE B12-TRANSCOBALAMIN RECEPTOR

(75) Inventors: Edward V. Quadros, Brooklyn, NY (US); Jeffrey M. Sequeira, Brooklyn, NY (US)

(73) Assignee: The Research Foundation of State University of New York, New York, NY (US)

( * ) Notice: Subject to any disclaimer, the term of this patent is extended or adjusted under 35 U.S.C. 154(b) by 0 days.

(21) Appl. No.: 13/554,780

(22) Filed: Jul. 20, 2012

(65) Prior Publication Data

US 2013/0164309 A1 Jun. 27, 2013

Related U.S. Application Data

(60) Provisional application No. 61/510,889, filed on Jul. 22, 2011, provisional application No. 61/536,361, filed on Sep. 19, 2011.

(51) Int. Cl.
*C07K 16/28* (2006.01)
*C07K 16/30* (2006.01)
*A61K 47/48* (2006.01)
*G01N 33/82* (2006.01)

(52) U.S. Cl.
CPC ........... *C07K 16/30* (2013.01); *A61K 47/48569* (2013.01); *C07K 16/2896* (2013.01); *G01N 33/82* (2013.01); *C07K 2317/34* (2013.01); *C07K 2317/73* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 4,167,556 A | 9/1979 | Selhub et al. |
| 4,237,224 A | 12/1980 | Cohen et al. |
| 4,429,008 A | 1/1984 | Martin et al. |
| 4,485,045 A | 11/1984 | Regen |
| 4,489,710 A | 12/1984 | Spitler |
| 4,507,234 A | 3/1985 | Kato et al. |
| 4,544,545 A | 10/1985 | Ryan et al. |
| 4,569,789 A | 2/1986 | Blattler et al. |
| 4,625,014 A | 11/1986 | Senter et al. |
| 4,671,958 A | 6/1987 | Rodwell et al. |
| 4,673,562 A | 6/1987 | Davison et al. |
| 4,699,784 A | 10/1987 | Shih et al. |
| 4,735,792 A | 4/1988 | Srivastava |
| 4,751,180 A | 6/1988 | Cousens et al. |
| 4,816,567 A | 3/1989 | Cabilly et al. |
| 4,873,088 A | 10/1989 | Mayhew et al. |
| 4,935,233 A | 6/1990 | Bell et al. |
| 5,013,556 A | 5/1991 | Woodle et al. |
| 5,151,510 A | 9/1992 | Stec et al. |
| 5,196,510 A | 3/1993 | Rodwell et al. |
| 5,208,020 A | 5/1993 | Chari et al. |
| 5,229,275 A | 7/1993 | Goroff |
| 5,294,536 A | 3/1994 | Palumbo |
| 5,310,656 A | 5/1994 | Pourfarzneh et al. |
| 5,428,023 A | 6/1995 | Russell-Jones et al. |
| 5,530,101 A | 6/1996 | Queen et al. |
| 5,538,901 A | 7/1996 | Law et al. |
| 5,545,806 A | 8/1996 | Lonberg et al. |
| 5,545,807 A | 8/1996 | Surani et al. |
| 5,548,064 A | 8/1996 | Russell-Jones et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,574,018 A | 11/1996 | Habberfield et al. |
| 5,587,458 A | 12/1996 | King et al. |
| 5,589,369 A | 12/1996 | Seidman et al. |
| 5,589,463 A | 12/1996 | Russell-Jones et al. |
| 5,591,317 A | 1/1997 | Pitts, Jr. |
| 5,591,669 A | 1/1997 | Krimpenfort et al. |
| 5,641,870 A | 6/1997 | Rinderknect et al. |
| 5,688,504 A | 11/1997 | Morgan, Jr. |
| 5,739,277 A | 4/1998 | Presta et al. |
| 5,739,287 A | 4/1998 | Wilbur et al. |
| 5,739,313 A | 4/1998 | Collins et al. |
| 5,747,470 A | 5/1998 | Becherer et al. |
| 5,770,429 A | 6/1998 | Lonberg et al. |
| 5,783,683 A | 7/1998 | Morrison |
| 5,821,337 A | 10/1998 | Carter et al. |
| 5,833,985 A | 11/1998 | Ball et al. |
| 5,837,243 A | 11/1998 | Deo et al. |
| 5,837,458 A | 11/1998 | Minshull et al. |
| 5,840,712 A | 11/1998 | Morgan, Jr. et al. |
| 5,840,880 A | 11/1998 | Morgan, Jr. et al. |

(Continued)

FOREIGN PATENT DOCUMENTS

EP 0 069 450 1/1983
EP 0 361 817 4/1990

(Continued)

OTHER PUBLICATIONS

Jiang et al. Characterizing monoclonal antibodies to antigenic domains of TCblR/CD320, the receptor for cellular uptake of transcobalamin-bound cobalamin. Drug Delivery. Published online Sep. 20, 2010; Jan.; 18(1):74-8.*
Quadros et al. Targeted Delivery of Saporin Toxin by Monoclonal Antibody to the Transcobalamin Receptor, TCblR/CD320. Molecular Cancer Therapeutics. Published online Sep. 21, 2010; 9(11): 3033-3040.*
Vajdos et al. Comprehensive Functional Maps of the Antigen binding Site of an Anti-ErbB2 Antibody Obtained with Shotgun Scanning Mutagenesis. Journal of Molecular Biology. Jul. 5, 2002; 320(2):415-28.*
Rudikoff et al. Single amino acid substitution altering antigen-binding specificity. Proceeding of the National Academy of Sciences. Mar. 1982; 79(6):1979-1983.*

(Continued)

*Primary Examiner* — Vanessa L. Ford
*Assistant Examiner* — Sandra Dillahunt
(74) *Attorney, Agent, or Firm* — Cooley LLP

(57) ABSTRACT

The present invention provides anti-TCblR antibodies and related compositions, which may be used in any of a variety of therapeutic methods for the treatment of cancer, tumors and other proliferative diseases and disorders.

17 Claims, 37 Drawing Sheets

(56) References Cited

U.S. PATENT DOCUMENTS

| | | | |
|---|---|---|---|
| 5,869,046 | A | 2/1999 | Presta et al. |
| 5,869,465 | A | 2/1999 | Morgan, Jr. et al. |
| 5,922,845 | A | 7/1999 | Deo et al. |
| 6,004,533 | A | 12/1999 | Collins et al. |
| 6,071,517 | A | 6/2000 | Fanger et al. |
| 6,083,926 | A | 7/2000 | Morgan, Jr. et al. |
| 6,096,290 | A | 8/2000 | Collins et al. |
| 6,096,311 | A | 8/2000 | Fanger et al. |
| 6,111,166 | A | 8/2000 | Van de Winkel |
| 6,211,355 | B1 | 4/2001 | Collins et al. |
| 6,270,765 | B1 | 8/2001 | Deo et al. |
| 6,303,755 | B1 | 10/2001 | Deo et al. |
| 6,365,116 | B1 | 4/2002 | Barham et al. |
| 6,410,690 | B1 | 6/2002 | Deo et al. |
| 6,596,541 | B2 | 7/2003 | Murphy et al. |
| 6,613,305 | B1 | 9/2003 | Collins et al. |
| 6,682,928 | B2 | 1/2004 | Keler et al. |
| 6,696,248 | B1 | 2/2004 | Knappik et al. |
| 6,706,484 | B1 | 3/2004 | Knappik et al. |
| 6,753,138 | B1 | 6/2004 | Schneider et al. |
| 6,806,363 | B1 | 10/2004 | Collins et al. |
| 6,824,780 | B1 | 11/2004 | Devaux et al. |
| 6,828,422 | B1 | 12/2004 | Achim et al. |
| 6,838,073 | B1 | 1/2005 | Collins et al. |
| 6,984,720 | B1 | 1/2006 | Korman et al. |
| 7,049,135 | B2 | 5/2006 | Rudert et al. |
| 7,049,426 | B2 | 5/2006 | Green et al. |
| 7,141,233 | B2 | 11/2006 | Collins et al. |
| 7,179,445 | B2 | 2/2007 | Collins et al. |
| 7,256,257 | B2 | 8/2007 | Doronina et al. |
| 7,416,728 | B2 | 8/2008 | Morgan, Jr. et al. |
| 7,462,697 | B2 | 12/2008 | Couto et al. |
| 7,498,415 | B2 | 3/2009 | Shitara et al. |
| 7,632,492 | B2 | 12/2009 | Grabstein et al. |
| 7,754,681 | B2 | 7/2010 | Feng |
| 7,837,980 | B2 | 11/2010 | Alley et al. |
| 7,851,437 | B2 | 12/2010 | Senter et al. |
| 7,964,566 | B2 | 6/2011 | Doronina et al. |
| 7,964,567 | B2 | 6/2011 | Doronina et al. |
| 2003/0180312 | A1 | 9/2003 | Ashkenazi et al. |
| 2004/0157291 | A1 | 8/2004 | Frisch et al. |
| 2005/0169910 | A1 | 8/2005 | Morgan, Jr. et al. |
| 2006/0003334 | A1 | 1/2006 | Achim et al. |
| 2006/0121563 | A1 | 6/2006 | Prassler et al. |
| 2010/0061974 | A1 | 3/2010 | Quadros et al. |
| 2010/0239592 | A1 | 9/2010 | Carmel et al. |

FOREIGN PATENT DOCUMENTS

| | | |
|---|---|---|
| EP | 0 404 097 | 6/1990 |
| EP | 0 378 203 | 7/1990 |
| EP | 0 425 235 | 5/1991 |
| EP | 0 425 680 | 5/1991 |
| EP | 0 519 596 | 12/1992 |
| EP | 0 599 325 | 6/1994 |
| JP | 63-3262 | 10/1994 |
| WO | WO 81/02930 | 10/1981 |
| WO | WO 87/02251 | 4/1987 |
| WO | WO 90/10014 | 9/1990 |
| WO | WO 92/01047 | 1/1992 |
| WO | WO 93/11161 | 6/1993 |
| WO | WO 93/16185 | 8/1993 |
| WO | WO 93/23557 | 11/1993 |
| WO | WO 94/27613 | 12/1994 |
| WO | WO 95/27723 | 10/1995 |
| WO | WO 96/08515 | 3/1996 |
| WO | WO 96/16673 | 6/1996 |
| WO | WO 97/14711 | 4/1997 |
| WO | WO 97/17852 | 5/1997 |
| WO | WO 97/38731 | 10/1997 |
| WO | WO 98/02463 | 1/1998 |
| WO | WO 99/32619 | 7/1999 |
| WO | WO 00/37638 | 6/2000 |
| WO | WO 01/29058 | 4/2001 |
| WO | WO 01/68836 | 9/2001 |
| WO | WO 01/75164 | 10/2001 |
| WO | WO 01/92513 | 12/2001 |
| WO | WO 01/96584 | 12/2001 |
| WO | WO 02/44321 | 6/2002 |
| WO | WO 2004/048414 | 6/2004 |
| WO | WO 2007/117657 | 10/2007 |
| WO | WO 2013/015821 | 1/2013 |

OTHER PUBLICATIONS

Brown et al. Tolerance to Single, but not Multiple, Amino Acid Replacements in Antibody VH CDR2. Journal of Immunology. May 1996;156(9):3285-91.*

McLean et al. Antibodies to Transcobalamin II Block in Vitro Proliferation of Leukemic Cells. Blood. 89(1): 235-242, 1997.*

Amagasaki et al., "Expression of Transcobalamin II Receptors by Human Leukemia K562 and HL-60 Cells," *Blood*, 76:1380-1386, 1990.

Andersen et al., "Identification of the Minimal Functional Unit in the Low Density Lipoprotein Receptor-related Protein for Binding the Receptor-associated Protein (RAP)," *J Biol Chem*, 275(28):21017-21024, 2000.

Battaglia-Hsu, et al., "Vitamin B12 deficiency reduces proliferation and promotes differentiation of neuroblastoma cells and up-regulates PP2A, proNGF, and TACE," *Proc. Natl. Acad. Sci.*, 106:21930-21935, 2009.

Begly et al., "Cobalamin metabolism in cultured human chorionic villus cells," *J. Cell Physiol.*, 156:43, 1993.

Bertino, "Cancer research: from folate antagonism to molecular targets," *Best Pract. Res. Clin. Haematol.*, 22:577-582, 2009.

Bieri et al., "Disulfide Bridges of a Cysteine-Rich Repeat of the LDL Receptor Ligand-Binding Domain," *Biochemistry*, 34:13059-13065, 1995.

Bolognesi et al., "CD38 as a target ofiB4 mAb carrying saporin-S6: design of an immunotoxin for ex vivo depletion of hematological CD38+ neoplasia," *J. Biol. Regul. Homeost Agents*, 19:145-152, 2005.

Bose et al., "In Vitro and in Vivo Inactivation of Transcobalamin II Receptor by its Antiserum," *J. Biological Chemistry*, 372(8):4195-4200, 1996.

Bose et al., "Purification, membrane expression, and interactions of transcobalamin II receptor," *Methods Enzymol*, 281:281-289, 1997.

Brown et al., "Calcium cages, acid baths and recycling receptors," *Nature*, 388:629-630, 1997.

Bu, "The Roles of Receptor-Associated Protein (RAP) as a Molecular Chaperone for Members of the LDL Receptor Family," *Int Rev Cytol*, 209:79-116, 2001.

Carmel et al., "Monoclonal antibodies to different sites on human transcobalamin II," *Proc Soc Exp Biol Med*, 188(1):77-81, 1988.

Caplen, N. et al., "Specific inhibition of gene expression by small double-stranded RNAs in invertebrate and vertebrate systems," *Proc. Natl. Acad. Sci.*, 98:9746-9747, 2001.

Cho et al., "Expression of CD320 in human B cells in addition to follicular dendritic cells," *BMB reports*, 41(12):863-867, 2008.

Collins. et al., "Distribution of radiolabeled adenosylcobalamin in patients diagnosed with various malignancies," *Mayo Clin. Proc.*, 75:568-580, 2000.

Cooper et al., "Sequential mechanisms in the enhanced absorption of vitamin B12 by intrinsic factor in the rat." *J Clin Invest.*, 39:199-214, 1960.

Cooper and Paranchych, "Selective Update of Specifically Bound Cobalt-58 Vitamin $B_{12}$ by Human and Mouse Tumour Cells," *Nature*, 191:393-5, 1961.

Cunningham and Wells, "High-Resolution Epitope Mapping of hGH-Receptor Interactions by Alanine-Scanning Mutagenesis," *Science*, 244:1081-1085,1989.

Daniels TR et al., "Conjugation of an anti transferrin receptor IgG3-avidin fusion protein with biotinylated saporin results in significant enhancement of its cytotoxicity against malignant hematopoietic cells." *Mol. Cancer Ther.*, 6:2995-3008: 2007.

Digirolamo and Huennekens, "Transport of vitamin B12 into mouse leukemia cells," *Arch Biochem Biophys*, 168:386-393, 1975.

(56) References Cited

OTHER PUBLICATIONS

Elshabir, S.M. et al., "Functional anatomy of siRNAs for mediating efficient RNAi in Drosophila melanogaster embryo lysate," *EMBO J.*, 20:23, pp. 6877-6888: 2001.
Elshabir et al., "Duplexes of 21-nucleotide RNAs mediate RNA interference in cultured mammalian cells," 411:494-498: 2001.
Epstein et al., "Biological activity of liposome-encapsulated murine interferon Y is mediated by a cell membrane receptor," *Proc. Natl. Acad. Sci*, 82:3688,1985.
Esser et al., "Mutational Analysis of the Ligand Binding Domain of the Low Density Lipoprotein Receptor," *J Biol Chem*, 263:13282-13290, 1988.
International Search Report for PCT/US93/04341, dated Sep. 17, 1993.
Fass et al., "Molecular basis of familial hypercholesterolaemia from structure of LDL receptor module," *Nature*, 388:691-693, 1997.
Frankel AE, et al., "Prospects for Immunotoxin Therapy in Cancer," *Annu. Rev. Med.*, 37:125-42, 1986.
Friedman, et al. "A saturable high affinity binding site for transcobalamin II-vitamin B12 complexes in human placental membrane preparations," *J. Clin. Invest.*, 59:51-58, 1977.
Hall et al., *Cyclic activity of the receptors of cobalamin bound to transcobalamin II. J Cell Physiol.*, 133:187-91, 1987.
Hall "The uptake of vitamin B12 by human lymphocytes and the relationships to the cell cycle," *J. Lab. Clin. Med.*, 103:70-81, 1984.
Hwang et al., "Hepatic uptake and degradation of unilamellar sphingomyelin/cholesterol liposomes: A kinetic study," *Proc. Natl. Acad. Sci. USA*, 77:4030,1980.
International Search Report for PCT/US96/16672, dated Mar. 5, 1997.
International Search Report for PCT/US95/12207, dated Feb. 29, 1996.
International Search Report for PCT/US95/04404, dated Aug. 18, 1995.
International Preliminary Report on Patentability and Written Opinion for PCT/US2007/008674 dated Apr. 16, 2008.
International Search Report for PCT/2007/008674 dated Apr. 16, 2008.
International Search Report for PCT/US2011/052154, dated Apr. 13, 2012.
Ippoliti R et al., "A chimeric saporin-transferrin conjugate compared to ricin toxin: role of the carrier in intracellular transport and toxicity," *Faseb J.*, 9:1220-5, 1995.
Iwahashi et al., "CDR substitutions of a humanized monoclonal antibody (CC49): contributions of individual CDRs to antigen binding and immunogenicity," *Mol Immunol.*, 36(15-16):1079-1091, 1999.
Jiang et al., "Characterization of the promoter region of TCbIR/CD320 gene, the receptor for cellular uptake of transcobalamin-bound cobalamin," *Gene*, 466(1-2):49-55, 2010.
Jiang et al., "Characterizing monoclonal antibodies to antigenic domains of TCbIR/CD320, the receptor for cellular uptake of transcobalamin-bound cobalamin," *Drug Deliv*, 18(1):74-78, 2011.
Kurniawan et al., "NMR structure of a contcatemer of the first and second ligand-binding modules of the human low-density lipoprotein receptor," *Protein Sci*, 9:1282-1293, 2000.
LeFranc et al., "IMGT unique numbering for immunoglobulin and T cell receptor variable domains and Ig superfamily V-like domains," *Developmental and Comparative Immunology*, 27:55-77, 2003.
Li, L. et al., "Novel follicular dendritic cell molecule, 8D6, collaborates with CD44 in supporting lymphomagenesis by a Burkitt lymphoma cell line, L3055," *Blood*, 104:3:815-821, 2004.
Li, L. et al., "Identification of a human follicular dendritic cell molecule that stimulates germinal center B cell growth," *J. Exp. Med.*, 191:1077-1083, 2000.
Lai, Shao-Chiang, et al., "Down-regulation of transcobalamin receptor TCbIR/CD320 by siRNA inhibits cobalamin uptake and proliferation of cells in culture," *Experimental Cell Research*, 317:1603-1607, 2011.

Lindemans et al., "Uptake of transcobalamin II-bound cobalamin by HL-60 cells: effects of differentiation induction." *Exp Cell Res*, 184:449-60, 1989.
Marcoullis et al., "Blocking and Binding Type Antibodies against all Major Vitamin B12-Binders in a Pernicious Anaemia Serum," *British Journal of Haematology*, 43:15-26, 1979.
McGuire, "Anticancer antifolates: current status and future directions," *Curr. Pharm. Des.*, 9:2593-2613, 2003.
McLean et al, "Antibodies to transcobalamin II block in vitro proliferation of leukemic cells," *Blood*,89: 235-242, 1997.
Oldham RK., "Monoclonal antibodies in cancer therapy" *J. Clin. Oncol.*, 1:582-90,1983.
Paranchych W, et al., "Factors influencing the uptake of cyanocobalamin (vitamin B12) by Ehrlich ascites carcinoma cells." *Biochim. Biophys. Acta.*, 60:393-403, 1962.
Platica et al., "The cDNA sequence and the deduced amino acid sequence of human transcobalamin II show homology with rat intrinsic factor and human transcobalamin I," *J Biol Chem*, 266(12):7860-7863, 1991.
Pluckthun, "Antibody Engineering: Advances From the Use of *Escherichia Coli* Expression Systems," *Bio/Technology*, 9: 545-551, 1991.
Polito L, et al., "The conjugate Rituximab/saporin-S6 completely inhibits clonogenic growth of CD20- expressing cells and produces a synergistic toxic effect with Fludarabine" *Leukemia*,18:1215-1222, 2004.
Product Data Sheet: Anti human CD320/TCbIR/8D6A Antibody, R&D Systems, 2009.
Qian ZM, et al., "Targeted drug delivery via the transferrin receptor—mediated endocytosis pathway," *Pharmacol. Rev.*, 54:561-587: 2002.
Quadros et al., "Characterization of the human placental membrane receptor for transcobalamin II-cobalamin," *Arch Biochem Biophys.*, 308:192-199, 1994.
Quadros et al., "Epitope Specific Monoclonal Antibodies (mAbs) to Human Transcobalamin II (TCII) can Induce Apoptosis by Inhibiting the Cellular Uptake of Cabalamin (Cbl)," *Blood*, 86(10 Suppl. 1): 125A, 1995.
Quadros and Jacobsen, "The dynamics of cobalamin utilization in L-1210 mouse leukemia cells: a model of cellular cobalamin metabolism," *Biochim Biophys Acta*, 1244:395-403, 1995.
Quadros et al., "Transcobalamin II synthesized in the intestinal villi facilitates transfer of cobalamin to the portal blood," *Am J Physiol*, 277:G161-6, 1999.
Quadros et al., "The binding properties of the human receptor for the cellular uptake of vitamin Bl2," Biochem.*Biochem Biophys Res Commun*, 327:1006-10, 2005.
Quadros et al., "The protein and the gene encoding the receptor for the cellular uptake of transcobalamin-bound cobalamin," *Blood*, 113:186-192, 2009.
Quadros et al., "Functional human transcobalamin II isoproteins are secreted by insect cells using the baculovirus expression system," *Blood*, 81, 1239-45, 1993.
Quadros, et al., "Characterization of monoclonal antibodies to epitopes of human transcobalamin II," Biochem. *Biophys. Res. Commun.*, 222:149-154, 1996.
Quadros, et al., "Advances in the understanding of cobalamin assimilation and metabolism," *Br. J. Haematol.*,148:195-204, 2010.
Quadros et al., "Positive Newborn Screen for Methylmalonic Aciduria Identifies the First Mutation in TCbIR/CD320, the Gene for Cellular Uptake of Transcobalamin-bound Vitamin $B_{12}$,"*Hum Mutat*, 31:924-929, 2010.
Quadros, et al., "Targeted delivery of saporin toxin by monoclonal antibody to the transcobalamin receptor, TCbIR/CD320," Mol. Cancer Ther., 11:3033-3040, 2010.
Russell-Jones et al., "Vitamin-mediated targeting as a potential mechanism to increase drug uptake by tumors," *J. Inorg. Biochem.*, 98:1625-1633: 2004.
Schier et al., "Isolation of Picomolar Affinity Anti-c-erbB-2 Single-chain Fv by Molecular Evolution of the Complementarity Determining Regions in the Center of the Antibody Binding Site," *J. Mol. Biol.*, 263:551-567, 1996.

(56) References Cited

OTHER PUBLICATIONS

Schueler-Furman et al., "Progress in Modeling of Protein Structures and Interactions," *Science*, 310:638, 2005.

Seligman, et al "Characterization of the receptor for transcobalamin Ii isolated from human placenta," *J. Biol. Chem.*, 253:6:1766-1772, 1978.

Stirpe et al., Ribosome-inactivating proteins from the seeds of Saponaria officinalis L. (soapwort), of Agrostemma githago L. (corn cockle) and of Asparagus officinalis L. (asparagus, and from the latex of Hura crepitans L. (sandbox tree) Biochem J, 216:617-25, 1983.

Takahashi K, et al., "Receptor binding and internalization of immobilized transcobalamin II by mouse leukaemia cells," *Nature*, 288:713-715, 1980.

Taylor and Hanna, "Folate-Dependent Enzymbes in Cultured Chinese Hamster Ovary Cells: Induction of 5- Methyltetrahydrofolate Homocysteine Cobalamin Methyltransferase by Folate and Methiionine," *Arch Biochem Biophys*, 171:507-20, 1975.

Ullelend et al., "Direct assay for cobalamin bound to transcobalamin (Holotranscobalamin) in serum," *Serum Clinical Chemistry*, 48(3):526-532, 2002.

Van Driel et al., "First Cysteine-rich Repeat in Ligand-binding Domain of Low Density Lipoprotein Receptor Binds $Ca^{2+}$ and Monoclonal Antibodies, but not Lipoproteins," *J Biol Chem*, 262:17443-17449, 1987.

Walker PR, et al., "Induction of apoptosis in neoplastic cells by depletion of vitamin B12," *Cell Death Differ.*, 4:233-241, 1997.

White et al., "Combinations of anti-transferrin receptor monoclonal antibodies inhibit human tumor cell growth in vitro and in vivo: evidence for synergistic antiproliferative effects," *Cancer Research*, 50(19):6295-6301, 1990.

Wickramasinghe, "Morphology, biology and biochemistry of cobalamin- and folatedeficient bone marrow cells,"Baillieres Clin Haematol, 8:441-59, 1995.

Youngdahl-Turner et al., "Protein Mediated Vitamin Updtake," *Exp Cell Res*, 118:127-34, 1979.

Zhang, X. et al., "The distinct roles of T cell-derived cytokines and a novel follicular dendritic cell-signaling molecule 8D6 in germinal center-B cell differentiation," *J. Immunol.*, 167:49-56, 2001.

GenBank Accession No. BC000668, published Jul. 15, 2006.
GenBank Accession No. BC007083, published Jul. 15, 2006.
GenBank Accession No. CAG33455, published Oct. 16, 2008.
GenBank Accession No. AAH00668, published Jul. 15, 2006.
GenBank Accession No. CR457174, published Oct. 16, 2008.
GenBank Accession No. NM_016579, published Oct. 22, 2011.
GenBank Accession No. AAH07083, published Jul. 15, 2006.
GenBank Accession No. NT_077812, published Jul. 29, 2011.
GenBank Accession No. NT 086894, published Aug. 20, 2004.
GenBank Accession No. NP_057663, published Oct. 22, 2011.
GenBank Gene ID: 51293, updated May 11, 2012.

\* cited by examiner

ATGAGAGTGCTGATTCCTTGTGGCTGTGTTCACAGCCTTTCCTGGTATCCTGTCTGATGTGCAGCTTCAGGAGT
CGGGACCCTGGCCTGGTGAAACCTTCTCAGTCTCTGTCCCCTCACCTGCACTGTCCTTGGCTATTCAATCACCAG
TGATTATGCCTGGAACTGGATCCGGCAGTTTCCAGGAAACAAACTGGAGTGGATGGGCTACATAAGCTTTAGT
GGTAACATTCGTTACAACCCGTCTCTCGAGTCGAATCTCTATCACTCGAGACACATCCAAGAGCCAGTTCT
TCCTGCAGTTGAATTCTGTGACTACTGAGGACACAGAGGCACACATATTACTGTGCAAGAGCGGGACTGGGACGAGT
GTTCTACTTTGACTACTGGGGCCAAGGCACCGCTCTCACAGTCTCCTCA (SEQ ID NO:1)

*FIG. 10A*

MRVLIPLWLFTAFPGILSDVQLQESGPGLVKPSQSLSLTCTVLGYSITSDYAWNWIRQFPGNKLEWMGYISFS
GNIRYNPSLESRISITRDTSKSQFFLQLNSVTTEDRGTYYCARAGLGRVFYFDYWGQGTALTVSS (SEQ ID
NO:5)

*FIG. 10B*

ATGGATTCACAGGCCCAGGTTCTCTTATGTTACTGCTGCTATGCTGGTACCTGTGTGGGACATTGTGATGT
CACAGTCTCCATCCTCCCTAGCTGTGTCTGTTGGAGAGAAGGTTACTATGAGCTGCAAGTCCAGTCAGAGCCT
TTTATATAGTAGCAATCAAAAGAACTACTTGGCCTGGTACCAGCAGAAACCAGGGCAGTCTCCTAAACTGTTG
ATTTTCCGGGCATCCACCAGGGAATCTGGGGTCCCTGATCGCTTCACAGGCAGTGGATCTGGGACAGATTCA
CTCTCACCATCAGCAGTGTGAAGGCCTGAAGACCTGGCCAGTTTATTTCTGTCAGCAATATTATAACTATCCATT
CACGTTCGGCTCGGGGACAAACGTTGGAGATAAAA (SEQ ID NO:9)

*FIG. 11A*

MDSQAQVLMLLLWVSGTCGDIVMSQSPSSLAVSVGEKVTMSCKSSQSLLYSSNQKNYLAWYQQKPGQSPQLL
IFRASTRESGVPDRFTGSGSGTDFTLTISSVKPEDLAVYFCQQYYNYPFTFGSGTTLEIK (SEQ ID NO:13)

*FIG. 11B*

ATGAGAGTGCTGATTCTTTTGTGGCTGTTCAAAGCCCTTCCTGGTATCCTGTCTGATGTGCAGCTTCAGGAGT
CGGGACCTGGCCTGGTGAAACCTTCTCAGTCTCTGTCCCTCACCTGCACTGTCACT**GGCTACTCAATCACCAG
TGATTATGCCTGGAACTGGATCCGGCAGTTCCCTGGAAACAAACTGGAGTGGATGGGCTACATAGCCTACACT
AATAGGACT**TTCTACACCCCATCTCTCGAAAGTCGAATCTCTATCACTCGGGACACATCCAAGAACCAGTTCT
TCCTGCAGTTGAATTCTGTGAGGACTGAGGACACAGGCACATATTACTGT**GCACGAAAACTCCGGTAAAACCTA
CGGCTTTACTTAC**TGGGGCCAAGGGACTCTAGTCACTGTCTCTGCA (SEQ ID NO:17)

*FIG. 12A*

MRVLILLWLFKAFPGILSDVQLQESGPGLVKPSQSLSLTCTVTGYSITSDYAWNWIRQFPGNKLEWMGY**IAYT
NRTFYTPSLESRISITRDTSKNQFFLQLNSVTTEDTGTYYCARNSGKTYGFTY**WGQGTLVTVSA (SEQ ID
NO:21)

*FIG. 12B*

ATGGATTCACAGGCCCAGGTTCTTATGTTACTGCTGCTAGTGTTACTGTGGGTATCTGGTACCTGTGTGGGGACATTGTGATGT
CACAGTCTCCATCCCCCTAGTTGTGTCAGTTGGAGAGAAGGTTACTATGAGCTGCAAGTCCAGTCAGGCGGCT
TTTATATAGTGCCAATCAAAAGAACTACTTGGCCTGGTACCAGCAGAAACCAGGGCAGTCTCCTAAACTGCTG
ATTTACTGGGCATCCACTAGGGAATCTGGGGTCCCTGATCGCTTCACAGGCAGTGGATCTGGGACAGATTTCA
CTCTCACCATCAGCAGTGTGAGGCTGAAGACCTGGCACTTTATTACTGTCAGCAATTTTATAACTATCCATT
AACGTTCGGCTCGGGGACAAAGTTGGAAATAAAA (SEQ ID NO:25)

*FIG. 13A*

MDSQAQVLMLLLLWVSGTCGDIVMSQSPSSLVVSIGEKVTMSCKSSQRLLYSANQKNYLAWYQQKPGQSPKLL
IYWASTRESGVPDRFTGSGSGTDFTLTISSVRAEDLALYYCQQFYNYPLTFGSGTKLEIK (SEQ ID NO:29)

*FIG. 13B*

ATGAGAGTGCTGATTCTTTTGTGCCTGTTCACAGCCTTTCCTGGTATCCTGTCTGATGTGCAGGAGT
CAGGACCTGACCTGGTGAAACCTTCTCAGTCTCACTTCACCTCAGTCACTGGCTACTCCATCACCAG
TGATTATAGCTGGCACTGGATCCGGCAGTTCCAGGAAACAAACTGGAATGGATGGGCTACATACACTCCAGT
GGTATCACTAACTACAACCCATCTCTCAAAAGTCGAATCTCTATCACTCGAGACACATCCAAGAACCAGTTCT
TCCTGCACTTGAGTTCTATGACTAATGAGGACACAGCCACATATTACTGTACAAGACCTCCGGTAGTAACCCG
GTACTTCGATGTCTGGGGCGCAGGGACCACGGTCACCGTCTCCCTCA (SEQ ID NO:33)

FIG. 14A

MRVLILLCLFTAFPGILSDVQLQESGPDLVKPSQSLSITCTVTGYSITSDYSWHWIRQFPGNKLEWMGYIHSS
GITNYNPSLKSRISITRDTSKNQFFLHLSSMTNEDTATYYCTRPPVVTRYFDVWGAGTTVTVSS (SEQ ID
NO:37)

FIG. 14B

ATGGAATCACAGACTCAGGTTCCTCATGTCCCTCTGCTCTTCTGGGTATCTCTGGGTACCCTGTGGGACATTGTGATGA
CACAGTCTCCATCCTCCCTGACTGTGACAGGAAGGTCACTATGAGCTGCAAGTCCAGTCAGGGTCT
GTTAGACAGTGGAAATCAAAAGAACTACTTGACCTGGTACCAGCAGAAACCAGGGCAGCCTCCTAAACTGTTG
ATCTACTGGGCATCCACTAGGAAATCTGGGGTCCCTGATCGCTTCACAGGCAGTGGATCTGGAACAGATTTCA
CTCTCACCATCAGCAGTGTGCAGGCTGAAGACCTGGCAGTTTATTACTGTCAGAATGATTATACTTATCCTCT
CACGTTCGGTGCTGGGACCAAGCTGGAGCTGAAA (SEQ ID NO:41)

*FIG. 15A*

MESQTQVLMSLLFWVSGTCGDIVMTQSPSSLTVTAGEKVTMSCKSSQGLLLDSGNQKNYLTWYQQKPGQPPKLL
IYWASTRKSGVPDRFTGSGSGTDFTLTISSVQAEDLAVYYCQNDYTYPLTFGAGTKLELK (SEQ ID NO:45)

*FIG. 15B*

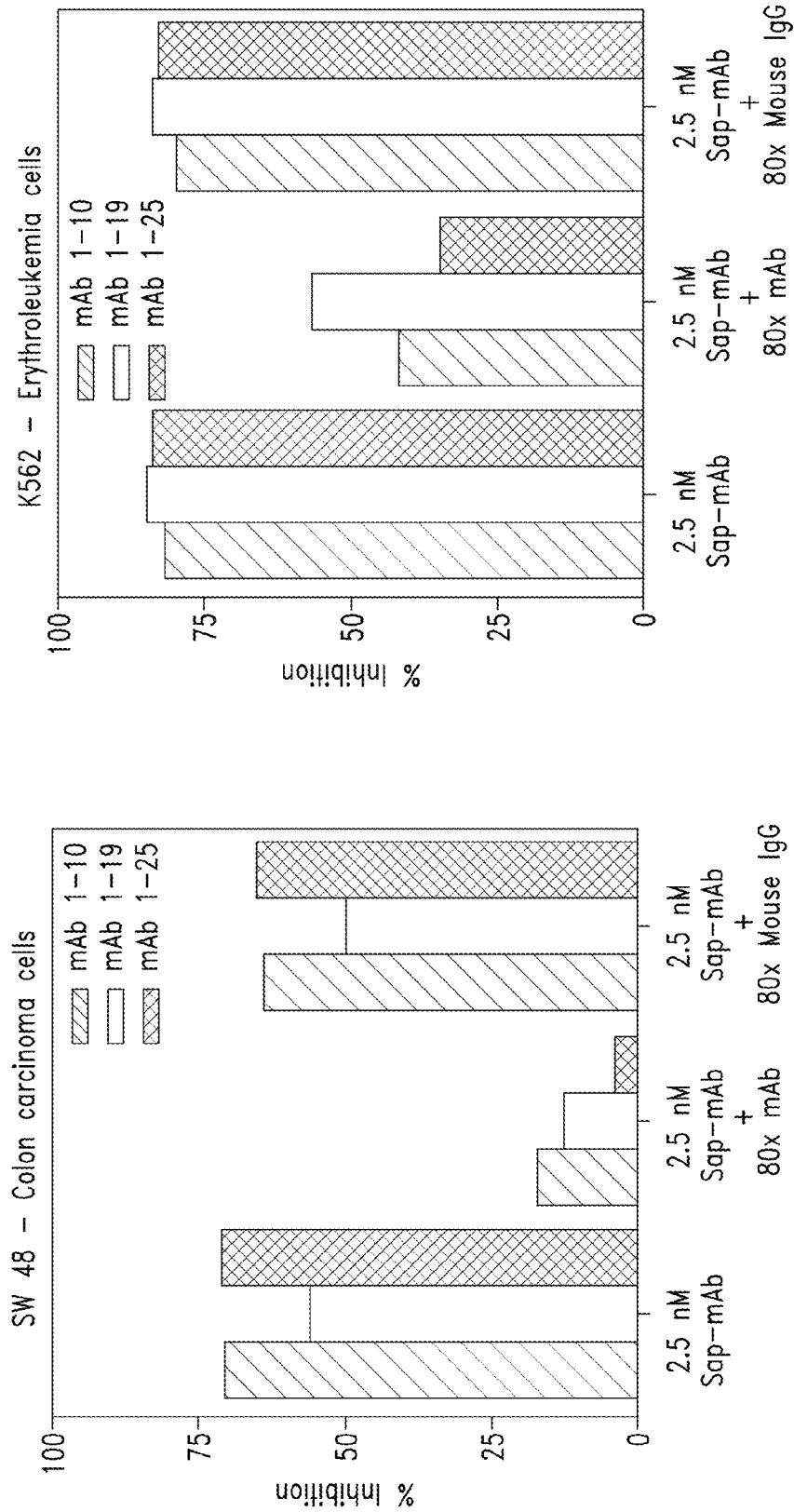

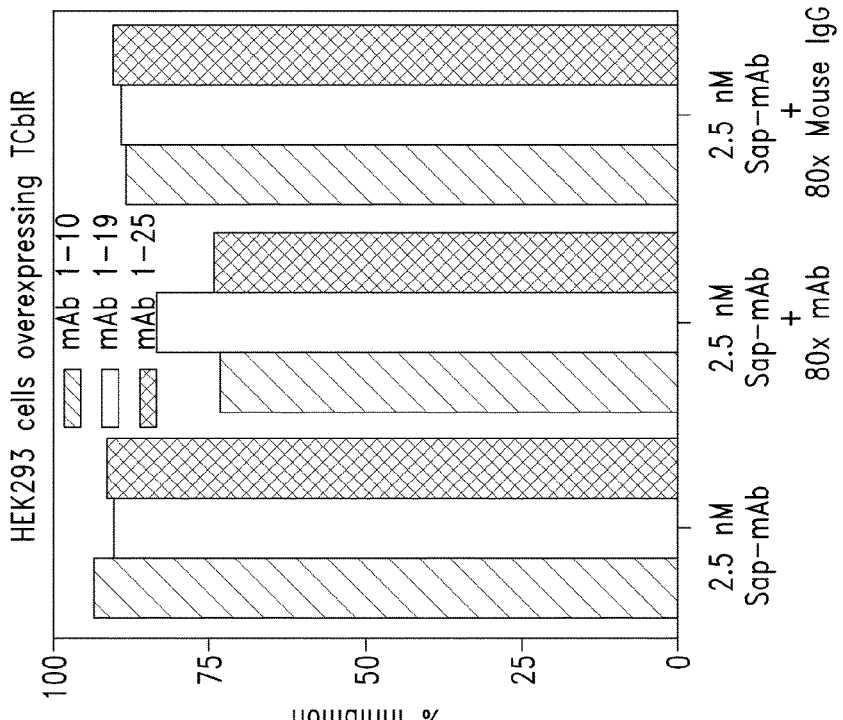
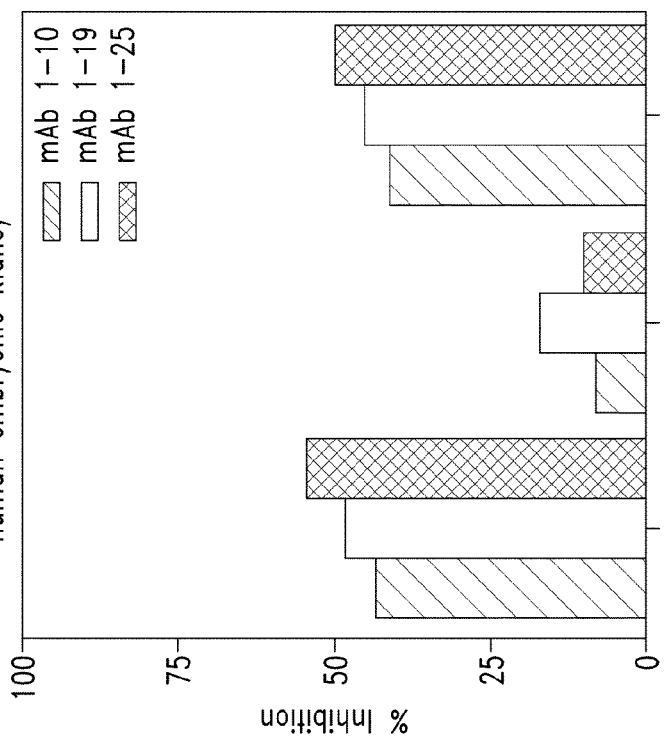
FIG. 17D
FIG. 17C

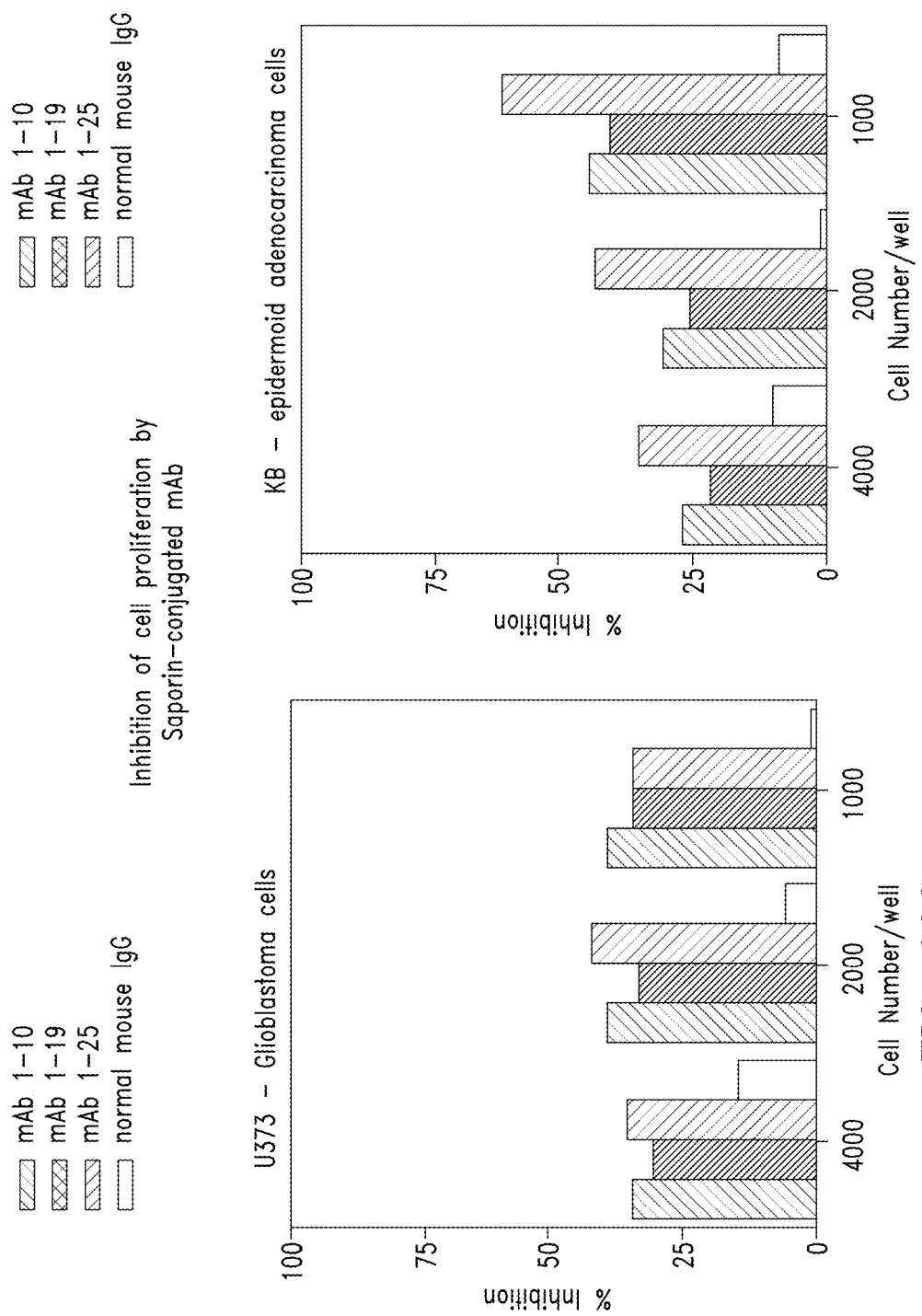

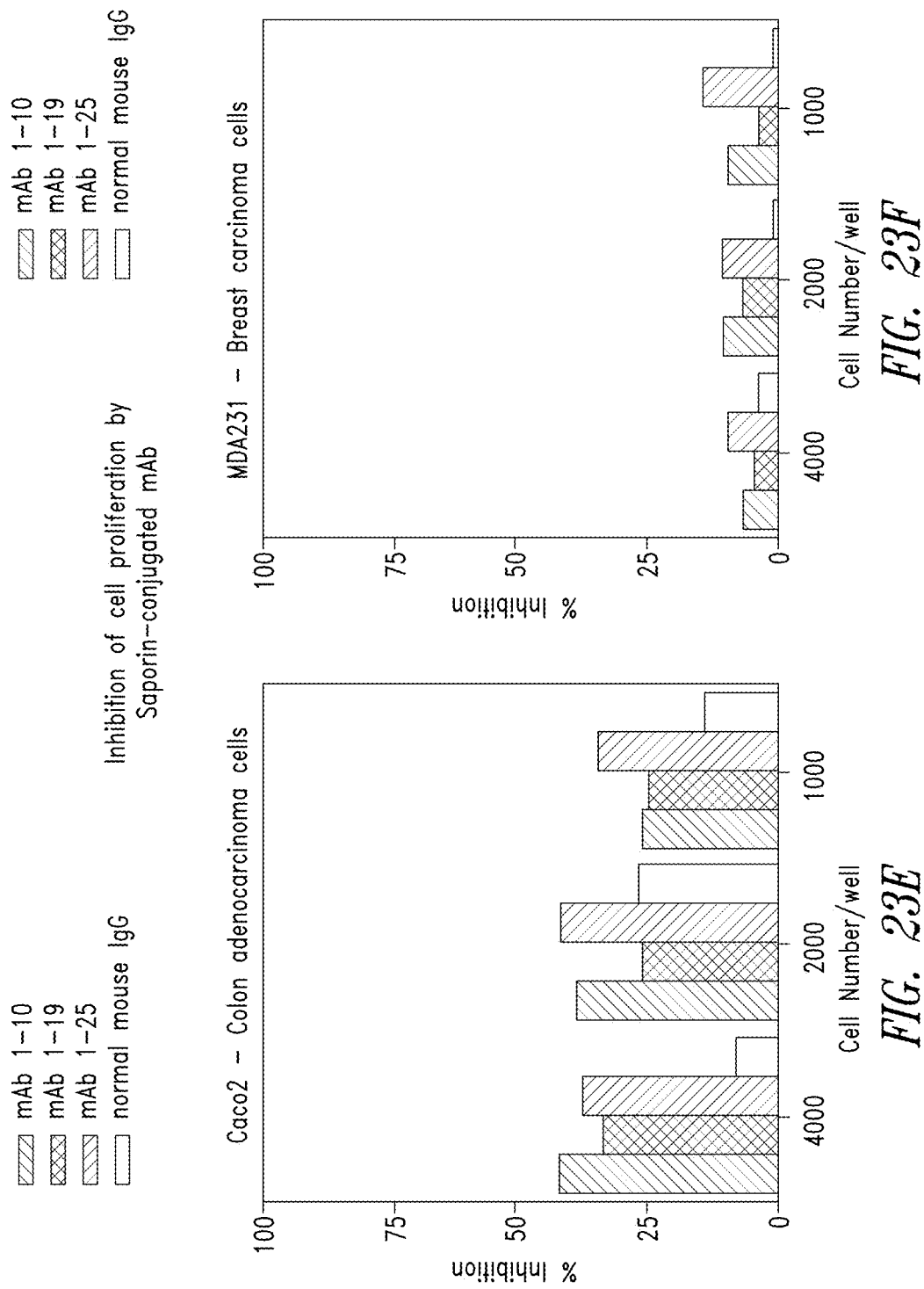

Amino acid sequence alignment of LDL-receptor type A modules of LDLR, LRP1, and TCblR

```
LB1       VGDRCE-RNEFQCQD---GKCISYKWVCDGSABCQDGSDESQETC  41
LB2      -SVTCK-SGDFSCGGRVNRCIPQFWRCDGQVDCDNGSDE--QGC   40
LB3      -PKTCS-QDEFRCHD--GKCISPQFVCDSDRDCLDGSDE--ASC   38
LB4      -VLTCG-PASFQCNS--STCIPQLWACDNEDCEDGSDEWPQRC    40
LB5       DSSPCS-AFEFHCLS--GECIHSSWRCDGGPDCKDKSDE--EMC   39
LB6      -VATCR-PDEFQCSD--GNCIHGCRKQCDREYDCKDMSDE--VGC  38
LB7      -VTLCEGPNKEKCHS--GECITLDEVCMKARCRDWSDEPIKEC    41

CR3      -PPQCQP-GEFACAN--SRCIQERWKCDGDNDCLDNSDEAPALC   40
CR4       HQHTCPS-DRFKCEN--NRCIENRWLCDGKDNDCGNSEDESNATC  41
CR5       SARTCPP-NQFSCAS--GRCIPISWTCDLDDDCGDRSDESDES-ASC 40
CR6       AYPTCFFLTQFTCNM--GRCINIMWRCDMDNDCGDNSDE--AGC  40
CR7      -SHSCSS-TQFKCNS--GRCIPEHWTCDGDNDCGDYSDETHANC   40
CR8       PPGGCHT-DEFQCRL-DGLCIPLRWRCDGDTDCMDSSDE--KSC  40
CR9       VTHVCDPSVKFGCKD-SARCISKAWVCDGHNDCEDNSDE--EMC   41
CR10      ESLACR-PSHRCANNTSVCLPPDKLCDGNDDCGDGSDBG-ELC   42

LDLR-A1   SSGSCPP-TKFQCRT-SGLCVPLTWRCDRDLCSDGSDE--EEC    40
LDLR-A2   SRLACLA-GELRCTL-SDDCIPLTWRCDGHPDCPDSSDE--LGC   40
             *         *     *        ‡‡ ‡*‡ ‡* ‡*   ††       *
```

\* conserved cysteines
† side chain carboxyl groups involved in calcium coordination
‡ backbone carbonyl groups involved in calcium coordination

FIG. 26

TCbIR mutations

| | 1st LA | | 2nd LA | binding of TC-Cbl |
|---|---|---|---|---|
| | 84　　　　　　　　　　　　　　　　　89　　　　　　　132　　　　　　　　　　　　　　　　　　　　　　　167 | | | |
| | SCHPTERQCRTSGLCVPLTWRCDRDLDCSDGSDEEECR ...... ACLAGELRCTLSDDCIPLTWRCDGHPDCPDSSDELGCG | | | |
| | | LL | | |
| mut1 D85L, E86L | | | | none |
| | 84　　　　　　　　　　　　　　　　　89　　　　　　　132　　　　　　　　　　　　　　　　　　　　　　　167 | | | |
| | SCHPTERQCRTSGLCVPLTWRCDRDLDCSDGSDEEECR ...... ACLAGELRCTLSDDCIPLTWRCDGHPDCPDSSDELGCG | | | |
| | | | LL | |
| mut2 D163L, E164L | | | | none |

FIG. 27B

ANTIBODIES TO THE B12-TRANSCOBALAMIN RECEPTOR

CROSS-REFERENCE TO RELATED APPLICATIONS

This application claims benefit under 35 U.S.C. §119(e) of U.S. provisional patent application No. 61/510,889, filed on Jul. 22, 2011 and U.S. provisional patent application No. 61/536,361, filed on Sep. 19, 2011, the contents of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is KYIP_021_02US_ST25.txt. The text file is 28 KB, was created on Aug. 20, 2014 and is being submitted electronically via EFS-Web.

BACKGROUND

1. Technical Field

The field of the present invention relates to the transcobalamin receptor, particularly anti-transcobalamin receptor antibodies and the use of the antibodies in the prevention, diagnosis, and treatment of tumors, cancer and proliferative diseases and disorders.

2. Description of the Related Art

Cellular uptake of vitamin B12 (cobalamin, Cbl) is mediated by two proteins, transcobalamin (TC), a plasma protein secreted by the vascular endothelial cells (Quadros et al. *Am J Physiol*, 277, G161-6, 1999) that binds and transports the vitamin to tissues, and the membrane receptor for TC-Cbl (TCblR/CD320), which is expressed on most cell types and binds TC saturated with cobalamin to internalize the vitamin by endocytosis (Cooper and Paranchych. *Nature*, 191, 393-5, 1961). The TC is degraded in the lysosome, and the Cbl is transported out of the lysosome (Youngdahl-Turner et al. *Exp Cell Res*, 118, 127-34, 1979) for conversion to methylCbl and adenosylCbl (Quadros and Jacobsen. *Biochim Biophys Acta*, 1244, 395-403, 1995). The two forms of Cbl serve as cofactors for two key enzymes, methionine synthase (MS) and methylmalonylCoA mutase (MMU). The conversion of methyltetrahydrofolate and homocysteine to tetrahydrofolate and methionine by MS requires methylCbl (Taylor and Hanna. *Arch Biochem Biophys*, 171, 507-20, 1975), and adenosylCbl is a cofactor for MMU for the formation of succinylCoA in the propionate metabolic pathway (Hall, *J Lab Clin Med*, 103, 70-81, 1984). TCblR expression is coupled to the cell cycle with highest receptor expression in actively dividing cells, likely preceding DNA synthesis (Hall, *J Lab Clin Med*, 103, 70-81, 1984). Cellular uptake and disposition of Cbl is a dynamic process dictated by available extracellular TC-Cbl and intracellular Cbl requirement, with most of the Cbl exiting the cell following conversion to coenzyme forms and utilization in Cbl dependent reactions (Quadros and Jacobsen. *Biochim Biophys Acta*, 1244, 395-403, 1995). TCblR (CD320) is a membrane receptor with structural homology to the LDL receptor family. The mature protein of 282 amino acids has a 198 amino acid (aa) extracellular region (amino acids 32-229 of SEQ ID NO:53), a 21 aa transmembrane stretch and a 32 aa cytoplasmic domain. The extracellular region contains two LDL receptor type A domains separated by a 55 aa cysteine rich CUB like domain (Quadros et al. *Blood*, 113: 186-192, 2009). The two LDLR-A domains with consensus aa sequences for Ca++ binding appear to be critical determinants for Ca++ dependent binding of TC-Cbl (DiGirolamo and Huennekens. *Arch Biochem Biophys*, 168, 386-93, 1975).

Cbl plays an essential role in folate recycling, and the differential expression of the receptor serves to provide optimum delivery of the vitamin to cells during the early phase of DNA synthesis. This process ensures adequate functioning of Cbl dependent enzymes, especially the methionine synthase that is essential for recycling of methyl folate to generate folates needed for purine and pyrimidine biosynthesis (Wickramasinghe S N. *Baillieres Clin Haematol* 1995; 8:441-59). The more proliferative a cell, the higher the need for folates and Cbl, and this need for Cbl is met by the increased expression of TCblR in cancer cells that may have inherently lost the ability to stop dividing and differentiate. Selective targeting of cancer cells for destruction by delivering drugs and toxins preferentially to these cells has been the ultimate objective of cancer therapy.

The search for tumor specific markers and the strategies to utilize these in cancer therapy have been pursued for decades with mixed results. This can be attributed to multiple factors that include the lack of specificity of the target antigen, cellular events that can alter the targeting and to the complex and diverse nature of cancer itself.

Clearly, there is a need in the art for new agents and methods for treating tumors, e.g., by blocking cell growth or proliferation or by delivering cytotoxic and growth inhibiting agents to tumor cells.

BRIEF SUMMARY

The present invention provides novel antibodies, and antigen-binding fragments and variants thereof, as well as related antibody conjugates, and related methods for diagnosing and imaging tumors, as well as for regulating cellular uptake of cobalamin and cell growth. Accordingly, the compositions and methods of the present invention are useful to treat and/or prevent diseases and disorders associated with increased expression of TCblR, and to identify tumor cells and target therapeutic agents to tumor cells.

Certain embodiments of the invention pertain to an isolated antibody, or an antigen-binding fragment thereof, that binds to human transcobalamin receptor (TCblR), wherein the antibody or fragment thereof comprises one or more complementarity determining region (CDR) having amino acid sequences set forth in SEQ ID NOs:6-8, 14-16, 22-24, 30-32, 38-40 and 46-48; or a variant of the antibody or fragment thereof comprising up to 8 amino acid substitutions in the one or more CDRs.

In one embodiment, the isolated antibody, or antigen-binding fragment thereof, comprises (i) a heavy chain variable (VH) region comprising VHCDR1, VHCDR2 and VHCDR3 amino acid sequences set forth in SEQ ID NOs:6, 7 and 8, respectively, and/or (ii) a light chain variable (VL) region comprising VLCDR1, VLCDR2 and VLCDR3 amino acid sequences set forth in SEQ ID NOs:14, 15 and 16, respectively; or a variant of the antibody or fragment thereof comprising VH and VL regions identical to the VH and VL regions of (i) and (ii) except for up to 8 amino acid substitutions in the CDR amino acid sequences. In a particular embodiment, the VH region comprises the amino acid sequence set forth in SEQ ID NO:5. In another embodiment, the VL region comprises the amino acid sequence set forth in SEQ ID NO:13. In one embodiment, the VH region comprises the amino acid sequence set forth in SEQ ID NO:5, and the VL region comprises the amino acid sequence set forth in SEQ ID NO:13.

In another embodiment, the isolated antibody, or antigen-binding fragment thereof, comprises (i) a VH region comprising VHCDR1, VHCDR2 and VHCDR3 amino acid sequences set forth in SEQ ID NOs:22, 23 and 24, respectively, and/or (ii) a VL region comprising VLCDR1, VLCDR2 and VLCDR3 amino acid sequences set forth in SEQ ID NOs:30, 31 and 32, respectively; or a variant of the antibody or fragment thereof, comprising VH and VL regions identical to the VH and VL regions of (i) and (ii) except for up to 8 amino acid substitutions in the CDR amino acid sequences. In one embodiment, the VH region comprises the amino acid sequence set forth in SEQ ID NO:21. In another embodiment, the VL region comprises the amino acid sequence set forth in SEQ ID NO:29. In yet another embodiment, the VH region comprises the amino acid sequence set forth in SEQ ID NO:21, and the VL region comprises the amino acid sequence set forth in SEQ ID NO:29.

In another embodiment, the isolated antibody, or antigen-binding fragment or variant thereof, comprises (i) a VH region comprising VHCDR1, VHCDR2 and VHCDR3 amino acid sequences set forth in SEQ ID NOs:38, 39 and 40, respectively, and/or (ii) a VL region comprising VLCDR1, VLCDR2 and VLCDR3 amino acid sequences set forth in SEQ ID NOs:46, 47 and 48, respectively; or a variant of the antibody or fragment thereof, comprising VH and VL regions identical to the VH and VL regions of (i) and (ii) except for up to 8 amino acid substitutions in the CDR amino acid sequences. In one embodiment, the VH region comprises the amino acid sequence set forth in SEQ ID NO:37. In another embodiment, the VL region comprises the amino acid sequence set forth in SEQ ID NO:45. In yet another embodiment, the VH region comprises the amino acid sequence set forth in SEQ ID NO:37, and the VL region comprises the amino acid sequence set forth in SEQ ID NO:45.

In a particular embodiment, the isolated antibody, or antigen-binding fragment or variant thereof, comprises a VH region comprising the amino acid sequence set forth in one of SEQ ID NOs:5, 21 and 37. In a related embodiment, the VL region comprises an amino acid sequence having at least 90% identity to the amino acid sequence set forth in SEQ ID NO:13, and the VH region comprises the amino acid sequence set forth in SEQ ID NO:5. In another embodiment, the VL region comprises an amino acid sequence having at least 90% identity to the amino acid sequence set forth in SEQ ID NO:29, and the VH region comprises the amino acid sequence set forth in SEQ ID NO:21. In yet another embodiment, the VL region comprises an amino acid sequence having at least 90% identity to the amino acid sequence set forth in SEQ ID NO:45, and the VH region comprises the amino acid sequence set forth in SEQ ID NO:37.

In one embodiment, the isolated antibody, or an antigen-binding fragment or variant thereof, comprises a VL region comprising the amino acid sequence set forth in one of SEQ ID NOs:13, 29 and 45. In a related embodiment, the VH region comprises an amino acid sequence having at least 90% identity to the amino acid sequence set forth in SEQ ID NO:5, and the VL region comprises the amino acid sequence set forth in SEQ ID NO:13. In another embodiment, the VH region comprises an amino acid sequence having at least 90% identity to the amino acid sequence set forth in SEQ ID NO:21, and the VL region comprises the amino acid sequence set forth in SEQ ID NO:29. In yet another embodiment, the VH region comprises an amino acid sequence having at least 90% identity to the amino acid sequence set forth in SEQ ID NO:37, and the VL region comprises the amino acid sequence set forth in SEQ ID NO:45.

In certain embodiments, the antibody is humanized. In another embodiment, the antibody is monoclonal. In a particular embodiment, the antibody is conjugated to an agent selected from a chemotherapeutic, a drug, a toxin and an imaging compound. In one embodiment, the antibody is conjugated to the agent via only one or more covalent bonds. In specific embodiments, the agent is saporin.

In another embodiment, the isolated antibody, or antigen-binding fragment or variant thereof, inhibits cobalamin (Cbl) from binding to TCblR. In one embodiment, the antibody binds an epitope present in amino acid residues 54-89 or amino acid residues 132-167 of the human TCblR amino acid sequence set forth in SEQ ID NO:53. In yet another embodiment, the isolated antibody, or antigen-binding fragment or variant thereof, is one that competes with any one of the antibodies described above for binding to human TCblR.

Certain embodiments relate to an isolated polynucleotide encoding the isolated antibody, or antigen-binding fragment or variant thereof. One embodiment provides an expression vector comprising the polynucleotide. A related embodiment pertains to a host cell comprising the expression vector.

Another embodiment pertains to a composition comprising a physiologically acceptable carrier and a therapeutically effective amount of the isolated antibody, or antigen-binding fragment thereof. One embodiment provides a method for treating a patient having a tumor, comprising providing to the patient the composition, thereby treating the patient having the tumor. In certain embodiments, the antibody is conjugated to an agent selected from the group consisting of a chemotherapeutic, a drug and a toxin. In one embodiment, the antibody is conjugated to the agent via only one or more covalent bonds. In specific embodiments, the agent is saporin. Another embodiment provides a kit comprising the composition.

Yet another embodiment provides a method for inhibiting the growth of a tumor cell that expresses TCblR comprising contacting the cell with the antibody, or antigen-binding fragment or variant thereof.

Another embodiment provides a method of inhibiting cobalamin uptake by a cell that expresses TCblR comprising contacting the cell with an antibody, or antigen-binding fragment thereof, comprising one or more CDR amino acid sequences set forth in SEQ ID NOs:38-40 and 46-48; or a variant of the antibody or fragment thereof comprising up to 8 amino acid substitutions in the one or more CDRs. In certain embodiments, the antibody or antigen-binding fragment or variant thereof, comprises (i) a heavy chain variable (VH) region comprising VHCDR1, VHCDR2 and VHCDR3 amino acid sequences set forth in SEQ ID NOs:38, 39 and 40, respectively, and/or (ii) a light chain variable (VL) region comprising VLCDR1, VLCDR2 and VLCDR3 amino acid sequences set forth in SEQ ID NOs:46, 47 and 48, respectively; or a variant of the antibody, or antigen-binding fragment thereof, comprising VH and VL regions identical to the VH and VL regions of (i) and (ii) except for up to 8 amino acid substitutions in the CDR regions. In one embodiment, the VH region comprises the amino acid sequence set forth in SEQ ID NO:37. In another embodiment, the VL region comprises the amino acid sequence set forth in SEQ ID NO:45. In yet another embodiment, the VH region comprises the amino acid sequence set forth in SEQ ID NO:37, and the VL region comprises the amino acid sequence set forth in SEQ ID NO:45.

Another aspect of the invention relates to a method of identifying an antibody or fragment thereof that inhibits cobalamin uptake by a cell that expresses TCblR comprising: contacting a candidate antibody or fragment thereof with a first polypeptide comprising the extracellular domain of TCblR, or a region thereof, capable of binding an antibody or fragment thereof comprising a VH region comprising the amino acid sequence set forth in SEQ ID NO:37 and a VL region comprising the amino acid sequence set forth in SEQ ID NO:45; determining a first amount of binding of the candidate antibody or fragment thereof to the first polypeptide; contacting the candidate antibody or fragment thereof with a polypeptide comprising the extracellular domain of TCblR, or a region thereof capable of binding the antibody or fragment thereof; wherein one or more amino acid residues of the second polypeptide or region thereof are mutated such that the second polypeptide or fragment thereof has a reduced ability to bind said antibody or fragment thereof; and determining a second amount of binding of the candidate antibody or fragment thereof to the second polypeptide, wherein if the first amount of binding to the candidate antibody or fragment thereof is greater than the second amount of binding to the candidate antibody or fragment thereof, the candidate antibody or fragment thereof inhibits cobalamin uptake by a cell that expresses TCblR.

Another embodiment provides a method of identifying an antibody or fragment thereof that inhibits cobalamin uptake by a cell that expresses TCblR comprising: contacting a candidate antibody or fragment thereof with a first cell or population of cells that expresses a first polypeptide comprising the extracellular domain of TCblR, or a region thereof, capable of binding an antibody or fragment thereof comprising a VH region comprising the amino acid sequence set forth in SEQ ID NO:37 and a VL region comprising the amino acid sequence set forth in SEQ ID NO:45; determining a first amount of binding of the candidate antibody or fragment thereof to the first cell or population of cells; contacting the candidate antibody or fragment thereof with a second cell or population of cells that expresses a second polypeptide comprising the extracellular domain of TCblR, or a region thereof capable of binding the antibody or fragment thereof; wherein one or more amino acid residues of the second polypeptide or region thereof are mutated such that the second polypeptide or fragment thereof has a reduced ability to bind said antibody or fragment thereof; and determining a second amount of binding of the candidate antibody or fragment thereof to the second cell, wherein if the first amount of binding to the candidate antibody or fragment thereof is greater than the second amount of binding to the candidate antibody or fragment thereof, the candidate antibody or fragment thereof inhibits cobalamin uptake by a cell that expresses TCblR.

In a related embodiment, the second polypeptide comprises one or more amino acid substitutions, deletions, or insertions within one or more LDLR-A domain of TCblR. In yet another embodiment, the second polypeptide comprises one or more amino acid substitutions, deletions, or insertions within a region of TCblR selected from the group consisting of: amino acid residues 54-89, amino acid residues 132-167, amino acid residues 53-63, amino acid residue 85, amino acid residue 86, amino acid residues 150-167, amino acid residue 163, and amino acid residue 164, of SEQ ID NO:53.

Another embodiment relates to a method of identifying an antibody or fragment thereof that inhibits cobalamin uptake by a cell that expresses TCblR comprising: contacting a candidate antibody or fragment thereof with a polypeptide comprising a region of TCblR capable of binding an antibody or fragment thereof comprising a VH region comprising the amino acid sequence set forth in SEQ ID NO:37 and a VL region comprising the amino acid sequence set forth in SEQ ID NO:45; and determining an amount of binding of the candidate antibody or fragment thereof to the polypeptide; wherein if the determined amount of binding is significantly greater than the amount of binding to a control polypeptide, the candidate antibody or fragment thereof inhibits cobalamin uptake by a cell that expresses TCblR. One embodiment provides a method of identifying an antibody or fragment thereof that inhibits cobalamin uptake by a cell that expresses TCblR comprising: contacting a candidate antibody or fragment thereof with a cell or population of cells that expresses a polypeptide comprising a region of TCblR capable of binding an antibody or fragment thereof comprising a VH region comprising the amino acid sequence set forth in SEQ ID NO:37 and a VL region comprising the amino acid sequence set forth in SEQ ID NO:45; and determining an amount of binding of the candidate antibody or fragment thereof to the cell or population of cells; wherein if the determined amount of binding to the candidate antibody or fragment thereof is greater than the amount of binding to a control cell or population of cells, the candidate antibody or fragment thereof inhibits cobalamin uptake by a cell that expresses TCblR. In a related embodiment, the polypeptide comprises amino acid residues 32-183 of SEQ ID NO:53.

BRIEF DESCRIPTION OF THE SEVERAL VIEWS OF THE DRAWINGS

FIG. 5A shows membrane expression of TCblR-GFP and surface binding of Qdot 625red indicated by evenly scattered low level fluorescence, and internalization of Qdot 625red is indicated by brighter segregated red-green/yellow fluorescence at 37° C. (FIG. 5B). FIG. 5C shows a lack of uptake when normal mouse IgG is substituted for the mAb, and FIG. 5D shows the uptake of Qdot 625red in K562 cells incubated with anti-TCblR mAb.

FIG. 10 depicts the VH region of the mAb 1-19 anti-TCblR antibody. FIG. 10A shows the polynucleotide sequence (SEQ ID NO:1) encoding the amino acid sequence (FIG. 10B; SEQ ID NO:5). The region corresponding to the leader sequence is italicized, and the regions corresponding to VHCDR1, VHCDR2 and VHCDR3 (SEQ ID NOs:2-4 and 6-8, respectively) are underlined.

FIG. 11 depicts the VL region of the mAb 1-19 anti-TCblR antibody. FIG. 11A shows the polynucleotide sequence (SEQ ID NO:9) encoding the amino acid sequence (FIG. 11B; SEQ ID NO:13). The region corresponding to the leader sequence is italicized, and the regions corresponding to VLCDR1, VLCDR2 and VLCDR3 (SEQ ID NOs:10-12 and 14-16, respectively) are underlined.

FIG. 12 depicts the VH region of the mAb 1-23 anti-TCblR antibody. FIG. 12A shows the polynucleotide sequence (SEQ ID NO:17) encoding the amino acid sequence (FIG. 12B; SEQ ID NO:21). The region corresponding to the leader sequence is italicized, and the regions corresponding to VHCDR1, VHCDR2 and VHCDR3 (SEQ ID NOs:18-20 and 22-24, respectively) are underlined.

FIG. 13 depicts the VL region of the mAb 1-23 anti-TCblR antibody. FIG. 13A shows the polynucleotide sequence (SEQ ID NO:25) encoding the amino acid sequence (FIG. 13B; SEQ ID NO:29). The region corresponding to the leader sequence is italicized, and the regions corresponding to VLCDR1, VLCDR2 and VLCDR3 (SEQ ID NOs:26-28 and 30-32, respectively) are underlined.

FIG. 14 depicts the VH region of the mAb 1-25 anti-TCblR antibody. FIG. 14A shows the polynucleotide sequence (SEQ ID NO:33) encoding the amino acid sequence (FIG. 14B; SEQ ID NO:37). The region corresponding to the leader sequence is italicized, and the regions corresponding to VHCDR1, VHCDR2 and VHCDR3 (SEQ ID NOs:34-36 and 38-40, respectively) are underlined.

FIG. 15 depicts the VL region of the mAb 1-25 anti-TCblR antibody. FIG. 15A shows the polynucleotide sequence (SEQ ID NO:41) encoding the amino acid sequence (FIG. 15B; SEQ ID NO:45). The region corresponding to the leader sequence is italicized, and the regions corresponding to VLCDR1, VLCDR2 and VLCDR3 (SEQ ID NOs:42-44 and 46-48, respectively) are underlined.

FIG. 16A shows K562 cells, FIG. 16B shows U266 cells, and FIG. 16C shows SW48 cells. For each different TCblR concentration depicted, the bar at the left is mAb 1-10, the midde bar is mAb 1-19, and the bar at the right is mAb 1-25.

FIGS. 17A-D are bar graphs that show the effect of unlabeled mAb and normal mouse IgG on inhibition of cell proliferation by saporin-conjugated mAb. SW48 cells, K562 cells, normal HEK293 cells and HEK293 cells over-expressing TCblR are shown in FIGS. 17A-D, respectively. For each different treatment depicted, the bar at the left is mAb 1-10, the midde bar is mAb 1-19, and the bar at the right is mAb 1-25.

FIGS. 23A-23F are bar graphs that show the inhibition of cell proliferation by saporin-conjugated mAb in 181 cells (FIG. 23A), RKO cells (FIG. 23B), U373 cells (FIG. 23C), KB cells (FIG. 23D), Caco2 cells (FIG. 23E) and MDA231 cells (FIG. 23F). For each treatment depicted, the bars from left to right refer to mAb 1-10, mAb 1-19, mAb 1-25, and normal mouse IgG.

FIG. 26 is an amino acid sequence alignment of LDLR class A domains of LDLR, LRP1 and TCblR. Seven LA repeats (LB 1-7) from LDLR, eight LA repeats (CR 3-10) from LRP and two LA repeats (LA 1-2) from TCblR show remarkable conservation of sequences in the form of 6 cysteines and in the residues involved in Ca++ binding.

FIGS. 27A and 27B show the binding of radio labeled TC-Cbl to various truncated and mutated TCblR, respectively. Culture medium from HEK293 cells stably transfected with the various deletion constructs was incubated with radio labeled TC-Cbl and binding (+) or loss of binding (−) to the receptor was determined as described in the methods section. The intact secreted form of extracellular TCblR served as the positive control and normal HEK293 culture medium served as the negative control.

BRIEF DESCRIPTION OF THE SEQUENCES

Figure 1:
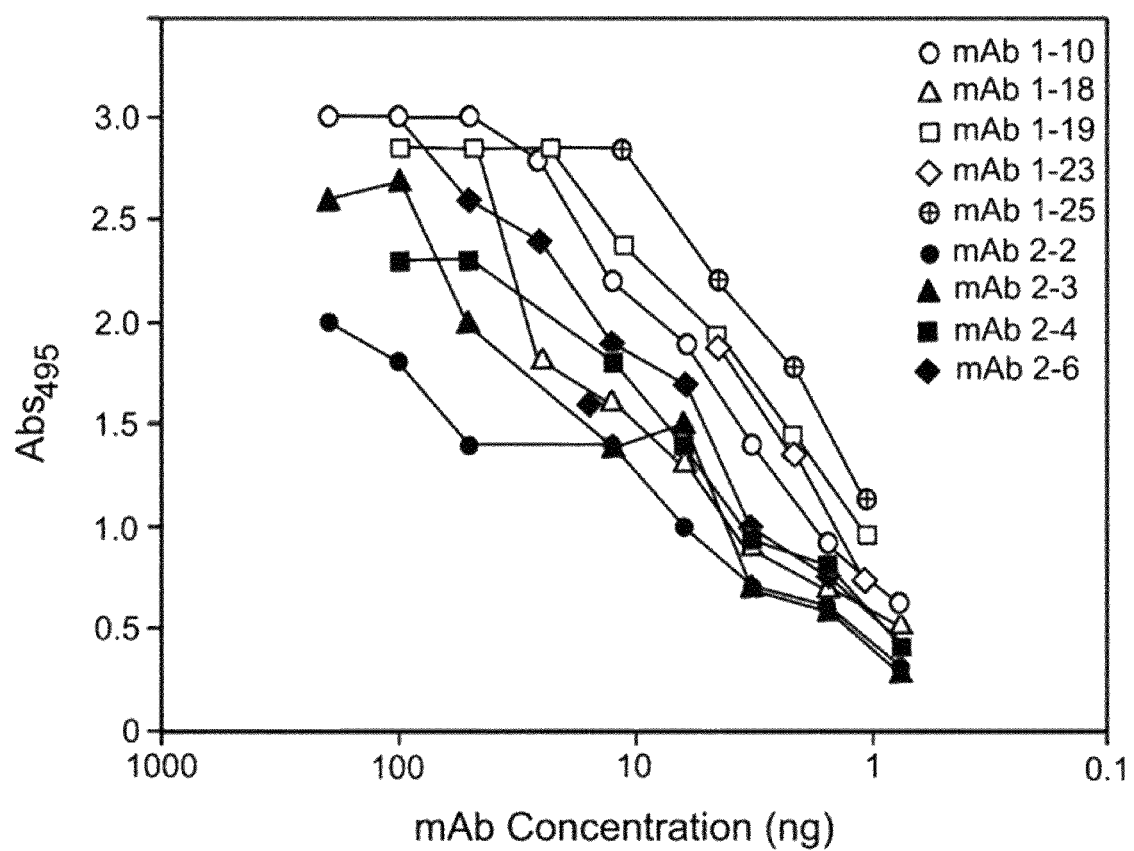
FIG. 1 is a line graph that shows the titer of anti-TCblR antibodies. Antibody titer in hybridoma supernatants was determined by ELISA. 100 ng of antigen was used to coat ELISA plates. Peroxidase conjugated goat anti-mouse secondary antibody and TMB substrate were used to detect the binding of anti-TCblR antibody.

SEQ ID NO:1 is the polynucleotide sequence encoding the VH region of the mAb 1-19 anti-TCblR antibody.

SEQ ID NO:2 is the polynucleotide sequence encoding the VHCDR1 region of the mAb 1-19 anti-TCblR antibody.

SEQ ID NO:3 is the polynucleotide sequence encoding the VHCDR2 region of the mAb 1-19 anti-TCblR antibody.

SEQ ID NO:4 is the polynucleotide sequence encoding the VHCDR3 region of the mAb 1-19 anti-TCblR antibody.

SEQ ID NO:5 is the amino acid sequence of the VH region of the mAb 1-19 anti-TCblR antibody.

SEQ ID NO:6 is the amino acid sequence of the VHCDR1 region of the mAb 1-19 anti-TCblR antibody.

SEQ ID NO:7 is the amino acid sequence of the VHCDR2 region of the mAb 1-19 anti-TCblR antibody.

SEQ ID NO:8 is the amino acid sequence of the VHCDR3 region of the mAb 1-19 anti-TCblR antibody.

SEQ ID NO:9 is the polynucleotide sequence encoding the VL region of the mAb 1-19 anti-TCblR antibody.

SEQ ID NO:10 is the polynucleotide sequence encoding the VLCDR1 region of the mAb 1-19 anti-TCblR antibody.

SEQ ID NO:11 is the polynucleotide sequence encoding the VLCDR2 region of the mAb 1-19 anti-TCblR antibody.

SEQ ID NO:12 is the polynucleotide sequence encoding the VLCDR3 region of the mAb 1-19 anti-TCblR antibody.

SEQ ID NO:13 is the amino acid sequence of the VL region of the mAb 1-19 anti-TCblR antibody.

SEQ ID NO:14 is the amino acid sequence of the VLCDR1 region of the mAb 1-19 anti-TCblR antibody.

SEQ ID NO:15 is the amino acid sequence of the VLCDR2 region of the mAb 1-19 anti-TCblR antibody.

SEQ ID NO:16 is the amino acid sequence of the VLCDR3 region of the mAb 1-19 anti-TCblR antibody.

SEQ ID NO:17 is the polynucleotide sequence encoding the VH region of the mAb 1-23 anti-TCblR antibody.

SEQ ID NO:18 is the polynucleotide sequence encoding the VHCDR1 region of the mAb 1-23 anti-TCblR antibody.

SEQ ID NO:19 is the polynucleotide sequence encoding the VHCDR2 region of the mAb 1-23 anti-TCblR antibody.

SEQ ID NO:20 is the polynucleotide sequence encoding the VHCDR3 region of the mAb 1-23 anti-TCblR antibody.

SEQ ID NO:21 is the amino acid sequence of the VH region of the mAb 1-23 anti-TCblR antibody.

SEQ ID NO:22 is the amino acid sequence of the VHCDR1 region of the mAb 1-23 anti-TCblR antibody.

SEQ ID NO:23 is the amino acid sequence of the VHCDR2 region of the mAb 1-23 anti-TCblR antibody.

SEQ ID NO:24 is the amino acid sequence of the VHCDR3 region of the mAb 1-23 anti-TCblR antibody.

SEQ ID NO:25 is the polynucleotide sequence encoding the VL region of the mAb 1-23 anti-TCblR antibody.

SEQ ID NO:26 is the polynucleotide sequence encoding the VLCDR1 region of the mAb 1-23 anti-TCblR antibody.

SEQ ID NO:27 is the polynucleotide sequence encoding the VLCDR2 region of the mAb 1-23 anti-TCblR antibody.

SEQ ID NO:28 is the polynucleotide sequence encoding the VLCDR3 region of the mAb 1-23 anti-TCblR antibody.

SEQ ID NO:29 is the amino acid sequence of the VL region of the mAb 1-23 anti-TCblR antibody.

SEQ ID NO:30 is the amino acid sequence of the VLCDR1 region of the mAb 1-23 anti-TCblR antibody.

SEQ ID NO:31 is the amino acid sequence of the VLCDR2 region of the mAb 1-23 anti-TCblR antibody.

SEQ ID NO:32 is the amino acid sequence of the VLCDR3 region of the mAb 1-23 anti-TCblR antibody.

SEQ ID NO:33 is the polynucleotide sequence encoding the VH region of the mAb 1-25 anti-TCblR antibody.

SEQ ID NO:34 is the polynucleotide sequence encoding the VHCDR1 region of the mAb 1-25 anti-TCblR antibody.

SEQ ID NO:35 is the polynucleotide sequence encoding the VHCDR2 region of the mAb 1-25 anti-TCblR antibody.

SEQ ID NO:36 is the polynucleotide sequence encoding the VHCDR3 region of the mAb 1-25 anti-TCblR antibody.

SEQ ID NO:37 is the amino acid sequence of the VH region of the mAb 1-25 anti-TCblR antibody.

SEQ ID NO:38 is the amino acid sequence of the VHCDR1 region of the mAb 1-25 anti-TCblR antibody.

SEQ ID NO:39 is the amino acid sequence of the VHCDR2 region of the mAb 1-25 anti-TCblR antibody.

SEQ ID NO:40 is the amino acid sequence of the VHCDR3 region of the mAb 1-25 anti-TCblR antibody.

SEQ ID NO:41 is the polynucleotide sequence encoding the VL region of the mAb 1-25 anti-TCblR antibody.

SEQ ID NO:42 is the polynucleotide sequence encoding the VLCDR1 region of the mAb 1-25 anti-TCblR antibody.

SEQ ID NO:43 is the polynucleotide sequence encoding the VLCDR2 region of the mAb 1-25 anti-TCblR antibody.

SEQ ID NO:44 is the polynucleotide sequence encoding the VLCDR3 region of the mAb 1-25 anti-TCblR antibody.

SEQ ID NO:45 is the amino acid sequence of the VL region of the mAb 1-25 anti-TCblR antibody.

SEQ ID NO:46 is the amino acid sequence of the VLCDR1 region of the mAb 1-25 anti-TCblR antibody.

SEQ ID NO:47 is the amino acid sequence of the VLCDR2 region of the mAb 1-25 anti-TCblR antibody.

SEQ ID NO:48 is the amino acid sequence of the VLCDR3 region of the mAb 1-25 anti-TCblR antibody.

SEQ ID NO:49 is the *Homo sapiens* CD320 molecule, transcript variant 1, mRNA, accession number NM_016579.

SEQ ID NO:50 is the *Homo sapiens* full open reading frame cDNA clone RZPDo834A0912D for gene 8D6A, 8D6 antigen; complete cds, including stop codon, accession number CR457174.

SEQ ID NO:51 is the *Homo sapiens* CD320 molecule, mRNA (cDNA clone MGC:828 IMAGE:3347569), complete cds, accession number BC000668.

SEQ ID NO:52 is the *Homo sapiens* CD320 molecule, mRNA (cDNA clone MGC:14623 IMAGE:4076237), complete cds, accession number BC007083.

SEQ ID NO:53 is the CD320 antigen isoform 1 precursor [*Homo sapiens*] amino acid sequence, accession number NP_057663.

DETAILED DESCRIPTION

The present disclosure relates to antibodies and antigen-binding fragments thereof that specifically bind to the transcobalamin receptor (TCblR), including particular antibodies having specific epitopic specificity and functional properties.

TCblR is over-expressed in proliferating and dividing cells, including tumor cells. Certain embodiments of the invention pertain to the use of anti-TCblR antibodies or antigen-binding fragments thereof for the diagnosis, assessment and treatment of diseases and disorders associated with increased expression thereof. For example, the subject antibodies may be used in the treatment or prevention of cancer, tumors and proliferative diseases and disorders. One embodiment of the invention encompasses specific antibodies and fragments thereof capable of binding to TCblR, blocking TCblR binding with TCbl, and inhibiting Cbl dependent cell growth and proliferation. In more specific embodiments of the invention, the antibodies described herein are conjugated to an agent useful for diagnosis or treatment.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

DEFINITIONS

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to the Transcobalamin receptor (TCblR). In particular, the antibodies described herein specifically bind to TCblR and have therapeutic utility for the treatment of diseases, including those associated with elevated or aberrant expression TCblR. Certain antibodies described herein may also block TCblR binding to the TCblR, thereby blocking cellular uptake of Cbl. The antibodies described herein may also have effects on TCblR receptor internalization. Certain antibodies described herein are internalized by cells expressing TCblR, and may be used to deliver an agent, e.g., a therapeutic agent, to such cells.

Sequences of illustrative antibodies, or antigen-binding fragments, or domains or complementarity determining regions (CDRs) thereof, are set forth in SEQ ID NOs:5-8, 13-16, 21-24, 29-32, 37-40 and 45-48.

The term "antibody" (Ab) as used herein includes monoclonal antibodies, polyclonal antibodies, multispecific antibodies (e.g., bispecific antibodies), and antibody fragments, so long as they exhibit the desired biological activity, e.g., specifically bind to TCblR. The term "immunoglobulin" (Ig) is used interchangeably with "antibody" herein.

The basic antibody unit is a heterotetrameric glycoprotein composed of two identical light (L) chains and two identical heavy (H) chains. Each light chain is linked to a heavy chain by one covalent disulfide bond, while the two heavy chains are linked to each other by one or more disulfide bonds depending on the heavy chain isotype. Each heavy and light chain also has regularly spaced intrachain disulfide bridges. Each heavy chain has at the N-terminus a variable domain ($V_H$) followed by three constant domains ($C_H$) for each of the α and γ chains and four $C_H$ domains for μ and ε isotypes. Each light chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site.

The light chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. It will be appreciated that mammals encoding multiple Ig isotypes will be able to undergo isotype class switching.

An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain. In the case of IgG, the 4-chain unit is generally about 150,000 Daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The V domain mediates antigen binding and defines specificity of a particular antibody for its particular antigen. The gene sequence encoding the $V_H$ domain has multiple copies of variable (V), diversity (D), and joining (J) segments. The gene sequence encoding the $V_L$ domain contains multiple copies of V and J segments. The $V_H$ and $V_L$ regions undergo gene rearrangement (i.e., somatic recombination) to develop diverse antigen specificity in antibodies. The term "variable" refers to the fact that certain segments of the V domains differ extensively in sequence among antibodies.

However, the variability is not evenly distributed across the 110-amino acid span of the variable domains. Instead, the V regions consist of relatively invariant stretches called framework regions (FRs) of 15-30 amino acids separated by short regions of extreme variability called "hypervariable regions." These hypervariable regions are the result of somatic hypermutation during the affinity maturation process, and they are typically each 9-18 amino acids long. However, they have been found to range from 4-28 amino acids in length depending upon the particular epitope. For example, CDR3 regions up to at least 22 or 23 amino acids in length have been described. See, e.g., Morea V, et al., *J Mol Biol.* 275(2):269-94 (1998) and Kabat, E. A., et al., *Sequences of Proteins of Immunological Interest*, Fifth Edition. NIH Publication No. 91-3242 (1991).

The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 53-55 (H2) and 96-101 (H3) in the $V_H$; Chothia and Lesk, *J. Mol. Biol.* 196:901-917 (1987)).

As used herein, "VHCDR" and "VLCDR" refer to a CDR that is in the VH or VL, respectively. In particular, the six CDRs of an antibody described herein may be designated VHCDR1, VHCDR2, VHCDR3, VLCDR1, VLCDR2 and VLCDR3.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody is purified: (1) to greater than 95% by weight of antibody as determined by the Bradford method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variants thereof. Preferably, the intact antibody has one or more effector functions.

An "antibody fragment" is a polypeptide comprising or consisting of a portion of an intact antibody, preferably the antigen-binding or variable region of the intact antibody. Examples of antibody fragments include Fab, Fab', F(ab')$_2$, and Fv fragments; diabodies; linear antibodies (see U.S. Pat. No. 5,641,870; Zapata et al., *Protein Eng.* 8(10): 1057-1062 [1995]); single-chain antibody molecules; and multispecific antibodies formed from antibody fragments. In particular, an "antigen-binding fragment" is a polypeptide comprising a portion of an intact antibody that specifically binds the target antigen, e.g., TCblR.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Both the Fab and F(ab')$_2$ are examples of antigen-binding fragments. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions (i.e., the CH2 and CH3 domains) of both H chains held together by disulfides. The effector functions of antibodies are determined by sequences in the Fc region. The Fc domain is the portion of the antibody recognized by cell receptors, such as the FcR, and to which the complement-activating protein, C1q, binds.

"Fv" is the minimum antibody fragment that contains a complete antigen-recognition and antigen-binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. Preferably, the scFv polypeptide further comprises a polypeptide linker between the $V_H$ and $V_L$ domains that enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing scFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; PCT Publication No. WO 93/11161; and Hollinger et al., *Proc. Natl. Acad. Sci. USA*, 90:6444-6448 (1993).

As used herein, the term "polyclonal antibody" refers to an antibody obtained from a population of antigen-specific antibodies that recognize more than one epitope of the specific antigen.

"Antigen" or "immunogen" refers to a peptide, lipid, polysaccharide or polynucleotide which is recognized by the adaptive immune system. Antigens may be self or non-self molecules. Examples of antigens include, but are not limited to, bacterial cell wall components, pollen, and rh factor. The region of an antigen that is specifically recognized by a specific antibody is an "epitope" or "antigenic determinant." A single antigen may have multiple epitopes.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The antibodies herein include "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, U.S. Pat. Nos. 4,816,567; 5,530,101 and 7,498,415; and Morrison et al., *Proc. Natl. Acad. Sci. USA*, 81:6851-6855 (1984)). For example, chimeric antibodies may comprise human and non-human residues. Furthermore, chimeric antibodies may comprise residues that are not found in the recipient antibody or in the donor antibody. These modifications are made to further refine antibody performance. For further details, see Jones et al., *Nature* 321:522-525 (1986); Riechmann et al., *Nature* 332:323-329 (1988); and Presta, *Curr. Op. Struct. Biol.* 2:593-596 (1992). Chimeric antibodies also include primatized and humanized antibodies.

In certain embodiments, the anti-TCblR antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of the anti-TCblR antibodies disclosed herein include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffold for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-

327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which are also termed one or more CDRs "derived from" one or more CDRs from the original antibody.

A "human antibody" can be an antibody containing only sequences present in an antibody naturally produced by a human. However, as used herein, human antibodies may comprise residues or modifications not found in a naturally occurring human antibody, including those modifications and variant sequences described herein, i.e., a human antibody is still "human" even if amino acid substitutions or amino acid modifications are made in the antibody. These are typically made to further refine or enhance antibody performance. In some instances, human antibodies are produced by transgenic animals. For example, see U.S. Pat. Nos. 5,770,429; 6,596,541 and 7,049,426.

The phrase "functional fragment or analog" of an antibody is a compound having a qualitative biological activity in common with a full-length antibody. For example, a functional fragment or analog of an anti-TCblR antibody is one that can specifically bind to TCblR. In particular embodiments, it may bind to TCblR with at least 25%, at least 50%, at least 75%, at least 80%, at least 90% or at least 95% of the affinity of the corresponding whole antibody.

An antibody having a "biological characteristic" of a designated antibody is one that possesses one or more of the biological characteristics of that antibody which distinguish it from certain other antibodies. For example, in some embodiments, an antibody with a biological characteristic of a designated antibody will bind the same epitope as that bound by the designated antibody and/or have a common effector function as the designated antibody.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, a TCblR-specific antibody specifically binds to TCblR if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

As used herein, an "antibody variant" comprises one or more amino acid sequence modifications as compared to the wild-type antibody. Such modifications include, for example, deletions from, and/or insertions into and/or substitutions of, one or more residues within the amino acid sequences of the antibody. The amino acid changes also may alter post-translational processes of the antibody, such as changing the number or position of glycosylation sites.

As used herein, an "antibody conjugate" comprises an antibody, or antigen-binding fragment or variant thereof, covalently or non-covalently attached to another agent, such as a label, tag, toxin, chemotherapeutic, or drug. Accordingly, antibody conjugates comprise antibody fusion proteins, including, for example, fusions of an antibody, or an antigen-binding fragment thereof, with enzymes, fluorescent proteins, polypeptide tags, and luminescent markers, as well as chemically associated antibody-agent complexes. As described herein, an agent may be chemically or biosynthetically linked to an anti-TCblR antibody, or antigen-binding fragment thereof. An agent may be directly conjugated to a TCblR antibody or fragment or variant thereof, or it may be conjugated via one or more other molecules, e.g., linkers.

The terms "polypeptide," "protein" and "peptide" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to TCblR of the present disclosure, or sequences that have deletions from, additions to, and/or substitutions of one or more amino acid of an anti-TCblR antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, *Oligonucleotides and Analogues: A Practical Approach*, pp. 87-108 (F. Eckstein, Ed.), Oxford University Press, Oxford England; Stec et al., U.S. Pat. No. 5,151, 510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer a polynucleotide sequence to a host cell. The term "expression vector" refers to a vector that is suitable for transformation of a host cell and contains nucleic acid sequences that direct and/or control expression of inserted nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

The TCblR polypeptide sequence was originally referred to as the 8D6 antigen, or CD320 antigen, prior to its identification as the TCblR. Various transcobalamin receptor polypeptide and polynucleotide sequences are available in NCBI public sequence databases under the following accession numbers: NM_016579, *Homo sapiens* CD320 antigen (CD320), mRNA, gi|51702225|ref|NM_016579.2| [51702225] (SEQ ID NO:49); CR457174, *Homo sapiens* full open reading frame cDNA clone RZPDo834A0912D for gene 8D6A, 8D6 antigen; complete cds, incl. Stop codon, gi|48146464|emb|CR457174.1|[48146464] (SEQ ID NO:50); BC000668, *Homo sapiens* CD320 antigen, mRNA (cDNA clone MGC:828, IMAGE:3347569), complete cds, gi|34784777|gb|BC000668.2|[34784777] (SEQ ID NO:51); BC007083, *Homo sapiens* CD320 antigen, mRNA (cDNA clone MGC:14623, IMAGE:4076237), complete cds, gi|13937942|gb|BC007083.1|[13937942] (SEQ ID NO:52); NT_086894, *Homo sapiens* chromosome 19 genomic contig, alternate assembly, gi|51475033|ref|NT_086894.1|Hs19_86558[51475033]; NT_077812, *Homo sapiens* chromosome 19 genomic contig, gi|37574721|ref|NT_077812.2|Hs19_77861[37574721]; NP_057663, 8D6 antigen [*Homo sapiens*], gi|7706111|ref|NP_057663.1|[7706111] (SEQ ID NO:53); CAG33455, 8D6A [*Homo sapiens*], gi|48146465|emb|CAG33455.1|[48146465]; AAH07083, 8D6 antigen [*Homo sapiens*], gi|13937943|gb|AAH07083.1| [13937943]; AAH00668, 8D6 antigen [*Homo sapiens*], gi|12653765|gb|AAH00668.1|[12653765]; Hs.333427, 8D6A: CD320 antigen, *Homo sapiens*, 297 sequence(s); CD320, Official Symbol: CD320 and Name: CD320 antigen [*Homo sapiens*]Other Aliases: HGNC:16692, 8D6, 8D6AOther Designations: 8D6 antigenChromosome: 19; Location:19p13.3-p13.2GeneID: 51293.

"Carriers" as used herein include pharmaceutically or physiologically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as polysorbate 20 (TWEEN™) polyethylene glycol (PEG), and poloxamers (PLURONICS™), and the like.

As used herein, "treating" or "treatment" refers to an approach for obtaining beneficial or desired results, including and preferably clinical results. Treatment can involve optionally either the amelioration of symptoms of the disease or condition, or the delaying of the progression of the disease or condition.

As used herein, unless the context makes clear otherwise, "prevention," and similar words such as "prevented," "preventing" etc., indicates an approach for preventing, inhibiting, or reducing the likelihood of, the onset or recurrence of a disease or condition. It also refers to preventing, inhibiting, or reducing the likelihood of, the occurrence or recurrence of the symptoms of a disease or condition, or optionally an approach for delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, "inhibiting cell growth" or "inhibiting proliferation of cells" refers to reducing or halting the growth rate of cells. For example, by inhibiting the growth of tumor cells, the rate of increase in size of the tumor may slow. In other embodiments, the tumor may stay the same size or decrease in size, i.e., regress. In particular embodiments, the rate of cell growth or cell proliferation is inhibited by at least 20%, at least 30%, at least 40%, at least 50%, at least 60%, at least 70%, at least 80%, or at least 90%.

A. Antibodies

The present invention includes antibodies that specifically bind to TCblR, and antigen-binding fragments thereof, as described herein. Accordingly, the present invention provides such antibodies, as well as the methods and reagents used to produce them. As will be understood by the skilled artisan, general description of antibodies herein and methods of preparing and using the same also apply to individual antibody polypeptide constituents and antibody fragments.

In certain embodiments of the invention, an antibody, or antigen-binding fragment thereof, that specifically binds to TCblR comprises one or more of the CDR amino acid sequences set forth in SEQ ID NOs:6-8, 14-16, 22-24, 30-32, 38-40 and 46-48. In particular embodiments, an antibody of the invention may comprise 1, 2, 3, 4, 5, or 6 CDRs described herein. In certain aspects, an antibody may comprise 3 VHCDRs described herein. Similarly, an antibody may comprise 3 VLCDRs described herein. Certain antibodies of the invention comprise 6 CDR amino acid sequences described herein.

In one embodiment, an antibody, or antigen-binding fragment thereof, comprises (i) a heavy chain variable region comprising the VHCDR1, VHCDR2 and VHCDR3 amino acid sequences set forth in SEQ ID NOs:6, 7 and 8, respectively, and/or (ii) a light chain variable region comprising a light chain variable region comprising the VLCDR1, VLCDR2 and VLCDR3 amino acid sequences set forth in SEQ ID NOs:14, 15 and 16, respectively. An example of one such antibody is the mAb 1-19 described herein. In another embodiment of the invention, an antibody, or antigen-binding fragment thereof, comprises (i) a heavy chain variable region comprising the VHCDR1, VHCDR2 and VHCDR3 amino acid sequences set forth in SEQ ID NOs:22, 23 and 24, respectively, and/or (ii) a light chain variable region comprising a light chain variable region comprising the VLCDR1, VLCDR2 and VLCDR3 amino acid sequences set forth in SEQ ID NOs:30, 31 and 32, respectively. An example of one such antibody is the mAb 1-23 described herein. In other embodiments, an antibody, or antigen-binding fragment thereof, comprises (i) a heavy chain variable region comprising the VHCDR1, VHCDR2 and VHCDR3 amino acid sequences set forth in SEQ ID NOs:38, 39 and 40, respectively, and/or (ii) a light chain variable region comprising a light chain variable region comprising the VLCDR1, VLCDR2 and VLCDR3 amino acid sequences set forth in SEQ ID NOs:46, 47 and 48, respectively. An example of one such antibody is the mAb 1-25 described herein.

In particular embodiments, the antibody, or antigen-binding fragment thereof, comprises a VH region described herein and 3 VLCDRs described herein. For example, one antibody, or antigen-binding fragment thereof, comprises a VH region comprising the amino acid sequence set forth in SEQ ID NO:5 and a VL region comprising the VLCDR1, VLCDR2 and VLCDR3 amino acid sequences set forth in SEQ ID NOs:14, 15 and 16, respectively. In other embodiments, the antibody, or antigen-binding fragment thereof, comprises a VH region comprising the amino acid sequence set forth in SEQ ID NO:21 and a VL region comprising the VLCDR1, VLCDR2 and VLCDR3 amino acid sequences set forth in SEQ ID NOs:30, 31 and 32, respectively. In certain embodiments, the antibody, or antigen-binding fragment thereof, comprises a VH region comprising the amino acid sequence set forth in SEQ ID NO:37 and a VL region comprising the VLCDR1, VLCDR2 and VLCDR3 amino acid sequences set forth in SEQ ID NOs:46, 47 and 48, respectively. In addition, each of the VH regions described above may be combined with each of the other two VL regions described above in antibodies of the present invention.

In other embodiments, the antibody, or antigen-binding fragment thereof, comprises a VL region described herein and 3 VHCDRs described herein. By way of example, an antibody, or antigen-binding fragment thereof, comprises a VL region comprising the amino acid sequence set forth in SEQ ID NO:13 and a VH region comprising the VHCDR1, VHCDR2 and VHCDR3 amino acid sequences set forth in SEQ ID NOs:6, 7 and 8, respectively. In particular embodiments, the antibody, or antigen-binding fragment thereof, comprises a VL region comprising the amino acid sequence set forth in SEQ ID NO:29 and a VH region comprising the VHCDR1, VHCDR2 and VHCDR3 amino acid sequences set forth in SEQ ID NOs:22, 23 and 24, respectively. In certain embodiments, the antibody, or antigen-binding fragment thereof, comprises a VL region comprising the amino acid sequence set forth in SEQ ID NO:45 and a VH region comprising the VHCDR1, VHCDR2 and VHCDR3 amino acid sequences set forth in SEQ ID NOs:38, 39 and 40, respectively. In addition, each of the VL regions described above may be combined with each of the other two VH regions described above in antibodies of the present invention.

In particular embodiments, the antibody, or antigen-binding fragment thereof, comprises a VH region and a VL region as described herein. Accordingly, in one embodiment, the antibody, or antigen-binding fragment thereof, comprises a VH region comprising the amino acid sequence set forth in SEQ ID NO:5 and a VL region comprising the amino acid sequence set forth in SEQ ID NO:13. In another embodiment, the antibody, or antigen-binding fragment thereof, comprises VH region comprising the amino acid sequence set forth in SEQ ID NO:21 and a VL region comprising the amino acid sequence set forth in SEQ ID NO:29. In one embodiment of the invention, the antibody, or antigen-binding fragment thereof, comprises a VH region comprising the amino acid sequence set forth in SEQ ID NO:37 and a VL region comprising the amino acid sequence set forth in SEQ ID NO:45. In addition, each of the VL regions described above may be combined with each of the other two VH regions described above in antibodies of the present invention.

Antibodies, and antigen-binding fragments thereof, may comprise a VH region as described herein. In particular embodiments, the antibody, or an antigen-binding fragment thereof, comprises a heavy chain variable region comprising the amino acid sequence set forth in one of SEQ ID NOs:5, 21 and 37, or a variant thereof having at least 80%, at least 90%, or at least 95% sequence identity. In certain embodiments, the antibody, or antigen-binding fragment thereof, comprises the heavy chain variable region comprising the amino acid sequence set forth in SEQ ID NO:5 and a light chain variable region which comprises an amino acid sequence having at least 80%, at least 90%, or at least 95% identity to the amino acid sequence set forth in SEQ ID NO:13. In another embodiment, the antibody, or antigen-binding fragment thereof, comprises the heavy chain variable region comprising the amino acid sequence set forth in SEQ ID NO:21 and a light chain variable region which comprises an amino acid sequence having at least 80%, at least 90%, or at least 95% identity to the amino acid sequence set forth in SEQ ID NO:29. In one embodiment, the antibody, or antigen-binding fragment thereof, comprises the heavy chain variable region comprising the amino acid sequence set forth in SEQ ID NO:37 and a light chain variable region which comprises an amino acid sequence having at least 80%, at least 90%, or at least 95% identity to the amino acid sequence set forth in SEQ ID NO:45.

Antibodies, and antigen-binding fragments thereof, may comprise a VL region as described herein. In particular embodiments, the antibody, or an antigen-binding fragment thereof, comprises a light chain variable region comprising the amino acid sequence set forth in one of SEQ ID NOs:13, 29 and 45, or a variant thereof having at least 80%, at least 90%, or at least 95% identity. In certain embodiments, the antibody, or antigen-binding fragment thereof, comprises the light chain variable region comprising the amino acid sequence set forth in SEQ ID NO:13 and a heavy chain variable region which comprises an amino acid sequence having at least 80%, at least 90%, or at least 95% identity to the amino acid sequence set forth in SEQ ID NO:5. In another embodiment, the antibody, or antigen-binding fragment thereof, comprises the light chain variable region comprising the amino acid sequence set forth in SEQ ID NO:29 and a heavy chain variable region which comprises an amino acid sequence having at least 80%, at least 90%, or at least 95% identity to the amino acid sequence set forth in SEQ ID NO:21. In particular embodiments, the antibody, or antigen-binding fragment thereof, comprises the light chain variable region comprises the amino acid sequence set forth in SEQ ID NO:45 and a heavy chain variable region which comprises an amino acid sequence having at least 80%, at least 90%, or at least 95% identity to the amino acid sequence set forth in SEQ ID NO:37.

In some instances, it may be desirable to introduce amino acid modifications or substitutions into one or more CDRs of an anti-TCblR antibody. For instance, the immunogenicity of an antibody may be reduced by substituting one or more amino acids in a CDR (Iwahashi et al., *Mol Immunol.* 36(15-16):1079-1091, 1999). By modifying or substituting one or more amino acids of a CDR, the binding affinity of the antibody for the antigen may also be modulated so that the anti-TCblR antibody has an increased or decreased binding affinity for TCblR in comparison to the unmodified anti-TCblR antibody. In particular embodiments of the invention, an antibody, or antigen-binding fragment thereof, may comprise 1, 2, 3, 4, 5, 6, 7, or 8 amino acid modifications or substitutions in each CDR described herein. Therefore, an anti-TCblR antibody comprising one CDR described herein may have up to 8 amino acid modifications or substitutions in the amino acid sequence of the CDR as set forth herein. Similarly, an anti-TCblR antibody comprising two CDRs described herein may have up to 8 amino acid modifications or substitutions in the amino acid sequences of each of the CDRs as set forth herein, for up to a total of 16 amino acid substitutions. In particular embodiments, an antibody or fragment thereof, e.g., a VH or VL domain, of the present invention comprises at least three CDRs described herein and may comprise a total of 1, 2, 3, 4, 5, 6, 7, or 8 amino acid modifications or substitutions within the CDRs.

Anti-TCblR antibodies according to the present invention also include, but are not limited to, mAb 1-10, mAb 1-18, mAb 1-19, mAb 1-23, mAb 1-25, mAb 2-2, mAb 2-3, mAb 2-4, and mAb 2-6 described herein.

Additionally, an antibody, or antigen-binding fragment thereof, according to the present invention includes an antibody, or an antigen-binding fragment thereof, that competes for binding to TCblR with any one of the antibodies described herein. For example, an antibody may compete for binding to TCblR with any one of mAb 1-10, mAb 1-18, mAb 1-19, mAb 1-23, mAb 1-25, mAb 2-2, mAb 2-3, mAb 2-4, and mAb 2-6. In particular embodiments, an antibody, or antigen-binding fragment thereof, that competes for binding to TCblR binds to an epitope present in residues 64-94, 95-141, 138-141, 150-165, or 184-233 of the TCblR amino acid sequence set forth in SEQ ID NO:53. For example, an antibody that competes for binding with mAb 1-25 may be specific for an epitope present in amino acid residues 150-165 of SEQ ID NO:53. Similarly, an antibody that competes for binding with mAb 1-19 and/or mAb 1-23 may be specific for an epitope present in amino acid residues 184-233 of SEQ ID NO:53.

As used herein, an antibody "competes with" or "competitively inhibits" a reference antibody in binding to a given epitope if it preferentially binds to that epitope to the extent that it blocks, to some degree, binding of the reference antibody to the epitope. Methods known in the art, such as, e.g., competition ELISAs, may be used to determine if an antibody competes with a reference antibody. A competing antibody may inhibit the binding of the reference antibody to a given epitope by at least about 95%, at least about 90%, at least about 85%, at least about 80%, at least about 75%, at least about 70%, at least about 65%, at least about 60%, at least about 55%, or at least about 50%.

1. Generation of TCblR Specific Antibodies

The present invention also includes methods of synthesizing antibodies, and fragments and variants thereof, of the present invention. In certain embodiments, antibodies of the present invention comprising one or more CDRs, VH domains, or VL domains having a sequence disclosed herein may be produced recombinantly, using vectors and methods available in the art, as described further below. For example, polynucleotides encoding variable regions comprising CDRs or having VH or VL sequences described herein may be synthesized using standard techniques and combined with constant regions to generate polynucleotide sequences encoding heavy and light chains comprising one or more CDRs, VH and/or VL regions having a sequence described herein. The polynucleotide sequences encoding these heavy and light chains can be cloned into a suitable expression vector known in the art and transfected into a suitable host cell (e.g., mammalian cells, yeast cells, bacteria) to secrete antibody into the culture supernatant. The recombinant antibody can be isolated by various methods such as affinity chromatography.

As noted above, in certain embodiments, a TCblR-binding antibody comprises one or more of the CDRs, VH domains, or VL domains of the antibodies described herein, including any of the various combinations described above. In this regard, it has been shown in some cases that the transfer of only the VHCDR3 of an antibody can be performed, while still retaining desired specific binding (Barbas et al., PNAS (1995) 92: 2529-2533). See also, McLane et al., PNAS (1995) 92:5214-5218, Barbas et al., J. Am. Chem. Soc. (1994) 116:2161-2162.

Marks et al. (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds TCblR. The repertoire may then be displayed in a suitable host system such as the phage display system of PCT Publication No. WO 92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences described herein using random mutagenesis of one or more selected VH and/or VL genes to generate mutations within the entire variable domain. Such a technique is described by Gram et al. (1992, Proc. Natl. Acad. Sci. USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci. USA, 91:3809-3813) and Schier et al. (1996, J. Mol. Biol. 263:551-567).

In certain embodiments, a specific VH and/or VL region having a sequence described herein may be used to screen a library of the complementary variable domain to identify antibodies with desirable properties, such as increased affinity for TCblR. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to TCblR. For example: Klimka et al., British Journal of Cancer (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al. above.

These just-described techniques are, in and of themselves, known as such in the art. The skilled person will, however, be able to use such techniques to obtain antibodies or antigen-binding fragments thereof comprising one or more CDR, VH and/or VL sequences described herein, using routine methodology in the art. These sequences may also be modified using recombinant molecular biology techniques to generate variants of antibodies having sequences described herein.

In other embodiments, antibodies other than those having CDR, VH or VL sequences defined herein, but which bind an antigenic region or epitope of TCblR described herein, may be desired. The present invention also includes methods of generating such other antibodies that specifically bind to antigenic regions or epitopes of TCblR described herein, including the regions and epitopes of TCblR bound by the antibodies described in the accompanying Examples, such as the regions and epitopes depicted in Table 1 and described in Examples 1 and 5. In certain embodiments, these methods comprise immunizing an animal with a recombinant antigenic TCblR polypeptide region or epitope of TCblR described herein. Other methods of production include generating ascites by injecting hybridoma cells into the peritoneal cavity of an animal (e.g., mice), transgenic animals that secrete the antibody into milk or eggs, and transgenic plants that make antibody in the fruit, roots or leaves.

As set forth in the Examples below, the two LDLR-A domains of TCblR are involved in ligand binding. In particular, the first LDLR-A domain and the C-terminus of the second LDLR-A domain were demonstrated to be essential for TC-Cbl binding. The C-terminus of the second LDLR-A domain (amino acid residues 138-165 of human TCblR set forth in SEQ ID NO:53) and the N-terminus of the first LDLR-A domain (amino acid residues 53-63 of human TCblR set forth in SEQ ID NO:53) are important determinants of TC-Cbl binding, since deleting or mutating these regions abrogated TC-Cbl binding. Specifically, mutating critical amino acids in C-terminus of the two LDLR-A domains in mutants D85L, E86L and D163L, E164L eliminated TC-Cbl binding to the receptor. The critical role of these amino acids in $Ca^{++}$ binding is further evident from the recently identified CD320 gene defect of a single amino acid deletion (del E) in the first LDLR-A domain, resulting in decreased uptake of TC-Cbl and methyl malonic acidemia in a new born (Quadros et al., (2010) Hum Mutat 31:924-929). The $Ca^{++}$ requirement for binding dictates that integrity of LDLR-A module conformation with $Ca^{++}$ ion in position is necessary for ligand binding (Fass et al., (1997) Nature 388: 691-693).

In certain embodiments, an antibody of the invention binds an epitope present in or near an LDLR-A domain. For example, an antibody may bind an epitope present in amino acid residues 54-89 or 132-167 of human TCblR set forth in SEQ ID NO:53. In certain embodiments, the antibody recognizes an epitope in residues 53-63 of human TCblR set forth in SEQ ID NO:53. In another embodiment, the antibody recognizes an epitope comprising residue 85 of human TCblR set forth in SEQ ID NO:53. In yet another embodiment, the antibody recognizes an epitope comprising residue 86 of human TCblR set forth in SEQ ID NO:53. In another embodiment, the antibody recognizes an epitope present in amino acid residues 138-165 of human TCblR set forth in SEQ ID NO:53. In yet another embodiment, the antibody recognizes an epitope present in amino acid residues 150-165 of human TCblR set forth in SEQ ID NO:53. In another embodiment, the antibody recognizes an epitope comprising residue 163 of human TCblR set forth in SEQ ID NO:53. In yet another embodiment, the antibody recognizes an epitope comprising residue 164 of human TCblR set forth in SEQ ID NO:53. In particular embodiments, the antibody is a blocking antibody. Additional antibodies that bind to one or more of these regions or epitope of TCblR may be generated, including monoclonal and polyclonal antibodies, by using these regions of TCblR as the immunogen in techniques described herein.

Methods of producing such polyclonal and monoclonal antibodies are known in the art and described generally, e.g., in U.S. Pat. No. 6,824,780 and Harlow and Lane, *Antibodies: A Laboratory Manual*, Cold Spring Harbor Laboratory, 1988. In one such technique, the immunogen is initially injected into a suitable animal (e.g., mice, rats, rabbits, sheep and goats), preferably according to a predetermined schedule incorporating one or more booster immunizations. To increase immunogenicity, an immunogen may be linked to, for example, glutaraldehyde or keyhole limpet hemocyanin (KLH). Following injection, the animals are bled periodically to obtain post-immune serum containing polyclonal anti-TCblR antibodies. Polyclonal antibodies may then be purified from such antisera by, for example, affinity chromatography using a TCblR polypeptide or antigenic portion thereof coupled to a suitable solid support. Such polyclonal antibodies may be used directly, e.g., for screening purposes and Western blots.

Such additional monoclonal antibodies and competing antibodies may be prepared, for example, using the technique of Kohler and Milstein, *Eur. J. Immunol.* 6:511-519, 1976, and improvements thereto. Briefly, these methods involve the preparation of immortal cell lines (i.e., hybridomas) capable of producing antibodies having the desired specificity (i.e., reactivity with the polypeptide of interest). Hybridoma cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Antigen-specific repertoires can be recovered from immunized animals by hybridoma technology as described above, single-cell RT-PCR for selected B cells, antibody display technologies, and other methods known in the art. For example, to recover mAbs from mouse-derived hybridomas, antibodies would be secreted into the culture supernatant and can be isolated by means known in the art such as ammonium sulfate precipitation and column chromatography using protein A, protein G, etc. Such isolated antibody can be used for further testing and characterization of the antibody to determine potency in vitro and in vivo, affinity, etc.

As described above, an antibody, or antigen-binding fragment thereof, according to the present invention may be an antibody or an antigen-binding fragment that is specific for an epitope of TCblR such that it competes for binding to TCblR with one of the antibodies described herein. For example, an antibody may compete with a disclosed antibody for binding to an epitope present in amino acid residues 54-89 or 132-167 of SEQ ID NO:53. In addition, a blocking antibody, or antigen-binding fragment thereof, may compete for binding with another blocking antibody. One example of a blocking antibody is an antibody that competes with mAb 1-25 for binding to TCblR is specific for an epitope present in amino acid residues 150-165 of SEQ ID NO:53. Such antibodies may be identified by performing competition assays.

In particular embodiments, antibodies of the present invention are humanized or fully human antibodies. Humanized antibodies of the present invention, including those comprising one or more CDR, VH, or VL region having a sequence described herein may be recombinantly produced by cloning a polynucleotide sequence encoding a region of said antibody, or fragment thereof, comprising said CDRs, VL and/or VH regions into a polynucleotide sequence comprising the remaining regions of a human heavy or light chain. In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some framework residues are substituted by residues from analogous sites in rodent antibodies.

It is important that chimeric antibodies retain high binding affinity for the antigen and other favorable biological properties. To achieve this goal, according to one method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies may be generated against antigenic regions or epitopes of TCblR by in vitro activated B cells (see U.S. Pat. Nos. 5,567,610 and 5,229,275). In addition, such human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,545,807; 5,569,825; 5,591,669; 5,770,429; 6,596,541 and 7,049,426; and PCT Publication No. WO 97/17852. Such animals may be genetically engineered to produce human antibodies comprising a polypeptide of the present invention.

As noted above, antibodies (i.e., immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In various embodiments, antibodies of the present invention, and fragments thereof, comprise a variable light chain that is either kappa or lambda. The lambda chain may be of any subtype, including, e.g., lambda 1, lambda 2, lambda 3, and lambda 4.

2. Antigen-Binding Fragments

As noted above, the present invention further provides antibody fragments comprising a fragment of an antibody described herein, e.g., a fragment that confers antigen specificity to the antibody. Examples of antibody fragments of the present invention include: Fab, Fab', F(ab')$_2$ and Fv fragments; diabodies; linear antibodies; single-chain antibodies; and multispecific antibodies formed from antibody fragments. In related embodiments, antibody fragments of the present invention are polypeptides comprising a portion of an antibody of the present invention, e.g., a polypeptide comprising one or more variable domains or hypervariable regions or CDRs of an antibody described herein. Preferably, antibody fragments of the present invention specifically bind or selectively bind to TCblR.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can be produced directly by recombinant host cells. Fab, Fv and scFv antibody fragments can all be expressed in and secreted from *E. coli*, thus allowing the facile production of large amounts of these fragments. Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody is a single chain Fv fragment (scFv). See PCT Publication No. WO 93/16185; U.S. Pat. Nos. 5,571,894; and 5,587,458. Fv and scFv are the only species with intact combining sites that are devoid of constant regions. scFv fusion proteins may be constructed to yield fusion of an effector protein at either the amino or the carboxy terminus of an sFv. See Antibody Engineering, ed. Borrebaeck, supra.

The antibody fragment may also be a "linear antibody", e.g., as described in U.S. Pat. No. 5,641,870. Such linear antibody fragments may be monospecific or bispecific.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Bispecific antibodies can be prepared as full length antibodies or antibody fragments (e.g., F(ab')$_2$ bispecific antibodies). PCT Publication No. WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in PCT Publication No. WO 98/02463. U.S. Pat. No. 5,821,337 teaches a bispecific anti-ErbB2/anti-CD3 antibody.

3. Antibody Variants

Variants of the antibodies and fragments thereof described herein are also contemplated by the present invention, which variants comprise one or more amino acid sequence modification(s) as compared to the wild-type antibody, or fragment thereof. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of one or more deletions, insertions, and substitutions may be made to arrive at the final antibody, provided that the final construct possesses the desired characteristics (e.g., binding TCblR). The amino acid changes also may alter post-translational processes of the antibody, such as changing the number or position of glycosylation sites. Any of the variations and modifications described herein may be included in antibodies of the present invention. In particular embodiments, a variant of an antibody or fragment described herein has at least 90% or at least 95% sequence identity as compared to the wild-type antibody or fragment. In certain embodiments, the CDRs are unmodified with respect to the wild-type antibody or fragment. In other embodiments, one or more CDRs comprise 1, 2, 3, 4, 5, 6, 7, or 8 modified residues with respect to the wild-type antibody or fragment.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res*, 25: 3389-3402). When utilizing BLAST and Gapped BLAST programs, the default parameters of the respective programs (e.g., XBLAST and NBLAST) can be used.

Also disclosed herein is a method for obtaining an antibody antigen binding member specific for TCblR, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for TCblR and optionally with one or more desired properties. The VL domains may have an amino acid sequence which is substantially as set out herein. An analogous method may be employed in which one or more sequence variants of a VL domain disclosed herein are combined with one or more VH domains.

A useful method for identification of certain residues or regions of an antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions may include amino- and/or carboxyl-terminal fusions ranging in length from one residue to polypeptides containing a hundred or more residues, as well as intrasequence insertions of single or multiple amino acid residues. Examples of insertional variants of an antibody include the fusion of the N- or C-terminus of the antibody to a polypeptide that increases the serum half-life of the antibody.

One type of variant is an amino acid substitution variant. These variants have at least one amino acid residue in the antibody molecule or fragment thereof replaced by a different residue. The sites of greatest interest for substitutional mutagenesis include the hypervariable or CDR regions, but framework (FR) alterations are also contemplated. Conservative and non-conservative substitutions are contemplated.

Substantial modifications in the binding and/or biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved binding or biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein, and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The present disclosure provides variants of the antibodies disclosed herein. In certain embodiments, such variant antibodies or antigen-binding fragments, or CDRs thereof, bind to TCblR at least about 50%, at least about 70%, and in certain embodiments, at least about 90% as well as an antibody or fragment thereof specifically set forth herein. In further embodiments, such variant antibodies or antigen-binding fragments, or CDRs thereof, bind to TCblR with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable domain having an amino acid sequence that is at least 80% identical, at least 95% identical, at least 90%, at least 95% or at least 98% or 99% identical, to the heavy chain variable region of an anti-TCblR antibody described herein; and/or b) a light chain variable region having an amino acid sequence that is at least 80% identical, at least 85%, at least 90%, at least 95% or at least 98% or 99% identical, to the light chain variable domain of an anti-TCblR antibody described herein. The amino acid sequence of illustrative heavy and light chain regions are set forth in SEQ ID NOs:5, 13, 21, 29, 37 and 45.

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of a selected antibody described herein; and/or iii. a CDR3 region that is identical in amino acid sequence to the heavy chain CDR3 region of a selected antibody as described herein; and/or b) a light chain variable domain comprising: i. a CDR1 region that is identical in amino acid sequence to the light chain CDR1 region of a selected antibody described herein; ii. a CDR2 region that is identical in amino acid sequence to the light chain CDR2 region of a selected antibody described herein; and/or iii. a CDR3 region that is identical in amino acid sequence to the light chain CDR3 region of a selected antibody described herein; wherein the antibody specifically binds a selected target (e.g., TCblR). In a further embodiment, the antibody, or antigen-binding fragment thereof, is a variant antibody wherein the variant comprises a heavy and light chain identical to the selected antibody except for up to 8, 9, 10, 11, 12, 13, 14, 15, 16 or more amino acid substitutions in the CDR regions of the VH and VL regions. In this regard, there may be 1, 2, 3, 4, 5, 6, 7, 8, or in certain embodiments, 9, 10, 11, 12, 13, 14, 15, 16 or more amino acid substitutions in the CDR regions of a selected antibody. Substitutions may be in CDRs either in the VH and/or the VL regions. (See e.g., Muller, 1998, *Structure* 6:1153-1167).

In particular embodiments, the antibody comprises a heavy chain variable region comprising the VHCDR1, VHCDR2 and VHCDR3 amino acid sequences set forth in SEQ ID NOs:6, 7 and 8, respectively. In other embodiments, the antibody comprises a light chain variable region comprising a light chain variable region comprising the VLCDR1, VLCDR2 and VLCDR3 amino acid sequences set forth in SEQ ID NOs:14, 15 and 16, respectively. In certain embodiments, the antibody comprises (i) a heavy chain variable region comprising the VHCDR1, VHCDR2 and VHCDR3 amino acid sequences set forth in SEQ ID NOs:6, 7 and 8, respectively, and (ii) a light chain variable region comprising a light chain variable region comprising the VLCDR1, VLCDR2 and VLCDR3 amino acid sequences set forth in SEQ ID NOs:14, 15 and 16, respectively.

In particular embodiments, the antibody comprises a heavy chain variable region comprising the VHCDR1, VHCDR2 and VHCDR3 amino acid sequences set forth in SEQ ID NOs: 22, 23 and 24, respectively. In other embodiments, the antibody comprises a light chain variable region comprising a light chain variable region comprising the VLCDR1, VLCDR2 and VLCDR3 amino acid sequences set forth in SEQ ID NOs: 30, 31 and 32, respectively. In certain embodiments, the antibody comprises (i) a heavy chain variable region comprising the VHCDR1, VHCDR2 and VHCDR3 amino acid sequences set forth in SEQ ID NOs:22, 23 and 24, respectively, and/or (ii) a light chain variable region comprising a light chain variable region comprising the VLCDR1, VLCDR2 and VLCDR3 amino acid sequences set forth in SEQ ID NOs:30, 31 and 32, respectively In particular embodiments, the antibody comprises a heavy chain variable region comprising the VHCDR1, VHCDR2 and VHCDR3 amino acid sequences set forth in SEQ ID NOs: 38, 39 and 40, respectively. In other embodiments, the antibody comprises a light chain variable region comprising a light chain variable region comprising the VLCDR1, VLCDR2 and VLCDR3 amino acid sequences set forth in SEQ ID NOs: 46, 47 and 48, respectively. In certain embodiments, the antibody comprises (i) a heavy chain variable region comprising the VHCDR1, VHCDR2 and VHCDR3 amino acid sequences set forth in SEQ ID NOs:38, 39 and 40, respectively, and/or (ii) a light chain variable region comprising a light chain variable region comprising the VLCDR1, VLCDR2 and VLCDR3 amino acid sequences set forth in SEQ ID NOs:46, 47 and 48, respectively Determination of the three-dimensional structures of representative polypeptides (e.g., variant TCblR-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 Prot. Sci. 3:2378; Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007); Raman et al. Science 327:1014-1018 (2010). Some additional non-limiting examples of computer algorithms that may be used for these and related embodiments, such as for rational design of TCblR-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) J. Comput. Chem. 4:187-217) and AMBER (Weiner et al. (1981) J. Comput. Chem. 106: 765), which assess force field calculations, and analysis (see also, Eisenfield et al. (1991) Am. J. Physiol. 261:C376-386; Lybrand (1991) J. Pharm. Belg. 46:49-54; Froimowitz (1990) Biotechniques 8:640-644; Burbam et al. (1990) Proteins 7:99-111; Pedersen (1985) Environ. Health Perspect. 61:185-190; and Kini et al. (1991) J. Biomol. Struct. Dyn. 9:475-488). A variety of appropriate computational computer programs are also commercially available, such as from Schrödinger (Munich, Germany).

In certain embodiments, the present invention includes a method of producing a human or humanized antibody light chain or heavy chain, or fragment thereof, by recombinantly introducing one or more CDRs described herein into a polynucleotide encoding a human antibody light chain or heavy chain, or fragment thereof. For example, one, two, or three CDRs of the light or heavy chain of a monoclonal antibody described herein may be substituted into a human antibody light chain or heavy chain using recombinant biology techniques known and available in the art. The resulting polynucleotide may be present in an expression vector or subcloned into an expression vector, and the expression vector may be present in or introduced into a cell suitable for recombinant expression of the encoded polypeptide. The cell may be cultured under conditions suitable for the expression of the polypeptide, which may be obtained from the cell using standard techniques. In particular embodiments, a light chain and a heavy chain may be expressed in the same cell, whereas in other embodiments, they may be expressed in different cells, and optionally combined later to produce an antibody or fragment thereof comprising both heavy chain and light chain sequences (or fragments thereof). In certain embodiments, the resulting light chain or heavy chain (or fragment thereof) comprises a human framework and one, two or three CDRs described herein. In specific embodiments, the human or humanized antibody or chain (or fragments thereof) comprise all three CDRs present in either a light chain or heavy chain of a monoclonal antibody described here, such as mAb1-19, mAb 1-23, or mAb 1-25.

4. Antibody Conjugates

Antibodies of the present invention (and antigen-binding fragments and variants thereof) may also be modified to include an agent, such as an epitope tag, label, toxin, chemotherapeutic, or drug, e.g., for use in purification, diagnostic or treatment applications. In particular embodiments, the agent is bound to the antibody either directly or indirectly (e.g., via a linker), and the agent may be bound either covalently or non-covalently. In particular embodiments, the agent is bound to the antibody exclusively via one or more covalent bonds, either directly or via a linker, i.e., the agent is bound to the antibody or fragment thereof only via one or more covalent bonds. For example, in certain embodiments, an agent is bound to a linker via one or more covalent bonds, and said linker is also bound to an antibody or fragment thereof of the present invention via one or more covalent bonds. In addition, one or more, e.g., two, three, four or more, same or different agents may be bound to a single antibody or fragment thereof described herein. Examples of non-covalent bonds include hydrogen bonds, ionic bonds, van der Waals forces, and hydrophobic interactions. A covalent bond is a form of chemical bonding that is characterized by the sharing of pairs of electrons between atoms, and other covalent bonds. Covalent bonding includes many kinds of interaction, including σ-bonding, π-bonding, metal to metal bonding, agostic interactions, and three-center two-electron bonds There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). Examples of useful linking groups include disulfide groups, thioether groups, acid labile groups, photolabile groups, peptidase labile groups, or esterase labile groups, as disclosed in the above-identified patents. Linkers and conjugation methods are also disclosed in U.S. Pat. Nos. 7,964,567, 7,964,566, 7,851,437, 7,837,980, 7,754,681, and 7,256,257.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

A bifunctional protein coupling agent may be a homobifunctional or heterobifunctional crosslinker. Homobifunctional crosslinkers include, e.g., amine-specific protein linkers based on N-hydroxysuccinimide ester and imidoester reactive groups for the selective conjugation of primary amines. Examples of heterobifunctional crosslinkers include, e.g., carbodiimide crosslinking reagents (e.g., dicyclohexylcarbodiimide and 1-Ethyl-3-[3-dimethylaminopropyl]carbodiimide hydrochloride) for conjugation of carboxyl groups (e.g., glutamate, aspartate, C-termini) to primary amines (lysine, N-termini). Reagents such as N-hydroxysuccinimide can be used for convert a carboxyl to an amine-reactive N-hydroxysuccinimide ester for amine-conjugation. Bifunctional crosslinkers are available in a variety of lengths and may be cleavable, irreversible, or membrane permeable.

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. Methods of linking such agents to proteins, such as antibodies, are known in the art and described, e.g., in U.S. Pat. No. 7,632,492.

Examples of detectable labels which may be conjugated to antibodies of the present invention include fluorescent labels, enzyme labels, radioisotopes, chemiluminescent labels, electrochemiluminescent labels, bioluminescent labels, polymers, polymer particles, metal particles, haptens, and dyes. Detectable labels include imaging compounds that are useful in diagnostic imaging.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), α-naphtol pyronin (α-NP), o-dianisidine (OD), 5-bromo-4-chloro-3-indolylphosp-hate (BLIP), Nitro blue tetrazolium (NBT), 2-(p-iodophenyl)-3-p-nitropheny-l-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

In addition to detection or imaging labels, the subject antibodies, and antigen-binding fragments thereof, may be conjugated to a cytotoxin, or cytotoxic agent. Cytotoxins include biotoxins, chemotherapeutics, and radioisotopes useful in the treatment of a tumor, cancer or proliferative disease or disorder associated with an increased expression of TCblR as compared to quiescent or normal cells. As used herein, a "toxin," "cytotoxic agent" or "cytostatic agent" refers to an agent that decreases the growth or proliferation rate of a cell and/or causes cell death. Examples of toxins and anti-cancer agents include, but are not limited to, 5-fluorouracil, abrin A chain, actinomycin D, adriamycin, aminopterin, anthracycline, arabinoside, auristatins, bleomycin, busulfan, calicheamicin, carboplatin, caminomycin, carmustine, chlorambucil, colchicin, cholera toxin, cisplatin, crotin, curcin, cyclophosphamide, cytarabine, cytochalasin B, cytosine, cytosine arabinoside, cytotoxic nucleosides, cytoxin, dactinomycin, daunomycin, dichloromethotrexate, dihydroxy anthracin dione, diphtheria A chain, diphtheria toxin, dolastatin 10, doxetaxel, doxil, doxorubicin, emetine, enomycin, epirubicin, esperamicin, ethidium bromide, etoposide, exotoxin A chain, fioxuridine, ftorafur, gelonin, gramicidin D, ifosfamide, leurosidine, leurosine, lidocaine, lomustine, mechlorethamine, melphalan, mercaptopurine, methopterin, methotrexate, mithramycin, mitomycin, mitomycin C, mitoxantrone, paclitaxel, phenomycin, podophyllotoxin, porfiromycin, procaine, propranolol, pseudomonas exotoxin, puromycin radioactive isotopes (e.g., $1^{125}$, $I^{131}$, $Y^{90}$, $Re^{186}$, and $Bi^{212}$), ricin A chain, saporin, semustine, streptonigrin, taxane, taxoids, taxol, teniposide, tetracaine, thiotepa, toxotere, triaziquone, triethylenephosphoramide, vinblastine, vincristine, vindesine, and vinorelbine. In particular embodiments, the toxin is selected from ricin A chain, gelonin, saporin, cholera toxin, diphtheria toxin, and pseudomonas exotoxin.

In certain embodiments, a conjugate of an antibody (or fragment thereof) of the present invention and a toxin (such as saporin) has an IC50 for inhibiting cell growth of 500 pM or less, 400 pM or less, 300 pM or less, 200 pM or less, or 100 pM or less. In certain embodiments, an antibody-toxin conjugate has an IC50 of about 500-100 pM, about 400-100 pM, about 300-100 pM, or about 200-100 pM. Similarly, in certain embodiments, a combination of an anti-TCblR antibody (or fragment thereof) of the present invention and a secondary antibody conjugated to a toxin (such as saporin) has an IC50 for inhibiting cell growth of 500 pM or less, 400 pM or less, 300 pM or less, 200 pM or less, or 100 pM or less. In certain embodiments, an anti-TCblR antibody and a secondary antibody-toxin conjugate combination has an IC50 of about 500-100 pM, about 400-100 pM, about 300-100 pM, or about 200-100 pM. In certain embodiments, the IC50 is determined with respect to a tumor cell line, such as HEK293 cells, and/or under conditions described in Example 4.

In certain embodiments, a primary anti-TCblR antibody is used in combination with a secondary antibody conjugated to a toxin (e.g., saporin) as described, for example, in Example 2. The primary antibody to secondary antibody may be used at a ratio of 1:1, 1:2, 1:3, 1:4, 1:5, 1:6, 1:7, or 1:8. In certain embodiments, the ratio of primary antibody to secondary antibody is from 1:1 to 1:8. In certain embodiments, the ratio of primary antibody to secondary antibody is from 1:2 to 1:6.

In particular embodiments, the ratio of primary antibody to secondary antibody is 1:4. The concentration of primary antibody may range from 0.078 nM to 80 nM. In certain embodiments the concentration of the primary antibody is 1 nM to 10 nM. In certain embodiments, the concentration of primary antibody ranges from 2 nM to 5 naM. In particular embodiments, the concentration of the primary antibody is 2.5 nM. In certain embodiments, the concentration of the secondary antibody is in the range of 5 nM to 40 nM. In certain embodiments, the concentration of secondary antibody is in the range of 10 nM to 40 nM. In particular embodiments, the concentration of the secondary antibody is 10 nM. In certain embodiments, the primary antibody to secondary antibody ratio is determined by titrating the antibodies and measuring the effect on viability of a tumor cell line, such as SW48 cells and K562 cells, and/or under conditions described in Example 2.

In certain embodiments, an anti-TCblR antibody conjugated to a toxin (e.g., saporin) as described, for example, in Example 4. In some embodiments, the anti-TCblR antibody-toxin conjugate is used at a concentration of 0.156 nM to 10 nM. In certain embodiments, the anti-TCblR antibody-toxin conjugate is used at a concentration of 2.5 nM to 5 nM. In particular embodiments, the anti-TCblR antibody-toxin conjugate is used at a concentration of 2.5 nM.

The various agents described herein may be linked to the antibodies described herein or to any other molecule that specifically binds to a biological marker of interest, e.g., an antibody, a nucleic acid probe, or a polymer. Furthermore, one of ordinary skill in the art would appreciate that agents can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, *Immunocytochemistry: Theory and Practice*, (CRC Press, Boca Raton, Fla.); *Methods in Molecular Biology*, vol. 80 1998, John D. Pound (ed.) (Humana Press, Totowa, N.J.).

5. Polynucleotides and Polypeptides

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies, and fragments and variants thereof, that bind TCblR as described herein, or that compete with an antibody, or fragment or variant thereof, described herein for binding to TCblR.

Therefore, according to these and related embodiments, the present disclosure also provides polynucleotides encoding the anti-TCblR antibodies, fragments, and variants described herein. In certain embodiments, polynucleotides are provided that comprise some or all of a polynucleotide sequence encoding an antibody, or fragment or variant thereof, as described herein and complements of such polynucleotides.

In other related embodiments, polynucleotide variants may have substantial identity to a polynucleotide sequence encoding an anti-TCblR antibody, or fragment or variant thereof, described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody, or fragment or variant thereof, described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000; and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind TCblR, or antigen-binding fragments thereof. In other embodiments, such polynucleotides encode antibodies or antigen-binding fragments, or CDRs thereof, that bind to TCblR at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to TCblR with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant TCblR-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5,000, about 3,000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encode antibodies that bind to TCblR. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment or variant thereof, to alter one or more properties of the encoded polypeptide, such as the binding affinity of the antibody or the antigen-binding fragment or variant thereof, or the function of a particular Fc region, or the affinity of the Fc region for a particular FcγR. The techniques of site-specific mutagenesis are well known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially available and their use is generally well known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

According to certain related embodiments there is provided a recombinant host cell which comprises one or more constructs as described herein; a nucleic acid encoding any antibody, CDR, VH or VL domain, or antigen-binding fragment thereof, described herein; and a method of production of the encoded product, which method comprises expression from the encoding nucleic acid therefore. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antigen-binding fragments in prokaryotic cells such as *E. coli* is well established in the art. For a review, see for example Pluckthun, A. *Bio/Technology* 9: 545-551 (1991). Expression in eukaryotic cells in culture is also available to those skilled in the art as an option for production of antibodies or antigen-binding fragments thereof, see recent reviews, for example Ref, M. E. (1993) *Curr. Opinion Biotech.* 4: 573-576; Trill J. J. et al. (1995) *Curr. Opinion Biotech* 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences that promote recombination with the genome, in accordance—with standard techniques.

The present invention also provides, in certain embodiments, a method that comprises using a construct as stated above in an expression system in order to express a particular polypeptide such as a TCblR-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, *Molecular Cloning, a Laboratory Manual*, Cold Spring Harbor Laboratories; Davis et al., 1986, *Basic Methods in Molecular Biology*, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The present invention further provides in certain embodiments an isolated polypeptide comprising an antibody chain or a fragment or variant thereof as described herein, for instance, a polypeptide comprising a CDR or VH or VL domain as described herein.

In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-TCblR antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (SEQ ID NO:54) (Chaudhary et al., 1990, *Proc. Natl. Acad. Sci. U.S.A.* 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:55) (Bird et al., 1988, *Science* 242:423-426).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO:56) repeated 1 to 3 times. Such a spacer has been used in constructing single chain antibodies (scFv) by being inserted between VH and VL (Bird et al., 1988, *Science* 242:423-426; Huston et al., 1988, *Proc. Natl. Acad. Sci. U.S.A.* 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

6. Screening Methods

The invention further provides methods of identifying and producing antibodies and fragments thereof, including antibodies and fragments thereof capable of delivering an agent to a cell expressing TCblR and antibodies and fragments thereof capable of inhibiting cobalamin uptake by a cell expressing TCblR. In particular embodiments, these methods are based upon identifying antibodies and fragments thereof that bind to the same regions or epitopes of TCblR as the antibodies described therein. In particular embodiments, the antibodies and fragments thereof bind to one or more regions of TCblR described in Table 1.

In general, the antibodies and fragments thereof are identified by screening candidates for their ability to bind a TCblR polypeptide or fragment thereof in vitro or in vivo, or cells that express a TCblR polypeptide or fragment thereof, e.g., a recombinantly introduced TCblR polypeptide or fragment thereof. Any assay suitable for determining binding of an antibody or fragment thereof to a polypeptide or cell may be used, and a variety of such assays are known and available in the art.

Candidate antibodies and fragments thereof may be screened individually, e.g., when a specific molecule is predicted to function as an inhibitor or inducer/activator. Alternatively, a library of antibodies or fragments thereof may be screened, such as phage display libraries expressing antibodies or fragments thereof (including aptamers).

In certain embodiments, a method of identifying an antibody or fragment thereof that binds a cell that expresses TCblR comprises: contacting a candidate antibody or fragment thereof with a first polypeptide comprising or consisting of the extracellular domain of TCblR, or a region thereof capable of binding an antibody or fragment thereof comprising: (1) a VH region comprising the amino acid sequence set forth in SEQ ID NO:37 and a VL region comprising the amino acid sequence set forth in SEQ ID NO:45; (2) a VH region comprising the amino acid sequence set forth in SEQ ID NO:5 and a VL region comprising the amino acid sequence set forth in SEQ ID NO:13; or (3) a VH region comprising the amino acid sequence set forth in SEQ ID NO:21 and a VL region comprising the amino acid sequence set forth in SEQ ID NO:29; determining a first amount of binding of the candidate antibody or fragment thereof to the first polypeptide; contacting the candidate antibody or fragment thereof with a control or unrelated polypeptide; and determining a second amount of binding of the candidate to the control or unrelated polypeptide, wherein if the first amount of binding to the candidate antibody or fragment thereof is greater than the second amount of binding to the candidate antibody or fragment thereof, said candidate antibody or fragment thereof inhibits cobalamin uptake by a cell that expresses TCblR.

In certain embodiments of various methods herein, a control polypeptide comprises or consists of the extracellular domain of TCblR, or a region thereof capable of binding said antibody or fragment thereof, wherein one or more amino acid residues of the TCblR polypeptide or region thereof is mutated such that the control polypeptide or fragment thereof has a reduced ability to bind said antibody or fragment thereof. In particular embodiments, the second polypeptide comprises one or more amino acid substitutions, deletions, or insertions within one or more LDLR-A domain of TCblR. In particular, the control polypeptide may comprise one or more amino acid substitutions, deletions, or insertions within a region of TCblR selected from the group consisting of: amino acid residues 54-89, amino acid residues 132-167, amino acid residues 53-63, amino acid residue 85, amino acid residue 86, amino acid residues 150-167, amino acid residue 163, and amino acid residue 164, of SEQ ID NO:53. In other embodiments, a control or unrelated polypeptide is a polypeptide that is not specifically bound by an antibody of the present invention, e.g., it is not specifically bound by mAb 1-19, mAb 1-23, or mAb 1-25.

In certain embodiments, a method of identifying an antibody or fragment thereof that inhibits cobalamin uptake by a cell that expresses TCblR comprises: contacting a candidate antibody or fragment thereof with a first polypeptide comprising or consisting of the extracellular domain of TCblR, or a region thereof, capable of binding an antibody or fragment thereof comprising a VH region comprising the amino acid sequence set forth in SEQ ID NO:37 and a VL region comprising the amino acid sequence set forth in SEQ ID NO:45; determining a first amount of binding of the candidate antibody or fragment thereof to the first polypeptide; contacting the candidate antibody or fragment thereof with a control or unrelated polypeptide; and determining a second amount of binding of the candidate antibody or fragment thereof to the control or unrelated polypeptide, wherein if the first amount of binding to the candidate antibody or fragment thereof is greater than the second amount of binding to the candidate antibody or fragment thereof, said candidate antibody or fragment thereof inhibits cobalamin uptake by a cell that expresses TCblR.

In related embodiments, a method of identifying an antibody or fragment thereof that inhibits cobalamin uptake by a cell that expresses TCblR comprises: contacting a candidate antibody or fragment thereof with a first cell or population of cells that expresses a first polypeptide comprising the extracellular domain of TCblR, or a region thereof, capable of binding an antibody or fragment thereof comprising a VH region comprising the amino acid sequence set forth in SEQ ID NO:37 and a VL region comprising the amino acid sequence set forth in SEQ ID NO:45; determining a first amount of binding of the candidate antibody or fragment thereof to the first cell or population of cells; contacting the candidate antibody or fragment thereof with a second cell or population of cells that expresses a control or unrelated polypeptide; and determining a second amount of binding of the candidate antibody or fragment thereof to the second cell, wherein if the first amount of binding to the candidate antibody or fragment thereof is greater than the second amount of binding to the candidate antibody or fragment thereof, said candidate antibody or fragment thereof inhibits cobalamin uptake by a cell that expresses TCblR.

In other embodiments, a method of identifying an antibody or fragment thereof that inhibits cobalamin uptake by a cell that expresses TCblR comprises: contacting a candidate antibody or fragment thereof with a polypeptide comprising or consisting of a region of TCblR capable of binding an antibody or fragment thereof comprising a VH region comprising the amino acid sequence set forth in SEQ ID NO:37 and a VL region comprising the amino acid sequence set forth in SEQ ID NO:45; and determining an amount of binding of the candidate antibody or fragment thereof to the polypeptide; wherein if the determined amount of binding is significantly greater than the amount of binding to a control polypeptide, said candidate antibody or fragment thereof inhibits cobalamin uptake by a cell that expresses TCblR. In particular embodiments, the polypeptide comprises or consists of amino acid residues 32-183 of SEQ ID NO:53.

In a related embodiment, a method of identifying an antibody or fragment thereof that inhibits cobalamin uptake by a cell that expresses TCblR comprises: contacting a candidate antibody or fragment thereof with a cell or population of cells that expresses a polypeptide comprising or consisting of a region of TCblR capable of binding an antibody or fragment thereof comprising a VH region comprising the amino acid sequence set forth in SEQ ID NO:37 and a VL region comprising the amino acid sequence set forth in SEQ ID NO:45; and determining an amount of binding of the candidate antibody or fragment thereof to the cell or population of cells; wherein if the determined amount of binding to the candidate antibody or fragment thereof is greater than the amount of binding to a control cell or population of cells, said candidate antibody or fragment thereof inhibits cobalamin uptake by a cell that expresses TCblR. In particular embodiments, the polypeptide comprises or consists of amino acid residues 32-183 of SEQ ID NO:53.

In various embodiments utilizing polypeptides comprising or consisting of a region of TCblR capable of binding an antibody or fragment thereof, including any of those specifically described herein, the polypeptide does not comprise the full length TCblR polypeptide, or the polypeptide does not comprise the full extracellular domain of the TCblR polypeptide.

In particular embodiments of the present invention, screening is performed using recombinantly expressed TCblR or a fragment thereof, or using cells comprising exogenous TCblR or a fragment thereof, which is typically expressed in the cell from a recombinant expression construct. Methods utilizing recombinant TCblR are advantageous in that recombinant protein is typically easier to obtain and purify.

In certain embodiments, the TCblR polypeptide or fragment thereof employed in these various assays may either be free in solution, attached to a solid support, borne on a cell surface or located intracellularly or associated with a portion of a cell. One skilled in the art can, for example, measure the formation of complexes between the TCblR polypeptide or fragment thereof and the antibody or fragment thereof being tested. Alternatively, one skilled in the art can examine the diminution in complex formation between a TCblR polypeptide or fragment thereof and its substrate caused by the antibody or fragment thereof being tested.

In certain embodiments of the methods described herein, the antibody specifically binds to the TCblR polypeptide as compared to a control or unrelated polypeptide. In particular embodiments, at least two-fold, three-fold, five-fold, or ten-fold more antibody or fragment thereof will be bound to the TCblR polypeptide or fragment thereof as to an equivalent amount of an unrelated or control polypeptide.

Routine binding assays suitable for screening candidate antibodies and fragments thereof are well known in the art and include, e.g., GST pulldown assays using recombinantly-produced GST-TCblR fusion polypeptides, affinity chromatography, phage display, immunoprecipitation assays under low stringency conditions suitable for precipitating TCblR polypeptides or fragments thereof using antibodies or fragments thereof to TCblR, ELISA assays, and radioimmunoassays.

Methods of the invention may further comprise demonstrating that the antibody or other TCblR modulator inhibits cobalamin uptake into a cell by contacting a cell expressing a transcobalamin receptor with transcobalamin in the presence of the antibody or TCblR modulator; determining an amount of the transcobalamin taken up by the cell; and comparing the amount transcobalamin taken up by the cell to an amount taken up in the absence of the antibody or TCblR modulator, wherein a decreased amount of transcobalamin taken up by the cell indicates that the antibody or TCblR modulator is an inhibitor of cobalamin uptake into a cell.

Such inhibition of Cbl uptake into a cell can produce intracellular Cbl deficiency, which inhibits cell replication due to folate entrapment since folate is needed for DNA synthesis. MAb 1-25 is one such antibody that blocks binding of TC-Cbl to TCblR. All other antibodies generated in the Examples below are binding antibodies and do not interfere with TC-Cbl binding and uptake. All antibodies described herein bind TCblR and are internalized without the participation of TC-Cbl in this process.

B. Methods of Use

The antibodies and fragments thereof described herein specifically bind to TCblR, particularly to specific regions and epitopes within the extracellular domain of TCblR. Thus, the antibodies of the present invention may be used to detect the presence of TCblR in a subject or a biological sample, using any of a variety of diagnostic and prognostic methods, including those described herein. In addition, anti-TCblR antibodies and fragments thereof may be used to block cobalamin uptake by a cell. In other aspects, the antibodies and fragments thereof described herein may be used to inhibit or slow growth or proliferation of a cell, such as, e.g., a tumor cell. The anti-TCblR antibodies and fragments thereof may also be used to deliver an agent, such as a cytotoxin, directly or indirectly (e.g., via a secondary antibody conjugated to the agent) to a cell. In particular embodiments, the anti-TCblR antibodies and fragments thereof described herein are used in methods of treating a tumor, cancer, or hyperproliferative disease or disorder in a subject, such as, e.g., a human subject.

1. Diagnosis and Imaging

As noted above, TCblR is overexpressed in proliferating cells as compared resting or non-dividing cells. Given that tumor cells demonstrate increased proliferation as compared to normal cells, there is a correspondingly higher expression of TCblR in tumor cells as compared to normal cells. Indeed, it has been demonstrated that labeled cobalamin derivatives can be used for imaging and detection of a wide variety of tumors, including, e.g., primary and metastatic breast, lung, colon, thyroid, sarcomatous, prostate, and central nervous system malignancies (Collins, D. A. et al., *Mayo Clin. Proc.* 75:568-580 (2000)). Accordingly, in certain embodiments, the present invention includes methods of detecting and imaging tumor cells, as well as methods of preferentially delivering a therapeutic agent to a tumor cell, by contacting tumors with an agent that specifically binds to TCblR, e.g., an agent that binds to TCblR coupled to a detectable label and/or a therapeutic agent. These methods may generally be applied to a variety of tumors, including those specifically described herein.

Diagnostic or detection methods of the present invention generally involve contacting a biological sample with an antibody or fragment thereof described herein that specifically binds to TCblR under conditions that allow binding and determining whether the antibody preferentially binds to the sample as compared to a control biological sample or predetermined cut-off value, thereby indicating the presence of TCblR in the sample. In various embodiments, the biological sample is, e.g., blood, serum, saliva, urine, sputum, a cell swab sample, or a tissue biopsy. The biological sample may be obtained from an animal, such as a human. In certain embodiments, the predetermined cut-off value is the amount detected in a normal control biological sample. In other embodiments, the predetermined cut-off value is 1.5 or 2 times the amount detected in a normal control individual or biological sample.

Bound antibody may be detected using procedures described herein and known in the art. In certain embodiments, methods of the present invention are practiced using antibodies that are conjugated to a detectable label, e.g., a fluorophore, to facilitate detection of bound antibody. In addition, antibodies can be detected with anti-constant region secondary agents and may be useful for immunochemistry assays of tissues to assess tissue distribution and expression of the TCblR. These include, for example, RIA, ELISA, precipitation, agglutination, complement fixation and immuno-fluorescence.

An enzyme label can be detected by any of the currently utilized colorimetric, spectrophotometric, fluorospectrophotometric or gasometric techniques. Many enzymes used in these procedures are known and can be utilized. Examples are peroxidase, alkaline phosphatase, β-glucuronidase, β-D-glucosidase, β-D-galactosidase, urease, glucose oxidase plus peroxidase, galactose oxidase plus peroxidase and acid phosphatase.

Assessing tissue distribution and expression of the TCblR using, e.g., immunochemistry assays and diagnostic imaging techniques, can be used to detect and diagnose a tumor, cancer or hyperproliferative disease or disorder in a subject. In particular, increased expression of TCblR relative to the surrounding tissue is indicative of increased cellular proliferation. The relative expression of TCblR can be monitored over time to monitor the state or course of a disease, e.g., progression or regression.

In the context of tumor detection in a subject, an antibody or fragment or variant thereof of the present invention is typically coupled to a detectable label and delivered to a subject. The subject is then examined and the presence and/or location of detectable label determined and correlated with the presence of a tumor. Typically, the presence of a tumor is associated with the detection of at least two-fold, at least three-fold, or at least five-fold as much label as detected in a normal control patient.

In a related embodiment, the presence of tumor cells in a tissue sample obtained from a patient is determined by comparing the amount of binding of an anti-TCblR antibody or fragment or variant thereof of the present invention to the tissue sample to the amount of binding to a control normal tissue sample or a predetermined cut-off value. Typically, the presence of tumor cells is associated with at least two-fold, at least three-fold, or at least five-fold as much bound TCblR binding agent as detected in a normal control tissue sample.

These methods may be readily adapted for prognostic and monitoring purposes. For example, the amount of TCblR detected using an antibody or fragment or variant thereof of the present invention may be determined before and after treatment. If the amount is reduced following treatment, it suggests that the treatment is efficacious. However, if the amount is increased following treatment, it suggests that the treatment is not efficacious. Similarly, the location of TCblR detected using an antibody or fragment or variant thereof of the present invention may be determined at first and second time points. If TCblR is detected at different or new locations in the body at the second, later time point as compared to the first, earlier time point, it indicates that the tumor is growing or has metastasized.

The invention contemplates the use of any type of detectable label, including, e.g., visually detectable labels, such as, e.g., dyes, fluorophores, and radioactive labels. In addition, the invention contemplates the use of magnetic beads and electron dense substances, such as metals, e.g., gold, as labels. A wide variety of radioactive isotopes may be used, including, e.g., $^{14}C$, $^{3}H$, $^{99m}Tc$, $^{123}I$, $^{131}I$, $^{32}P$, $^{192}Ir$ $^{103}Pd$, $^{198}Au$, $^{111}In$, $^{67}Ga$, $^{201}Tl$, $^{153}Sm$, $^{18}F$ and $^{90}Sr$. Other radioisotopes that may be used include, e.g., thallium-201 or technetium 99m. In certain embodiments, the detectable label is a CT contrast agent, also referred to as "dyes." Examples of commonly used contrast agents include iodine, barium, barium sulfate, and gastrografin. In other embodiments, the detectable agent is a fluorophore, such as, e.g., fluorescein or rhodamine. A variety of biologically compatible fluorophores are commercially available.

Accordingly, the present invention includes a method of detecting or diagnosing a tumor, cancer, or hyperproliferative disease or disorder in a subject, comprising contacting a biological sample obtained from the subject with an antibody or fragment or variant thereof described herein that specifically binds to TCblR under conditions that allow binding, determining an amount of bound antibody, and determining whether the antibody or fragment or variant thereof preferentially binds to the biological sample obtained from the subject as compared to a control biological sample or predetermined cut-off value, thereby indicating the presence of a tumor, cancer, or hyperproliferative disease or disorder in a subject.

2. Inhibiting Cell Growth and Blocking Cellular Uptake of Cobalamin

Selective essential nutrient depletion by blocking the cellular uptake of folate or vitamin B12 is a strategy that could overcome many of the problems associated with current chemotherapy. It is also likely to be less toxic to the patient and more specific for highly proliferative cancer cells due to their increased demand for these essential micronutrients. However, the use of this approach requires the selective inhibition of the transport of these vitamins. The properties of antibodies and fragments described herein may be exploited to inhibit cellular uptake of Cbl, thereby depleting cells of Cbl and inhibiting Cbl-dependent proliferation of cells.

One embodiment of the invention provides a method for inhibiting the growth of a tumor cell that expresses TCblR comprising contacting the cell with an anti-TCblR antibody, or antigen-binding fragment thereof, described herein.

In some embodiments, blocking antibodies bind specifically to the same TCblR epitopes bound by Cbl or bind specifically to TCblR so as to sterically hinder binding of Cbl to TCblR. These epitopes are present on the extracellular domain of TCblR. Blocking antibodies may be identified by their ability to compete with Cbl binding to TCblR.

In certain embodiments, a blocking antibody is specific for an epitope present in or near an LDLR-A domain. For example, a blocking antibody may bind an epitope present in amino acid residues 54-89 or 132-167 of SEQ ID NO:53. In certain embodiments, the antibody recognizes an epitope in residues 53-63 of SEQ ID NO:53. In another embodiment, the antibody recognizes an epitope comprising residue 85 SEQ ID NO:53. In yet another embodiment, the antibody recognizes an epitope comprising residue 86 of SEQ ID NO:53. In another embodiment, the blocking antibody recognizes an epitope present in amino acid residues 138-165 of SEQ ID NO:53. In yet another embodiment, the blocking antibody recognizes an epitope present in amino acid residues 150-165 of SEQ ID NO:53. In another embodiment, the antibody recognizes an epitope comprising residue 163 SEQ ID NO:53. In yet another embodiment, the antibody recognizes an epitope comprising residue 164 of SEQ ID NO:53.

Another embodiment of the invention provides a method of inhibiting cobalamin uptake by a cell that expresses TCblR, comprising contacting the cell with an antibody, or antigen-binding fragment or variant thereof described herein that inhibits cobalamin uptake. A related embodiment of the invention provides a method of treating a subject having a tumor, cancer or hyperproliferative disease or disorder, comprising providing to the subject an effective amount of an antibody, or antigen-binding fragment or variant thereof described herein that inhibits cobalamin uptake (or with a pharmaceutical composition comprising said antibody or fragment or variant thereof).

In particular embodiments of the above methods of inhibiting cobalamin uptake and treating a subject having a tumor, the antibody or fragment or variant thereof comprises one or more CDR amino acid sequences set forth in SEQ ID NOs: 38-40 and 46-48. Additional particular embodiments provide a method of inhibiting cobalamin uptake by a cell that expresses TCblR, comprising contacting the cell with an antibody or antigen-binding fragment thereof, comprising (i) a heavy chain variable region comprising the VHCDR1, VHCDR2 and VHCDR3 amino acid sequences set forth in SEQ ID NOs:38, 39 and 40, respectively, and/or (ii) a light chain variable region comprising a light chain variable region comprising the VLCDR1, VLCDR2 and VLCDR3 amino acid sequences set forth in SEQ ID NOs:46, 47 and 48, respectively. In certain aspects of the invention, the blocking antibody is mAb 1-25. Examples of other antibodies and fragments and variants thereof that may be used include those described herein that comprise one or more CDR, VH domain or VL domain of mAb 1-25.

3. Drug or Toxin Delivery to Tumor Cells

As described above, the anti-TCblR antibodies, and antigen-binding fragments thereof, of the present invention may be conjugated to agents, including drugs and toxins. Actively dividing cells, such as cancer cells, express an increased amount of TCblR in comparison to non-proliferating, quiescent cells. Accordingly, the subject antibodies, and antigen-binding fragments thereof, including those internalized by cells expressing TCblR, may be used deliver chemotherapeutic agents, drugs and toxins to actively proliferating or tumor cells in order to inhibit proliferation or kill cells expressing TCblR and to treat tumors, cancer and proliferative diseases and disorders.

Toxins such as ricin, cholera toxin, gelonin and saporin are very effective in destroying cancer cells if a toxic dose can be delivered specifically to these cells. This strategy requires a tumor specific carrier to transport the toxin across the plasma membrane into cells, since these molecules cannot cross the cell membrane by either specific or nonspecific transport mechanisms. An ideal target protein would be a receptor or cell surface protein that is expressed and internalized predominantly or only in cancer cells. However, such proteins are scarce and not easy to identify. Many proteins and receptors are expressed in all cell types, and some of these are cell cycle associated or expressed only in actively dividing cells. Such proteins can be carriers for drugs and toxins and may provide some enhanced targeting to cancer cells. However, selective targeting to cancer cells and lack of toxicity to the normal cell population will depend on not only on the differential expression but also on the density of the target protein in the two cell types. For example, a protein with relatively high expression, such as the transferrin receptor, even though differentially expressed in cancer and normal cells, may not be suitable for delivering a toxin because the normal cells may internalize sufficient toxin to kill the cell. The ideal target protein is one with fairly low expression in normal cells, which, therefore, cannot internalize toxic amounts of drugs) but is adequately over expressed in cancer cells to internalize a cytotoxic amount of the drug.

The TCblR is one such protein whose expression is believed to be sufficiently low to render any toxin internalized in normal cells to be ineffective and is believed to be adequately over expressed in some cancers to internalize sufficient toxin to kill the cell. In addition, the cell cycle associated expression of this protein makes it an ideal target for this approach. The use of potent drugs or toxins conjugated to antibody that can deliver the payload to its target antigen is a highly effective strategy that can provide the specificity and speed of action demanded in cancer therapy. The data provided in the Examples demonstrate this receptor can be effectively used for targeted delivery of drugs and toxins.

Certain embodiments of the invention provide a method for inhibiting the growth of a tumor cell that expresses TCblR comprising contacting the cell with an anti-TCblR antibody, or antigen-binding fragment thereof, described herein, wherein said anti-TCblR antibody, or antigen-binding fragment thereof is conjugated to a therapeutic agent.

Another embodiment provides a method for treating a subject having a tumor, cancer or hyperproliferative disease or disorder, comprising providing to the subject an effective amount of a pharmaceutical composition comprising an anti-TCblR antibody, or antigen-binding fragment or variant thereof, described herein, wherein said anti-TCblR antibody, or antigen-binding fragment thereof is conjugated to a therapeutic agent, thereby treating the subject.

Another embodiment provides a method for delivering a therapeutic agent to tumor cells or hyperproliferative cells within a subject having a tumor, cancer or hyperproliferative disease or disorder, comprising providing to the subject a pharmaceutical composition comprising an anti-TCblR antibody, or antigen-binding fragment or variant thereof, described herein, wherein said anti-TCblR antibody, or antigen-binding fragment thereof is conjugated to a therapeutic agent. In particular embodiments, the therapeutic agent is delivered to the cytoplasm of said tumor cells or hyperproliferative cells within the subject.

In certain embodiments of the above methods, the therapeutic agent is a drug, chemotherapeutic, or toxin. In particular embodiments, the toxin is saporin. In particular embodiments of the above methods, the anti-TCblR antibody, or antigen-binding fragment thereof is directly conjugated to the therapeutic agent. In particular embodiments of the above methods, the anti-TCblR antibody, or antigen-binding fragment thereof is conjugated to the therapeutic agent via a linker. In particular embodiments of the above methods, the anti-TCblR antibody, or antigen-binding fragment thereof is conjugated to the therapeutic agent via one or more covalent bonds and not by any non-covalent bonds.

The TCblR-specific antibodies, fragments and variant thereof, and compositions described herein may be administered to subject afflicted with a disease as described herein, such as a cancer, a tumor or a hyperproliferative disorder. In one embodiment, the TCblR-specific antibodies, fragments and variant thereof, and compositions and methods described herein can be used to treat, diagnose, and monitor any type of cancer or tumor. Examples of types of cancers that may be treated, diagnosed, and monitored according to the invention include, but are not limited to, adrenal cortical cancer, anal cancer, aplastic anemia, bile duct cancer, bladder cancer, bone cancer, brain/CNS tumors, breast cancer, Castleman disease, cervical cancer, colon/rectum cancer, endometrial cancer, esophagus cancer, Ewing tumor, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal cancer, hypopharyngeal cancer, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, non-small cell lung cancer, small cell lung cancer, lung carcinoid tumor, lymphoma, mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, skin cancer, small intestine cancer, stomach cancer, testicular cancer, thymus cancer, thyroid cancer, uterine sarcoma, vaginal cancer, vulvar cancer, Waldenstrom macroglobulinemia, and Wilms tumor.

In particular embodiments, these methods can be applied to solid tumors or cancers of the blood and lymphatic systems, including lymphomas, leukemia, and myelomas. Examples of specific cancers that may be treated, diagnosed or monitored according to the invention include, but are not limited to, Hodgkin's and non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, multiple myeloma, transformed and other types of lymphomas.

Examples of specific myeloproliferative disorders that may be treated, diagnosed, or monitored according to methods of the present invention include, e.g., polycythemia vera, essential thrombocythemia, agnogenic myeloid metaplasia, myelofibrosis, myelodysplastic syndrome, and chronic myelocytic leukemia. The methods of the present invention can be used for adult or childhood forms of lymphoma, as well as lymphomas at any stage, e.g., stage I, II, III, or IV. The various types of lymphomas are well known to those of skill, and are described, e.g., by the American Cancer Society (see, e.g., www.cancer.org).

As indicated above, the antibodies and methods described herein may be applied to any form of leukemia, including adult and childhood forms of the disease. For example, any acute, chronic, myelogenous, and lymphocytic form of the disease can be treated using the methods of the present invention.

Subjects may be any type of animal, including mammals, such as humans. In particular embodiments, subjects were previously diagnosed as having a tumor or hyperproliferative disease or disorder.

4. Pharmaceutical Compositions and Kits

An isolated antibody, or fragment thereof, of the present invention can be lyophilized for storage or formulated into various solutions known in the art for solubility and stability and consistent with safe administration into animals, including humans. An antibody composition may contain antibodies of multiple isotypes or antibodies of a single isotype. An antibody composition may contain unmodified antibodies, or the antibodies may have been modified in some way, e.g., chemically or enzymatically. Thus an antibody composition may contain intact Ig molecules or fragments thereof, i.e., Fab, F(ab')$_2$, or Fc domains. In particular embodiments, antibodies may be in solution or attached to a surface such as a polystyrene or latex plate or bead. In certain embodiments, antibodies may be conjugated to an agent as described herein.

The antibodies and fragments described herein also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies and fragments disclosed herein may also be formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and PCT Publication No. WO 97/38731 published Oct. 23, 1997. Liposomes with enhanced circulation time are disclosed in U.S. Pat. No. 5,013,556.

Administration of the TCblR-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount provided and administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to inhibit cell growth or proliferation.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The TCblR-specific antibody-containing compositions of the present invention may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described TCblR-specific antibody in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a TCblR-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a TCblR-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be are administered in a therapeutically effective amount, which will vary depending upon a variety of factors including the activity of the specific compound (e.g., TCblR-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the TCblR-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody or fragment as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-TCblR antibody compositions of this disclosure in combination with one or more other therapeutic agents. Such therapeutic agents may be accepted in the art as a standard treatment for a particular disease state as described herein, such as a tumor, cancer or a proliferative disease or disorder. Exemplary therapeutic agents contemplated include cytokines, steroids, chemotherapeutics, radiotherapeutics, or other active and ancillary agents.

For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising TCblR-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The present invention also includes kits useful in performing assays using the antibodies, and fragments thereof, of the present invention. These kits include a suitable container comprising one or more TCblR-specific antibody or fragment described herein. The antibody may be conjugated or unconjugated. In addition, if the antibody is supplied in a labeled form suitable for an indirect binding assay, the kit may further comprise reagents useful in performing the appropriate indirect assay. For example, the kit may include one or more suitable containers comprising enzyme substrates or derivatizing agents, depending on the nature of the label. Control samples and/or instructions may also be included.

The invention further provides kits for detecting TCblR or cells or tissues expressing TCblR in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use. In particular embodiments, a kit comprises a composition comprising a physiologically acceptable carrier and a therapeutically effective amount of an anti-TCblR antibody, or antigen-binding fragment thereof, described herein.

EXAMPLES

The following examples are provided as further illustrations and not limitations of the present invention.

Example 1

Characterizing Monoclonal Antibodies to Antigenic Domains of the Transcobalamin Receptor The essential role of cobalamin (Cbl) in folate recycling and the cell cycle associated expression of the receptor for cellular uptake of Cbl provides the opportunity to interfere with cellular replication either by blocking the uptake of Cbl or by delivering drugs and toxins into cells using this pathway (Quadros et al., 1996, *Biochem Biophys Res Commun*, 222, 149-54). This example demonstrates the epitope specificity and properties of monoclonal antibodies generated against the extracellular domain of TCblR.

Production of the Recombinant TCblR

The full-length cDNA in plasmid pOTB7 encoding human TCblR was purchased from Open Biosystems. The plasmid was digested with EcoR1 and Xho1, and the cDNA was cloned into pcDNA3.1+. This plasmid was digested first with Kpn1 and then with Pvu2, and the region corresponding to the extracellular domain (ECD) of TCblR was cloned into pcDNA3.1+. This secreted form of the receptor protein corresponds to amino acid residues 32-233 of SEQ ID NO:53 and was expressed in HEK 293 cells by transfection with PolyFect reagent (Qiagen). By selecting for neomycin resistance, clones with stable expression were obtained. The TCblR ECD was secreted into the culture medium and was monitored by the TC-Cbl binding assay during purification as previously described (Quadros et al., 2005, *Biochem Biophys Res Commun*, 327, 1006-10).

Purification of the Recombinant Receptor

The TCblR ECD protein was purified by affinity chromatography using human TC-Cbl as the affinity ligand and a monoclonal antibody to TC covalently coupled to Sepharose 4B matrix to capture the TCblR ECD/TC-Cbl complex (Quadros et al., 2009, *Blood*, 113, 186-92). The recombinant TC protein used in the purification was also produced in HEK 293 cells as a fusion protein with DsRed protein by cloning the human TC cDNA into pDsRed-N1 (Clontech) plasmid. The fusion protein is more stable than the native protein produced in SF 9 insect cells (Quadros et al., 1993, *Blood*, 81, 1239-45) and behaves like the native protein in binding Cbl and binding to the receptor as TC-Cbl. The DsRed TC was partially purified on CM Sephadex, as previously described, prior to saturating with Cbl by incubation with 3 fold excess CyanoCbl (Quadros et al., 1993, *Blood*, 81, 1239-45). The primary objective of this step was to concentrate the TC protein and reduce the volume required for mixing with medium containing the recombinant TCblR ECD. After incubation for 2-4 hours at 4° C., anti-TC antibody-Sepharose matrix was added and incubated at 4° C. overnight with constant mixing. The next day, the Sepharose beads were collected and washed extensively to remove protein contaminants, and the protein was eluted with 0.5 M $MgCl_2$. The eluted protein was extensively dialyzed and purified on a second affinity matrix containing wheat germ agglutinin as previously described (Quadros et al., 2009, *Blood*, 113, 186-92). The final product was checked for purity by SDS-PAGE.

Generation and Characterization of Monoclonal Antibodies

For antibody generation, mice were immunized with 50 ug of the protein followed by two additional injections of 25 ug of the antigen at two week intervals. Antibody titer in the mice and in the hybridoma supernatants was monitored by ELISA. The antigen was diluted to 1 ug/ml and 100 ul of the protein was incubated in Maxisorb ELISA plates (NUNC) for 1 hour. The protein was removed, the wells washed twice in phosphate buffered saline (PBS), blocked overnight with 1% bovine albumin, and incubated overnight with sample containing antibody. The wells were washed, and the amount of antibody bound was determined by reacting with peroxidase conjugated goat anti-mouse second antibody. Ultra-TMB (Pierce) was used as the substrate for the peroxidase. The 96-well plate was read at 450 nm in a Bio-Rad Model 3550 Microplate Reader following acidification with 100 ul 1N HCl.

Figure 3:
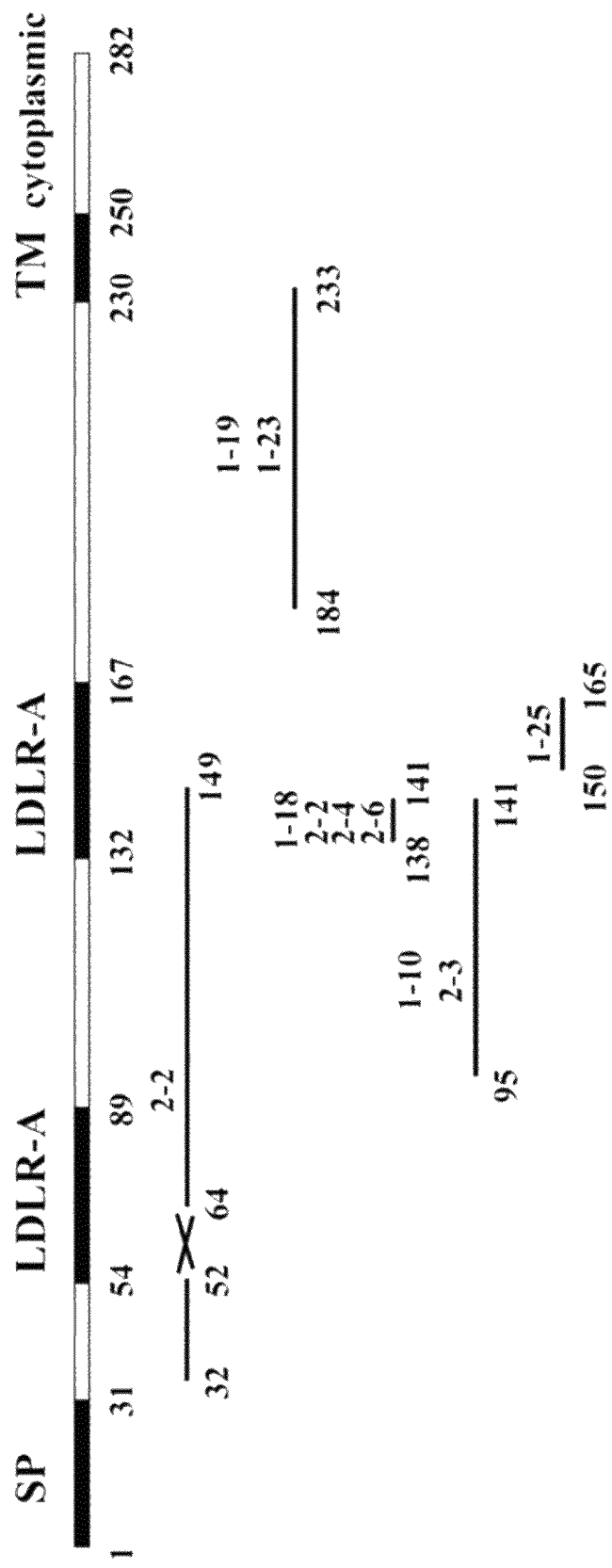
FIG. 3 is a diagrammatic representation of antibody binding regions within the TCblR protein.

Two Balb/c mice immunized with the recombinant 200 aa polypeptide comprising extracellular domain of TCblR (residues 32-233 of SEQ ID NO:53; FIG. 3) were bled 2 weeks after the last injection and screened for antibody titer by ELISA. Positive wells from the first and second mouse fusions were selected for further expansion and cloning. Ultimately, five clones from the first fusion and four from the second fusion were isolated. Selected clones were propagated in culture and used for ascites production in mice. These antibodies were purified by affinity chromatography on a protein G agarose matrix. With the exception of a single IgM clone, all other antibodies were IgG1 isotype. FIG. 1 shows the antibody titer for selected clones. The slope of the dilution curve suggests high affinity binding of these mAbs to the antigen.

Figure 2:
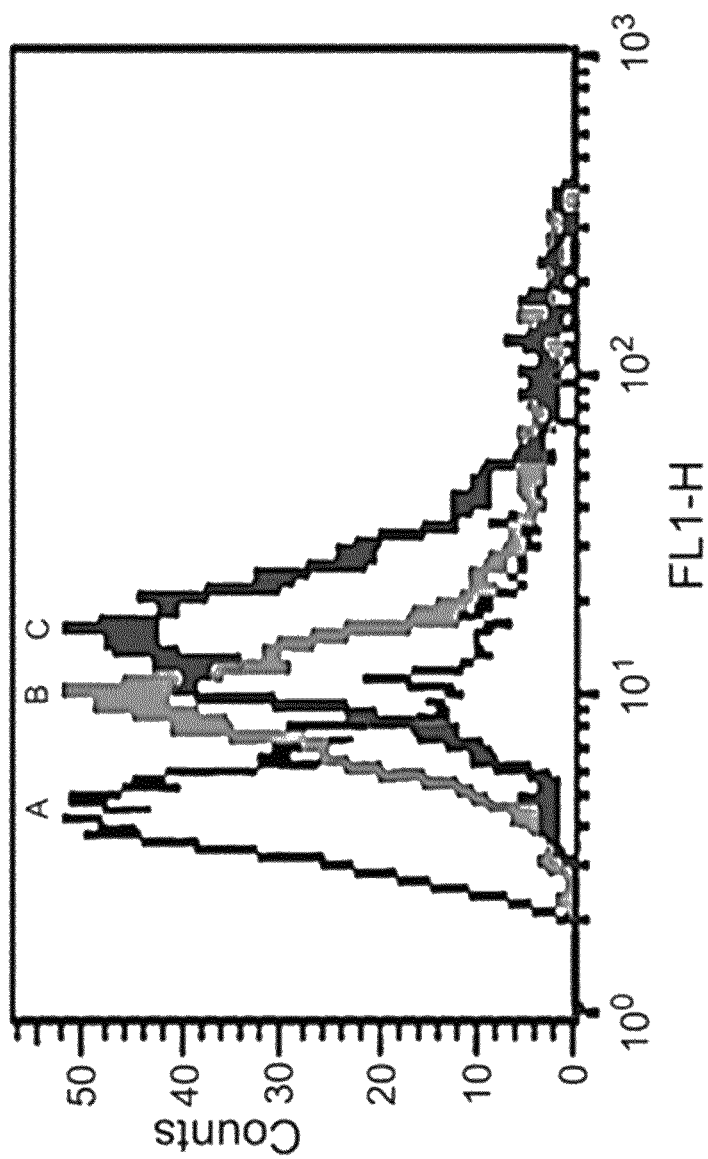
FIG. 2 is a histogram that shows the specificity of anti-TCblR antibody binding to cell surface receptors. K562 cells were incubated with mAb 1-19 followed by FITC tagged anti-mouse IgG and analyzed by flow cytometric separation of antibody positive cells. In the histogram, A represents the isotype control, B represents 4° C., and C represents 37° C.
Figure 4:
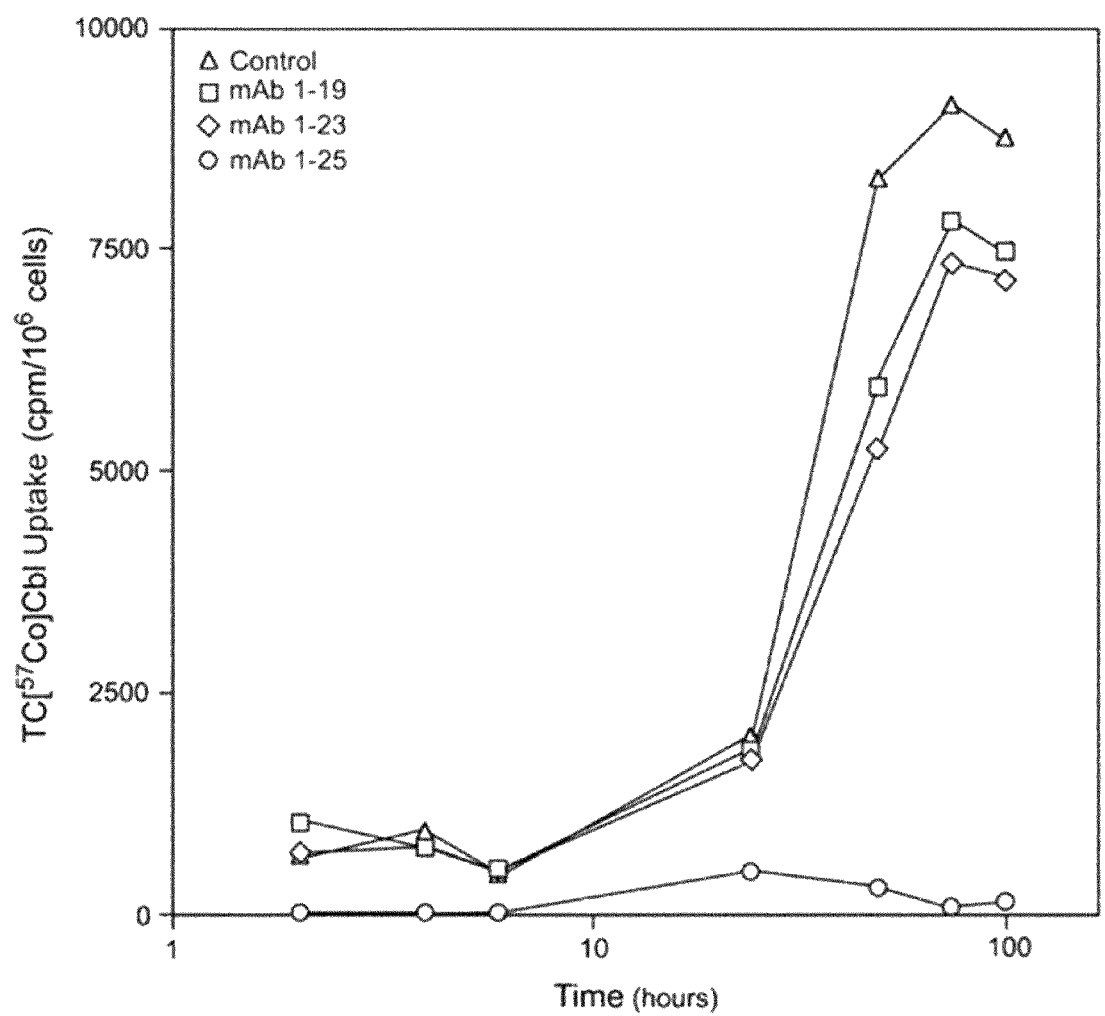
FIG. 4 is a line graph that shows the effect of antibody in the culture medium on the cellular uptake of TC-Cbl. K562 cells were incubated with 120 pmoles mAb 1-19, 1-23, or 1-25. Then 0.026 pmoles of recombinant TC saturated with $^{57}$CoCbl was added to the culture medium and incubated for 2 h, 4 h, 6 h, 24 h, 48 h, 72 h, or 96 h. Cells were collected to measure uptake of TC-Cbl at each time point. mAb 1-25 inhibited uptake of TC-Cbl throughout the 96 h culture period.

The specificity of binding to cell surface receptors was determined by flow cytometric analysis of K562 cells incubated with mAb. As shown in FIG. 2, cells incubated at 4° C. with mAb show binding of FITC tagged anti-mouse IgG ("B"). This binding is further evident from the shift in the peak to the right due to additional receptors expressed when cells are incubated at 37° C. ("C"). All antibodies bound holo-TCblR (i.e., receptor-ligand complex) as indicated by immunoprecipitation of TCblR saturated with the ligand TC-Cbl and can be categorized as binding antibodies. However, mAb 1-25 was unique in that preincubating apo TCblR with this antibody prevented the subsequent binding of TC-Cbl, and it was therefore identified as a blocking antibody (FIG. 4).

Mapping the Epitope Specificity of Antibodies

A sandwich ELISA based assay was utilized to identify the antigen binding epitopes by reacting the antibodies with various truncated forms of the receptor. These C-terminal deleted proteins were produced as recombinant proteins in HEK 293 cells. Antibodies 1-10, 1-18, 1-19, 1-23, 1-25, 2-2, 2-3, 2-4, and 2-6 produced against the recombinant 200 amino acid (aa) extracellular receptor protein were used as capture antibodies by coating 96-well plates (Maxisorb, Nunc). Culture medium containing the truncated TCblR was incubated overnight and the captured TCblR antigen was detected with a goat polyclonal antibody (anti-8D6, R&D Systems) to the antigen. Peroxidase-labeled horse anti-goat IgG (Vector) was used for detecting the binding of the polyclonal antibody as described above.

The recombinant extracellular domain of TCblR and its various carboxy terminal deletion constructs provided the antigens to map the antibody binding sites on this protein. The sandwich assay developed herein utilized purified mAbs immobilized in ELISA plates to capture the TCblR antigen in culture medium, which was then reacted with a polyclonal goat anti-human TCblR to identify the captured antigen. This strategy provided a detailed profile of antibodies binding to truncated forms of the receptor. The extracellular TCblR was used as the positive control, and normal HEK293 cell culture medium and normal mouse IgG served as negative controls. Four of the seven truncated TCblR polypeptides included a mycHis tag comprising a c-Myc epitope tag and a histidine tag. An untagged full length TCblR ECD (aa 32-233) served as a control for the myHis tag. Table 1 shows the binding of various truncated forms of the receptor to specific antibodies. The epitope specificity of these antibodies is shown in FIG. 3.

TABLE 1

Binding of monoclonal antibodies to truncated TCblR proteins expressed in HEK293 cells

| | AA sequence | | | | | | |
|---|---|---|---|---|---|---|---|
| mAb | 32-233 | 32-183 | 32-149 | 32-233-mycHis | 32-94, 142-233-mycHis | 32-137, 166-233-mycHis | 32-52, 64-233-mycHis |
| 1-10 | +++ | ++ | ++ | ++ | − | ++ | |
| 1-18 | ++ | ++ | ++ | + | − | − | |
| 1-19 | ++ | − | − | +++ | ++ | ++ | +++ |
| 1-23 | ++ | − | − | ++ | ++ | ++ | ++ |
| 1-25 | ++ | +++ | − | ++ | + | − | +++ |
| 2-2 | ++ | +++ | +++ | +++ | + | + | +++ |
| 2-3 | ++ | +++ | +++ | +++ | − | ++ | +++ |
| 2-4 | ++ | +++ | +++ | +++ | − | − | ++ |
| 2-6 | ++ | +++ | +++ | +++ | − | − | +++ |

OD 2-3: +++
OD 1-2: ++
OD 0.5-1: +
OD <0.5: −

Epitope recognition by the immobilized mAb was deduced from the ability of the mAb to capture a secreted form of the extracellular domain of the receptor in the culture medium. A loss of binding indicated the deletion of the specific epitope. Based on this binding data, the putative peptide region that interacts with each mAb has been deduced and is summarized in FIG. 3. The region (aa 138-141) within the second LDLR-A domain appears to be highly antigenic with a number of antibodies binding to epitopes within or close to this region. On the other hand, mAb 1-25 appears to bind to the C-terminal end of the second LDLR-A domain (aa 150-165), a region involved in Ca++ binding. This mAb also blocks the binding of holo-TC to TCblR, an interaction that requires Ca++ binding.

Effect on Cellular Uptake of TC-Cbl

Human erythroleukemia K562 cells were cultured in DMEM with 10% FBS. Cells were seeded at a density of $0.2 \times 10^6$ cells in 2 ml medium containing 0.026 pmoles of recombinant TC saturated with 57CoCbl and 120 pmoles of purified mAb. Cells were harvested at various time intervals and radioactivity in the cell pellet was determined in a gamma counter.

As shown in FIG. 4, the uptake of TC-Cbl in K562 cells is effectively blocked when cultured in medium containing mAb 1-25. Binding of the mAb 1-25 to the cell surface receptors appears to block the binding of TC-Cbl whereas mAb 1-19 and 1-23 that bind to the region in between the second LDLR-A domain and the transmembrane domain, have no effect on binding and uptake of TC-Cbl.

Selective essential nutrient depletion by blocking the cellular uptake of folate or vitamin B12 is a novel strategy that could overcome many of the problems associated with current chemotherapy. It is also likely to be less toxic to the patient and more specific for highly proliferative cancer cells due to their increased demand for these essential micro nutrients. However, the use of this approach requires specific drugs or antibodies that would selectively inhibit the transport of these vitamins. The properties of the mAbs described herein could be exploited to deplete cells of Cbl and inhibit Cbl dependent proliferation of cells. A similar approach using monoclonal antibodies to TCblR, the receptor for holo-TC is also likely to block cellular uptake of Cbl as was shown with the blocking antibody.

Blocking the binding of TC-Cbl to TCblR by mAb 1-25 suggests that the peptide region aa 150-165 to which the mAb binds may be involved in TC-Cbl binding. However, the blocking effect may also be due to steric hindrance since this same antibody immunoprecipitates the preformed TCblR/TC-Cbl complex. Therefore, it is likely that the conformational change in the tertiary structure of the receptor due to ligand binding permits antibody binding to its epitope.

All of the other antigenic epitopes did not appear important for ligand binding directly or indirectly, since antibodies to these epitopes did not block TC-Cbl binding. The blocking mAb can effectively inhibit cellular uptake of TC-Cbl by virtue of it binding to apo receptors expressed on the cell surface. All of the antibodies bound both apo and holoTCblR and therefore could be used to deliver drugs, imaging compounds and toxins to cancer cells. The cell cycle associated expression of TCblR (Amagasaki et al., 1990, *Blood*, 76, 1380-6) results in higher and sustained expression of this receptor in many cancers and provides a vehicle for selective targeting of cancer cells using these monoclonal antibodies.

In summary, monoclonal antibodies to the extracellular domain of TCblR, the receptor for cellular uptake of vitamin B12, have been isolated, and the epitope specificity of these antibodies has been identified. These antibodies provide the vehicle to target the receptor for delivery of drugs, toxins, radio-labeled and imaging compounds to tumors. In addition the blocking mAb 1-25 can be used to deplete cells of Cbl, thus inhibiting replication and proliferation.

Example 2

Targeted Delivery of Saporin Toxin by Monoclonal Antibody to the Transcobalamin Receptor In order to exploit the cell cycle associated expression of TCblR, monoclonal antibodies to the extracellular domain of TCblR were used to deliver saporin, an inhibitor of ribosomal assembly, to cancer cells (Stirpe et al., *Biochem J,* 1983, 216:617-25). Monoclonal antibodies to the recombinant extracellular domain of TCblR expressed in HEK 293 cells (Quadros et al., *Blood,* 2009, 113:186-92) were generated and purified as described above. Purified antibodies were used to study the delivery of saporin conjugated goat anti-mouse IgG secondary antibody (Advanced Drug Targeting) to various cell lines maintained in culture.

K562 (ATCC CCL 243) human erythroleukemia cells and U266 (ATCC TIB 196) human myeloma that propagate as a suspension culture; SW48 (ATCC CCL-231) human colon adenocarcinoma cells and KB (ATCC CCL-17) human epidermoid carcinoma that propagate as adherent cells; and HEK 293 (ATCC CRL-1573) human embryonic kidney stem cells were used herein. These cell lines were obtained from the American Type Culture Collection Center, Rockville, Md. and have been identified by karyotyping. Second and third passage cells were frozen in aliquots and used for these studies. MCH 064, MCH 065 and RF peripheral skin fibroblast cultures in passage 9-12 were from The Repository for Mutant Human Cell Strains, Montreal Children's Hospital, Canada. Fresh human bone marrow mononuclear cells were obtained from Lonza, Walkersville, Md.

In addition, HEK 293 cells stably transfected with the cDNA for TCblR in pcDNA 3.1 that overexpress the receptor were used (HEK293TR). These cells have about a ten fold higher expression of TCblR constitutively driven by the CMV promoter, and, therefore, TCblR expression is not cell cycle associated in these transfected cells. All cell lines were maintained in Dulbecco's modified Eagle's minimal essential medium (DMEM) supplemented with 10% fetal bovine serum (FBS) and antibiotics. The primary antibody was incubated with the saporin conjugated secondary antibody for 1 hour at room temperature to form the complex prior to use in the culture.

Binding Specificity of the Monoclonal Antibodies

Binding and internalization of antibody directed to TCblR was determined in HEK 293 cells that were engineered to express a green fluorescent protein (GFP) tag in the cytoplasmic end of TCblR. For this determination, mAb1-25 was pre-incubated with quantum dot (qdot) 625 conjugated goat anti-mouse IgG secondary Ab (Invitrogen) for 60 minutes to form a complex and then incubated with cells in culture.

The specificity of monoclonal antibody binding was also tested in K562 cells that expressed the native TCblR. The binding and internalization of mAb1-19-qdot 625 complex was determined at 4° C. and 37° C., and normal mouse IgG was used as a negative control.

Figures 5A, 5B:
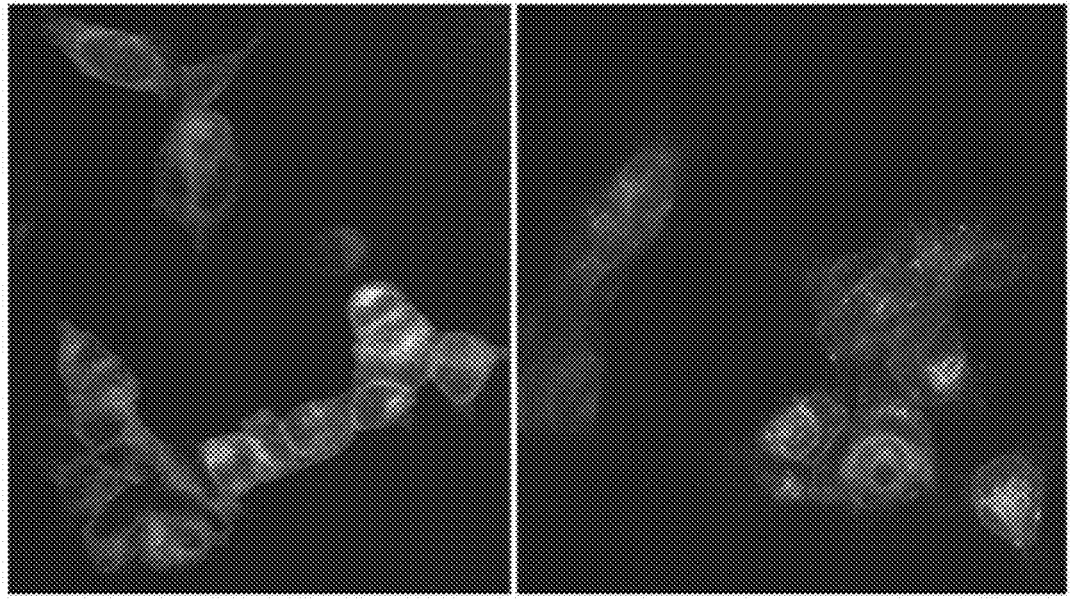
FIGS. 5A-5D are micrographs that show the binding and uptake of mAb 1-19. HEK293TR cells expressing GFP tagged TCblR are shown in FIGS. 5A and 5B, and K562 cells expressing native TCblR are shown in FIGS. 5C and 5D. The mAb was tagged with goat anti-mouse qdot 625red nano particles.
Figures 5C, 5D:
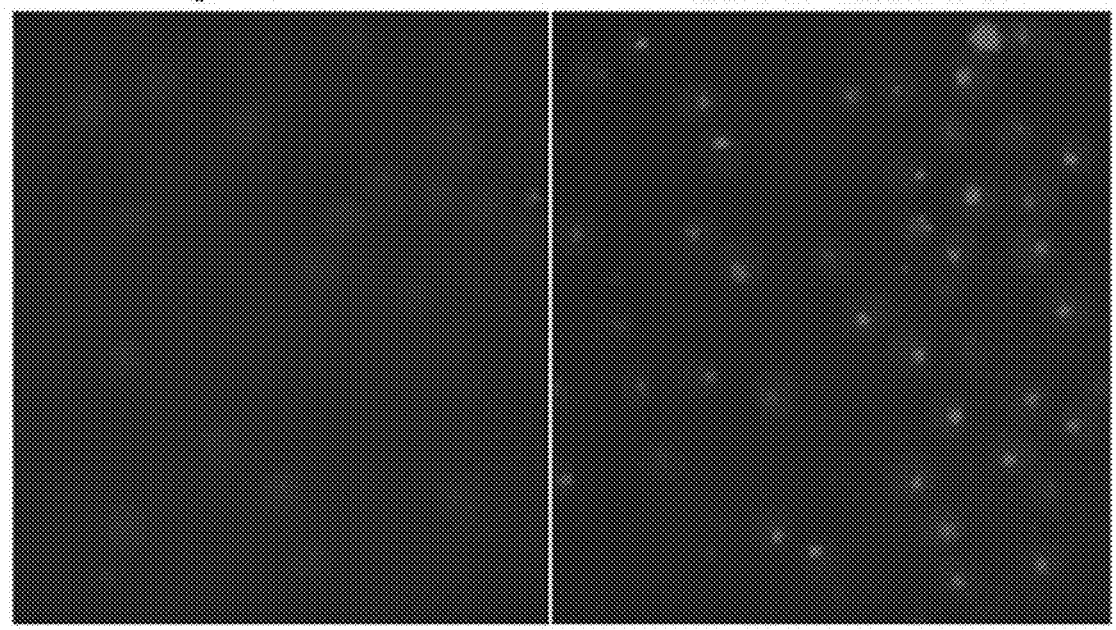

Cells stably transfected to express a chimeric TCblR with GFP tagged to the cytoplasmic end of the receptor showed discrete membrane associated fluorescence. As shown in FIG. 5A, the binding of the mAb1-25-qdot 625red complex at 4° C. was restricted to surface receptors as indicated by mostly membrane associated diffuse fluorescence dispersed throughout the periphery of the cell. Binding and internalization of the mAb1-19-qdot 625red complex bound to TCblR occurred at 37° C. as indicated by segregation of receptors to discrete regions in the membrane as well as the cytoplasm indicated by the colocalization of the red and green fluorescence (FIG. 5B). Similar binding and internalization was observed with mAb1-19-qdot 625red complex when incubated with K562 cells expressing normal levels of non-GFP native TCblR (FIG. 5D). The specificity of binding and internalization was confirmed by substituting normal mouse IgG for the primary antibody and incubating with K562 cells which failed to show any binding and internalization of qdot 625red (FIG. 5C).

Determination of Optimum Concentration of Primary Antibody

To determine the optimum concentration of mAb for the in vitro cell-kill studies, mAb1-25 was pre-incubated with saporin-conjugated goat anti-mouse IgG secondary Ab at a 1:1 molar ratio for 60 minutes to form a complex. Various concentrations of this mAb/Sap-Ab complex (0.1 pM to 50 nM) were incubated with 10,000 SW48 (colon carcinoma) or K562 (erythroleukemia) cells in 96 well culture plates for 72 hours and viable cells were quantified by the MTS assay (Promega).

Initial titration of the mAb/Sap-Ab complex at 1:1 molar ratio incubated with SW48 or K562 cells for 72 hours indicated that a primary Ab concentration of 2-5 nM was adequate for testing the ability of these antibodies to deliver saporin toxin to cancer cells.

Determination of Optimum Ratio of mAb to Saporin-Ab

For using the anti-TCblR antibodies as a carrier of saporin into cells via TCblR, the optimum ratio of primary monoclonal antibody to saporin conjugated secondary antibody (Saporin-Ab) was determined. SW48 colon carcinoma cells were seeded at a density of 10,000 cells/well in 96 well culture plates. In one set of experiments, the concentration of primary mAb was varied from 0.078 to 80 nM while the concentration of secondary Ab was kept constant at 10 nM. In another set of experiments, the concentration of the primary mAb was kept constant at 2.5 nM and the concentration of Saporin-Ab was varied from 10 to 40 nM. Cell viability was determined after 72 hours by the MTS assay.

Figures 6A, 6B:
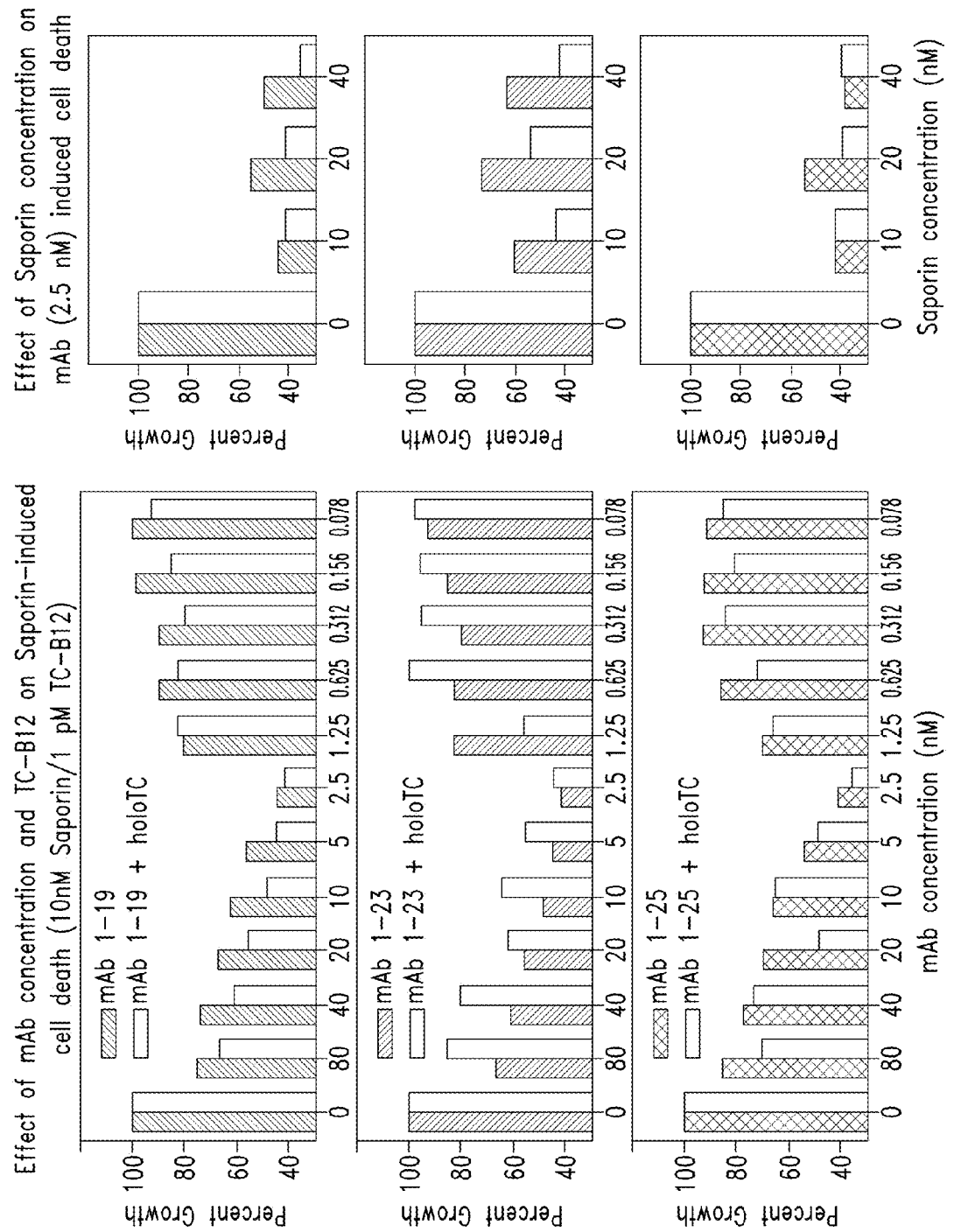
FIG. 6A is a series of bar graphs that show the effect of mAb concentration on saporin-induced cell death used to determine the optimum ratio of the anti-TCblR mAb to the saporin conjugated secondary mAb.
FIG. 6B is a series of bar graphs that show the effect of saporin concentration on mAb-induced cell death used to determine the optimum ratio. The maximum effect was observed at mAb/Sap-Ab concentration of 2.5/10 nM (1:4 ratio). The top graph relates to mAb 1-19, the middle graph relates to mAb 1-23, and the bottom graph relates to mAb 1-25. The shading of bars indicates the presence or absence of holoTc as shown in FIG. 6A.

All three of the anti-TCblR mAbs tested (mAb 1-19, mAb 1-23 and mAb 1-25) yielded similar results with 2.5 nM concentration of the primary mAb as the most effective in inhibiting cell growth (FIG. 6A). The addition of 3.7 nM holo-TC to the culture did not have a significant effect on the outcome even though minor differences were observed due to TC-Cbl competing with the antibody for uptake. The concentration of TC-Cbl used was in excess over the normal TC-Cbl concentration of 0.5-1.5 nM found in plasma. Increasing the concentration of Saporin-Ab did not produce any increase in cell death (FIG. 6B). Thus, a mAb concentration of 2.5 nM and a Saporin-Ab concentration of 10 nM (i.e., a mAb/Saporin-Ab ratio of 1:4) appeared optimum for delivering antibody-toxin into cells via the TCblR pathway.

Effect of Cell Seeding Density on Efficacy of mAb/Saporin-Ab Complex

Seeding density defines the proliferative phase of the culture, and, therefore, cells seeded at a lower density replicate for a longer period of time until the cell population reaches confluency. Since TCblR expression is highest in actively dividing cells, cell lines were tested at seeding densities varying from 1,000-10,000 cells/well with three different primary antibodies (mAb 1-10, mAb 1-19 and mAb 1-25) at 2.5 nM mAb and 10 nM Saporin-Ab concentration.

Figures 7A, 7B:
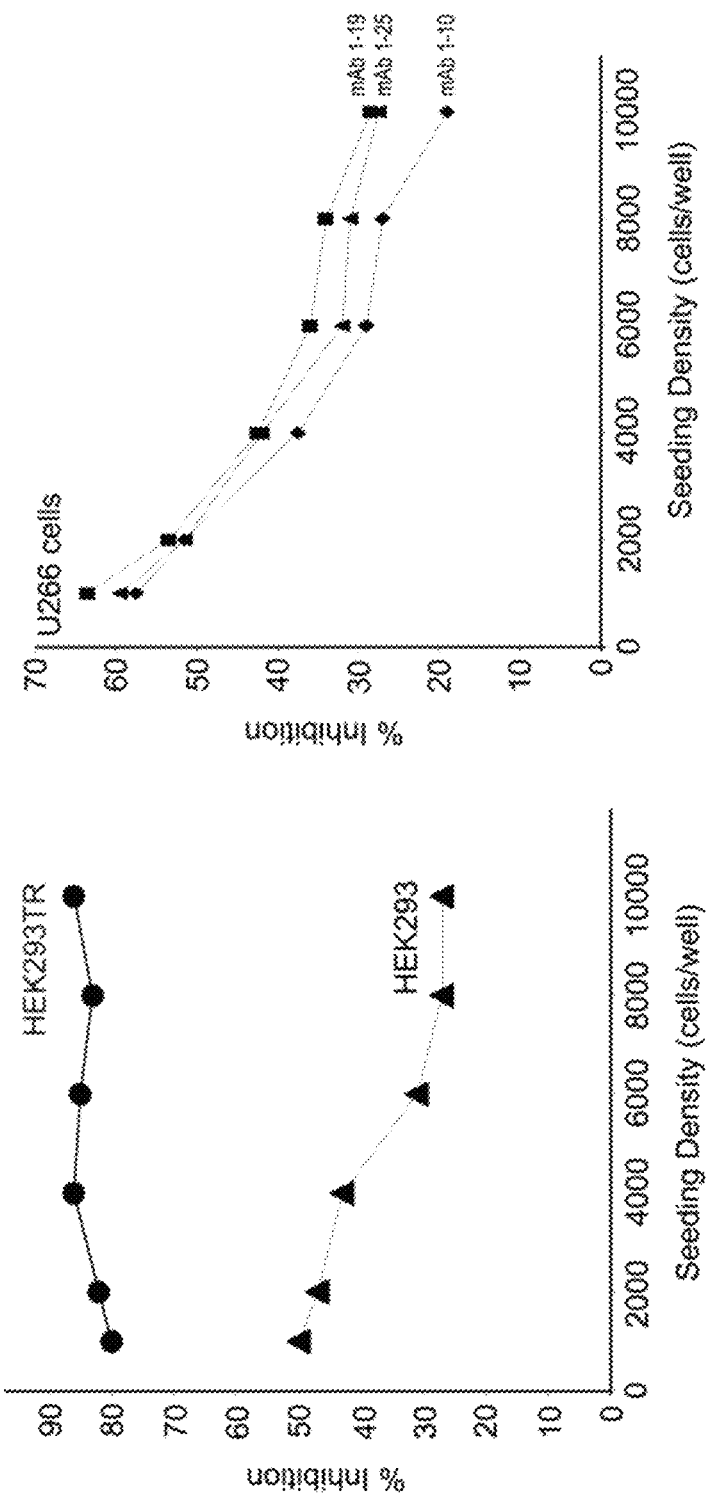
FIG. 7A is a line graph that shows the effect of cell seeding density and receptor expression on saporin-induced cell death in HEK 293 cells. Cells seeded at lower density showed the highest effect due to higher proliferative activity and the native receptor expression coupled to this activity. In constitutively high TCblR expressing HEK293TR cells, the effect of saporin was independent of seeding cell density.
FIG. 7B is a line graph that shows the seeding density dependent inhibition of cell growth of U266 myeloma cells in suspension culture.
Figure 8B:
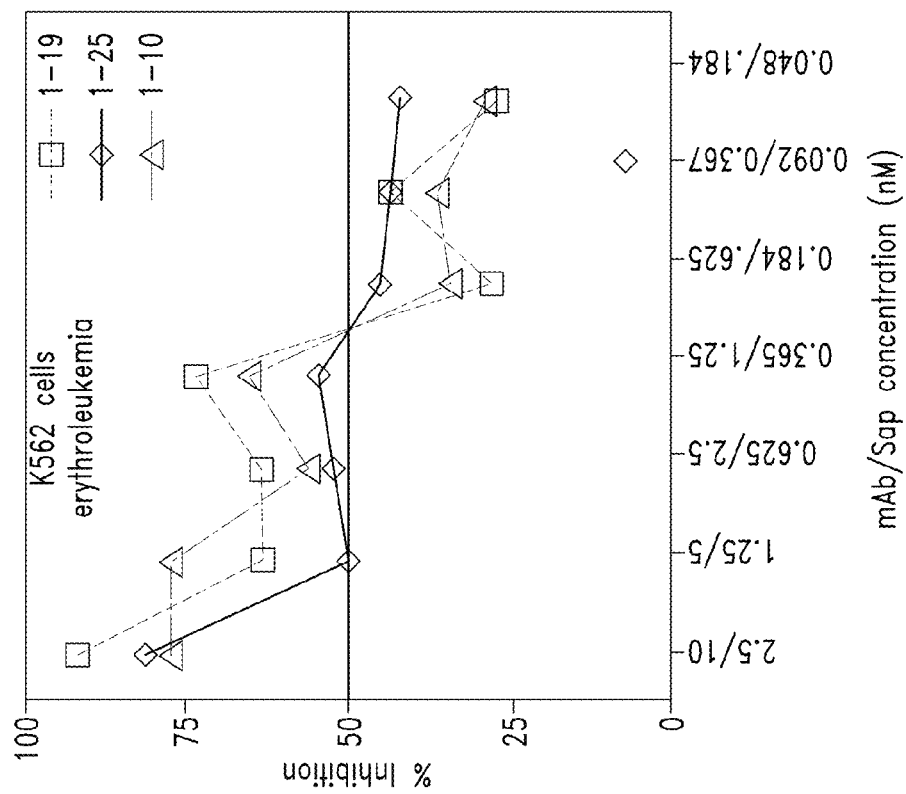
FIGS. 8A-8D are line graphs showing the determination of IC 50 for two adherent (FIGS. 8A and 8B) and two suspension (FIGS. 8C and 8D) cultures. The primary mAb to saporin secondary antibody concentration was maintained at 2.5:10 nM.
Figure 8A:
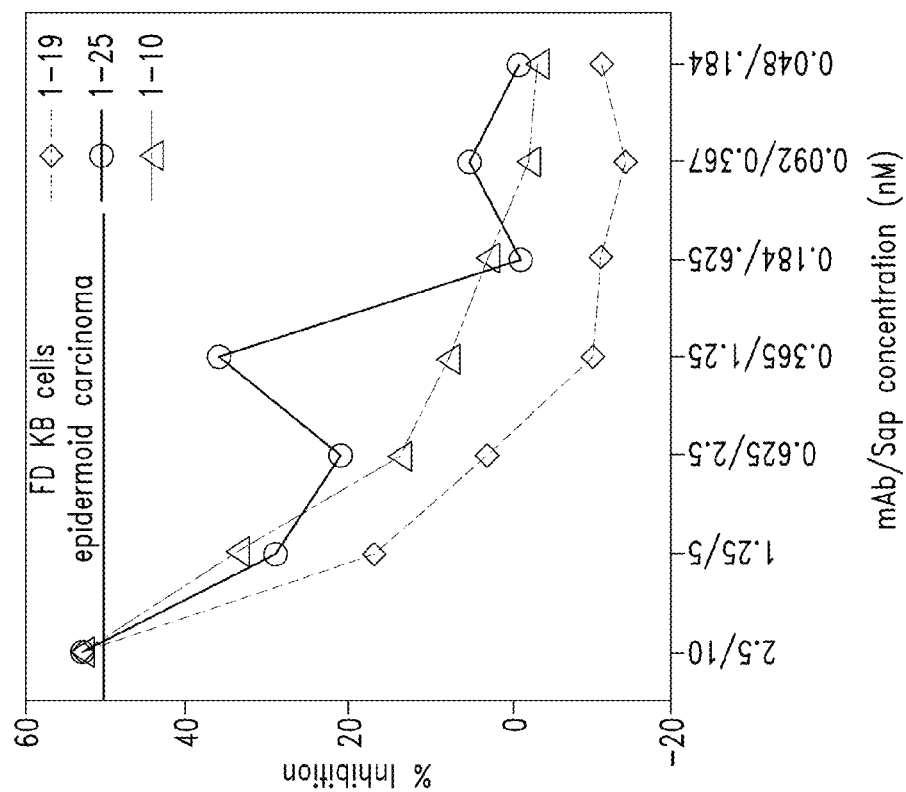
Figure 8D:
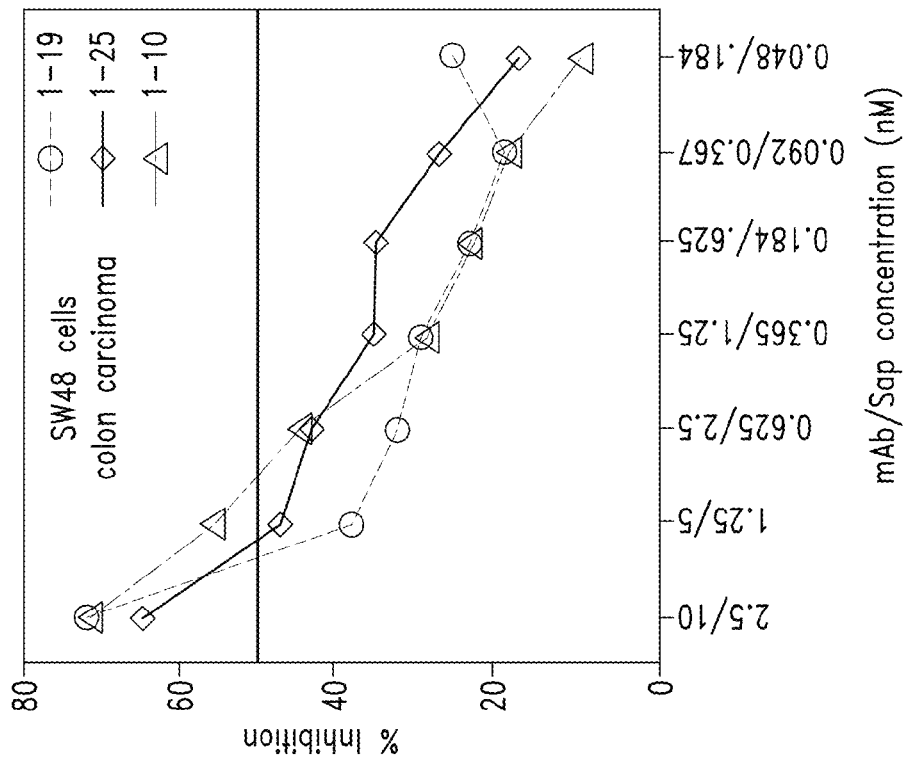
Figure 8C:
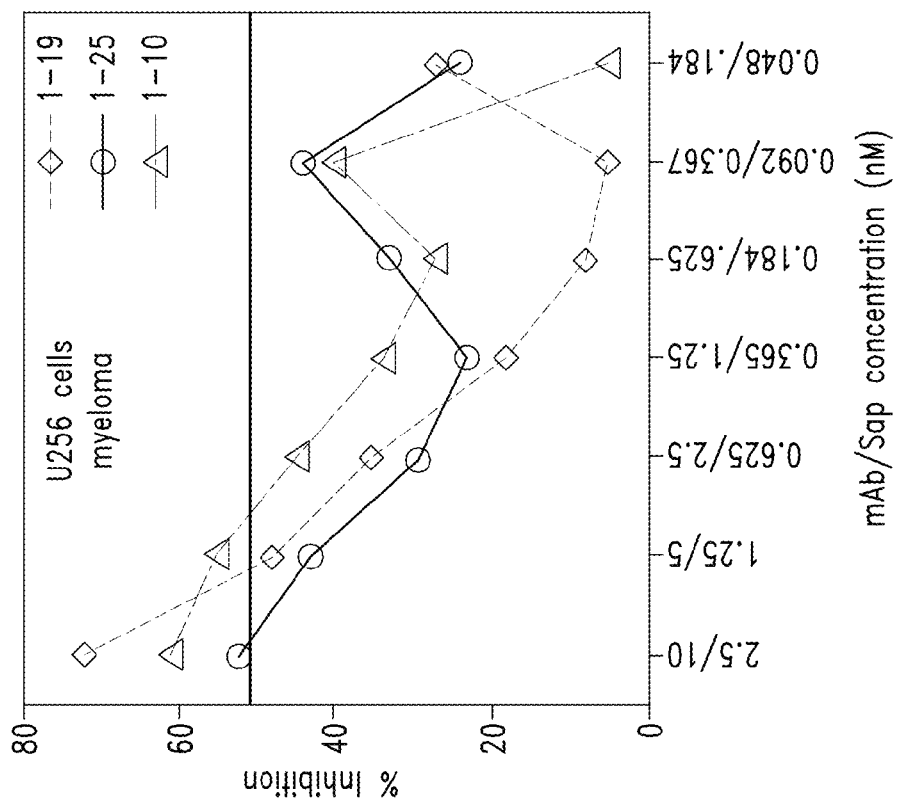

HEK 293 cells stably transfected to over-express TCblR were highly sensitive to mAb-Saporin-Ab, resulting in a >90% inhibition of cell growth. The expression of TCblR in these cells is driven by the CMV promoter and is not dependent on the cell cycle or proliferative state of the cell. The relationship between TCblR expression and the effect of the mAb-Saporin conjugate was evident when normal HEK 293 cells and HEK293TR cells, which over-express TCblR, were seeded at varying densities and exposed to the mAb 1-25-Saporin. Whereas the effect of the toxin decreased with increasing cell density for normal HEK 293 cells, greater than 80% of the HEK293TR cells were killed at all cell densities (FIG. 7A). Thus, the effectiveness of the toxin was directly related to the level of receptor expression. For all cell lines tested where the receptor expression is related to the proliferative state of the cells in culture, the greatest effect was observed when the cells were seeded at a lower density as shown for U266 cells in FIG. 7B. Three mAbs (mAb 1-19, mAb 1-25 and mAb 1-10) were tested and yielded similar results.

Determination for mAb/Saporin-Ab Concentration Required for Inhibiting Cell Growth by 50% (IC50)

Since the toxic effect of Saporin-Ab was more pronounced in cell cultures seeded at lower density, the IC50 determinations were done with cells seeded at 1,000 cells/well in 96 well plates, a mAb/Saporin-Ab ratio of 1:4 and a primary antibody concentration range of 0.046-2.5 nM. Viable cells were determined by the MTS assay after 96 hours in culture.

In order to compare the effective delivery of toxin, the IC50 for different cell lines was determined, and the IC50 for two suspension cultures and two adherent cell lines is shown in FIG. 8. For most cell lines, the IC50 was in the 0.625-2.5 nM range for the primary mAb concentration.

Specificity of TCblR Pathway for Delivering the Saporin-Ab Toxin

The specificity of the TCblR-mediated pathway for internalization of the mAb-Saporin-Ab toxin complex was determined by adding soluble receptor to the culture medium. The soluble receptor competes with the cell surface receptor for the antibody and reduces the Ab-toxin available for cellular uptake resulting in a decrease in percent inhibition. For this experiment, SW48 cells were seeded in 96 well plates at 2,000 cells/well and the amount of mAb/Saporin-Ab used was equivalent to the IC50 concentration.

Figures 9A, 9B:
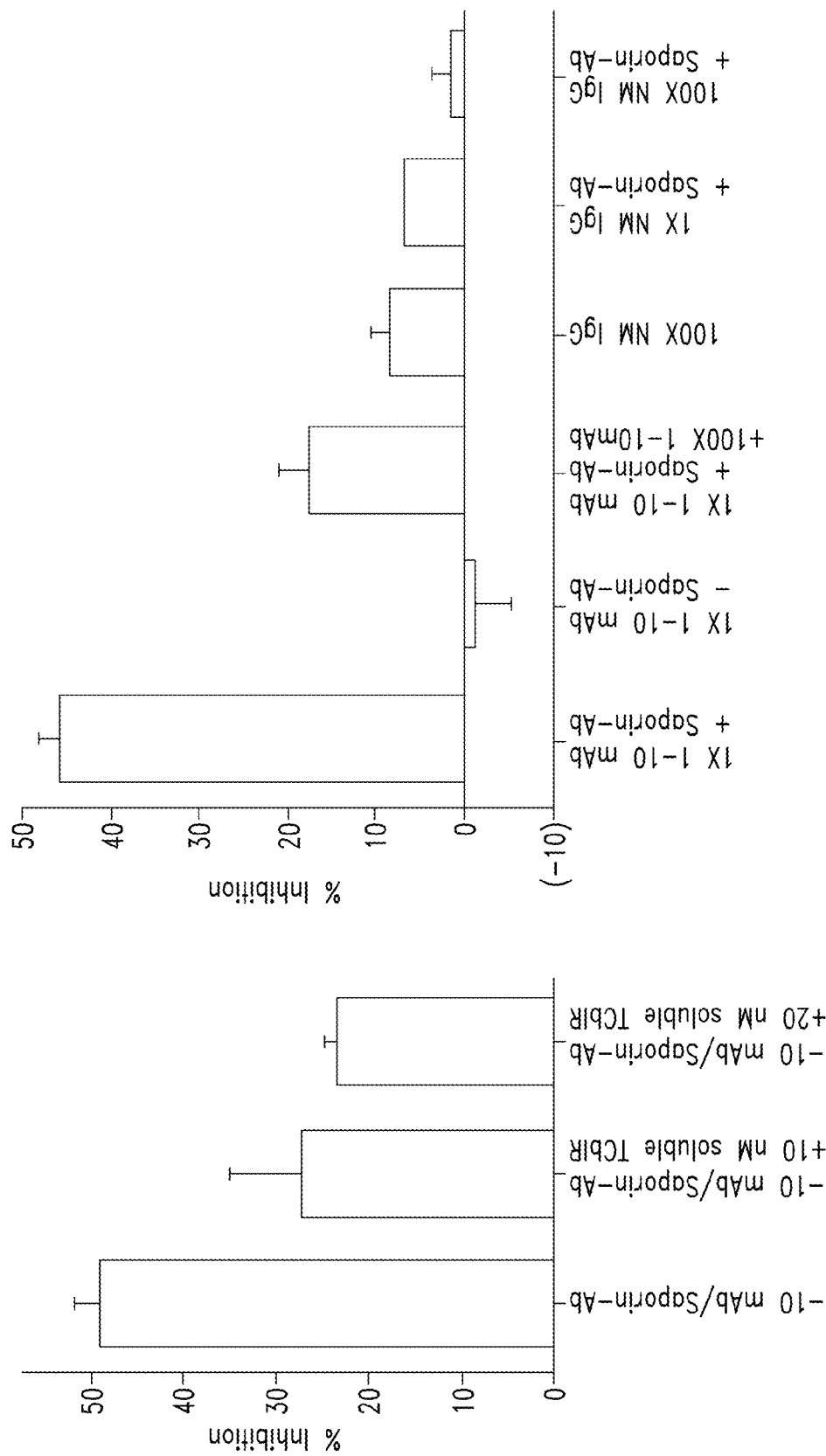
FIG. 9A is a bar graph that shows the specificity of mAb/Saporin-Ab for TCblR. Purified soluble TCblR was added to the culture medium, which resulted in decreased availability of mAb/Saporin to receptors on cells and decreased cell death. The inhibitory effect of the mAb-Saporin Ab also decreased when excess primary mAb or normal mouse IgG was added to the culture.
FIG. 9B is a bar graph that shows that no inhibition of cell growth was observed when saporin-Ab was withheld or when primary mAb was withheld. Values are expressed as percentage of maximum inhibition shown in the first bar.

The specificity of the TCblR pathway was evident from the decreased effect of the toxin when soluble recombinant TCblR was added to the culture medium. By adding soluble receptor to the culture medium, the amount of Ab-toxin available for cellular uptake was reduced, resulting in a decrease in percent inhibition as shown in FIG. 9A.

Specificity of Anti-TCblR mAb for Delivering the Saporin-Ab Toxin

A 100 fold excess of either primary mAb or normal mouse IgG was added to the incubation medium containing a mAb/Saporin-Ab concentration of 2.5/10 nM. A decrease in the anti-TCblR mAb/Saporin-Ab induced inhibition of cell growth should be observed when excess primary Ab is present, since the ratio of Saporin-Ab labeled primary mAb to unlabelled primary mAb should be lower, thereby increasing the probability of unlabelled mAb binding to TCblR. The addition of normal mouse IgG should also result in a decrease in cell-kill, since the secondary Saporin-Ab would also bind to the normal mouse IgG and this complex cannot bind to TCblR.

Figure 9D:
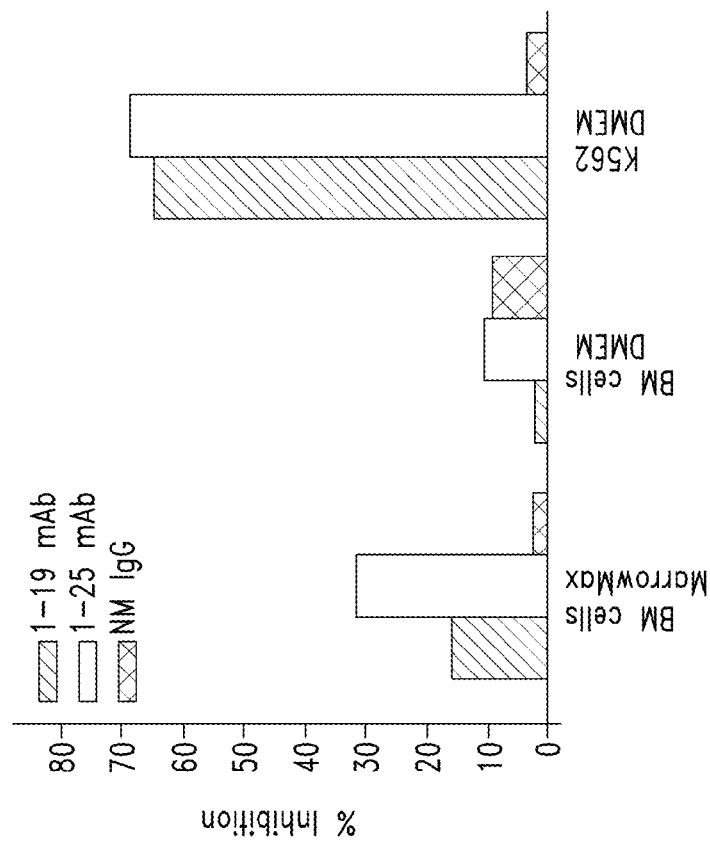
FIG. 9D shows the effect of mAb-Saporin-Ab on human bone marrow cells in vitro.
Figure 9C:
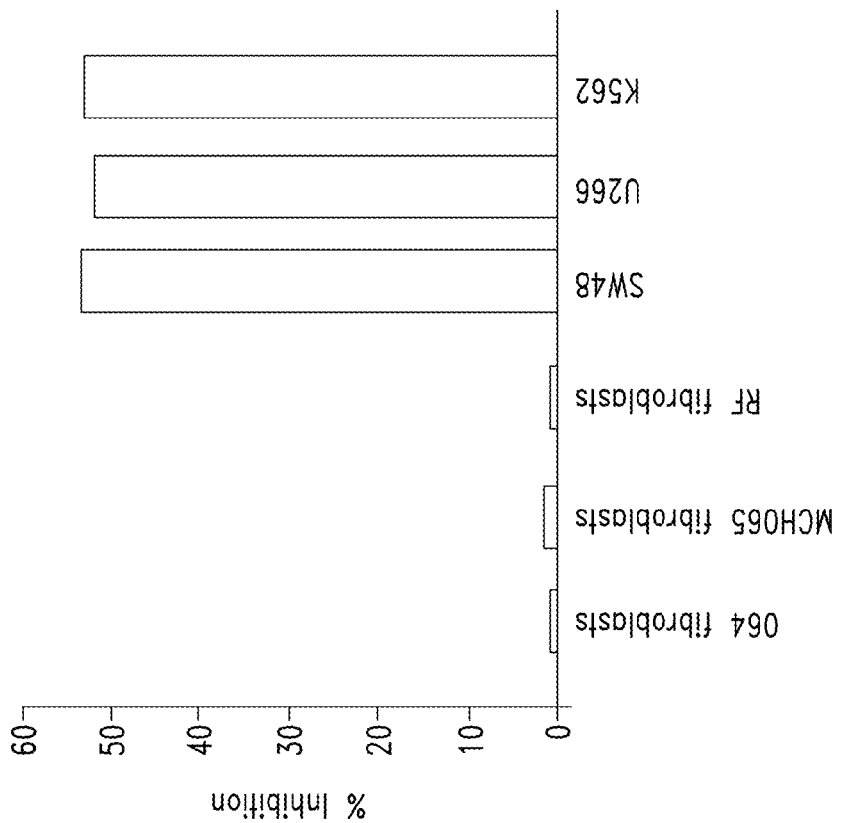
FIG. 9C shows the specificity of mAb-Saporin-Ab for cancer cells and lack of toxicity to primary skin fibroblasts.

The inhibition of cell growth seen with anti-TCblR mAb1-10/Saporin-Ab was decreased when either excess primary Ab or normal mouse IgG was added. Primary mAb or normal mouse IgG in the absence of Saporin-Ab had no effect on cell growth (FIG. 9B). The growth inhibitory effect of TCblR mAb/Saporin-Ab complex appeared to be specific for tumor cell lines, since the growth of three different normal human fibroblast cell lines was not inhibited under identical culture conditions (FIG. 9C). The effect of TCblR mAb/Saporin-Ab complex on the bone marrow cells appeared to be considerably less when maintained in DMEM compared to Marrowmax medium, but overall the effect was far less than the inhibition observed with many tumor cell lines (FIG. 9D).

The TCblR expression is fairly low with only a few thousand receptors expressed in actively replicating cells during the S phase of the cell cycle (Hall et al., *J Cell Physiol*, 1987, 133:187-91; Lindemans et al., *Exp Cell Res*, 1989, 184:449-60; Amagasaki et al., *Blood*, 1990, 76:1380-6). Due to the proliferative nature of neoplastic cells, this expression is up regulated 5 to 10 fold and sustained in certain cancer cells. Based on both the decreased effect of saporin on cells seeded at a higher density compared to cells seeded at a lower density and the virtual sparing of normal cells, which did divide but failed to internalize sufficient toxin, this differential expression of TCblR is sufficient to provide the selectivity needed to target the cancer cell for destruction, while sparing the normal cell population. The use of the TC-TCblR pathway to deliver toxins and drugs provides the dose needed to rapidly destroy highly proliferative tumor cells. The cell cycle associated TCblR expression and the high level of expression in certain cancer cells vs. normal cells provides selectivity and specificity demanded of this targeting strategy. In utilizing these antibodies in vivo in humans, bone marrow toxicity is a potential concern. The low toxicity observed for these cells in DMEM and slightly higher effect seen in Marrowmax medium is related to proliferation and differentiation of marrow cells in the latter. On average, TCblR expression in embryonic stem cells is similar to that observed in skin fibroblasts (Quadros et al., *Blood*, 2009, 113:186-92). Thus, the proliferative state of the cells and the expression level of TCblR would dictate marrow toxicity. Even though the effect on the marrow in vitro appears low, greater toxicity is likely in vivo. Decreasing cell surface receptors by pre-dosing with $B_{12}$ or with unconjugated antibody are two strategies that are likely to decrease the amount of available cell surface receptors to minimize toxicity.

Example 3

Sequencing the Variable Regions of the Anti-Transcobalamin Receptor Antibodies and CDR Determination The VH and VL polynucleotide and amino acid sequences were determined for three of the anti-TCblR antibody clones. Total RNA was extracted from frozen mAb 1-19, mAb 1-23 and mAb 1-25 hybridoma cells using TRIzol® Plus RNA Purification System (Invitrogen, Cat. #15596-026) according to the technical manual. The isolated total RNA was checked by gel electrophoresis.

Total RNA was further reverse transcribed into cDNA using oligo dT anti-sense primer as follows. The following reagents were mixed in a sterile 0.2 ml microcentrifuge tube: 5 ul RNA sample, 1 ul oligo (dT) primer and 8 ul RNase-free water. The contents were thoroughly mixed and spun briefly. The samples were incubated at 65° C. for 5 minutes and then immediately cooled on ice for 2 minutes. The samples were spun briefly, and then the following components were added to the reaction system: 4 ul 5× First-Strand Buffer, 0.5 ul RNase inhibitor, 1.0 ul dNTP mix (10 mM) and 1.0 ul MMLV Reverse Transcriptase. Next, they were mixed gently by tapping and then spun briefly. The tubes were then incubated at 42° C. for 1 hr. The tubes were placed at 75° C. for 10 min to terminate the reaction, and then they were cooled to 4° C.

RT-PCR was performed to amplify the heavy and light chain variable regions of the Ig. PCR was performed as follows. The PCR thermal cycler was preheated to 95° C. The PCR reaction was carried out in a 50 ul total volume: 2 ul First-Strand cDNA, 40.5 ul deionized H2O, 5 ul 10× Taq PCR Buffer, 1 ul dNTP Mix (10 mM each), 0.5 ul sense primer, 0.5 ul anti-sense primer and 0.5 ul Taq Polymerase Mix. The samples were mixed gently and then centrifuged briefly. The samples were then placed in the preheated (95° C.) thermal cycler, and the PCR reaction was run using the following program: 95° C. for 3 min; followed by 25 cycles of 94° C. for 30 sec, 60° C. for 30 sec and 72° C. for 30 sec; followed by 72° C. for 5 min; and then 4° C. until the samples were collected. Once cycling was complete, 4 ul PCR products from each sample were run alongside a DL3000 DNA marker in a 1.5% agarose/GelRed™ gel electrophoresis. The remaining PCR products were stored at −20° C. until further use.

Target PCR products of the heavy and light chains were cloned into a cloning vector separately using standard molecular cloning procedures. Colony screening was employed to screen clones with inserts of correct sizes, and no less than ten independent positive colonies were sequenced for each antibody fragment.

The consensus DNA sequences were determined for each VH and VL region, and the corresponding amino acid sequences were determined. The DNA sequences encoding the mAb 1-19 VH and VL regions are provided in SEQ ID NOs:1 and 9, respectively (FIGS. 10A and 11A). The VH and VL amino acid sequences of mAb 1-19 are set forth in SEQ ID NOs:5 and 13, respectively (FIGS. 10B and 11B). The DNA sequences encoding the mAb 1-23 VH and VL regions are provided in SEQ ID NOs:17 and 25, respectively (FIGS. 12A and 13A). The VH and VL amino acid sequences of mAb 1-23 are set forth in SEQ ID NOs:21 and 29, respectively (FIGS. 12B and 13B). The DNA sequences encoding the mAb 1-25 VH and VL regions are provided in SEQ ID NOs: 33 and 41, respectively (FIGS. 14A and 15A). The VH and VL amino acid sequences of mAb 1-25 are set forth in SEQ ID NOs:37 and 45, respectively (FIGS. 14B and 15B).

Using the numbering algorithm of IMGT (ImMunoGeneTics Information System®; www.imgt.org; Lefranc et al., 2003, *Developmental and Comparative Immunology*, 27:55-77), the leader sequence, FR1, FR2, FR3, FR4, CDR1, CDR2 and CDR3 regions were calculated for each heavy and light chain variable region. The mAb 1-19 VHCDR1 (SEQ ID NO:2), VHCDR2 (SEQ ID NO:3) and VHCDR3 (SEQ ID NO:4) polynucleotide sequences are underlined in FIG. 10A. The mAb 1-19 VLCDR1 (SEQ ID NO:10), VLCDR2 (SEQ ID NO:11) and VLCDR3 (SEQ ID NO:12) polynucleotide sequences are underlined in FIG. 11A. The mAb 1-23 VHCDR1 (SEQ ID NO:18), VHCDR2 (SEQ ID NO:19) and VHCDR3 (SEQ ID NO:20) polynucleotide sequences are underlined in FIG. 12A. The mAb 1-23 VLCDR1 (SEQ ID NO:26), VLCDR2 (SEQ ID NO:27) and VLCDR3 (SEQ ID NO:28) polynucleotide sequences are underlined in FIG. 13A. The mAb 1-25 VHCDR1 (SEQ ID NO:34), VHCDR2 (SEQ ID NO:35) and VHCDR3 (SEQ ID NO:36) polynucleotide sequences are underlined in FIG. 14A. The mAb 1-25 VLCDR1 (SEQ ID NO:42), VLCDR2 (SEQ ID NO:43) and VLCDR3 (SEQ ID NO:44) polynucleotide sequences are underlined in FIG. 15A.

Similarly for the amino acid sequences, the mAb 1-19 VHCDR1 (SEQ ID NO:6), VHCDR2 (SEQ ID NO:7) and VHCDR3 (SEQ ID NO:8) are underlined in FIG. 10B. The mAb 1-19 VLCDR1 (SEQ ID NO:14), VLCDR2 (SEQ ID NO:15) and VLCDR3 (SEQ ID NO:16) are underlined in FIG. 11B. The mAb 1-23 VHCDR1 (SEQ ID NO:22), VHCDR2 (SEQ ID NO:23) and VHCDR3 (SEQ ID NO:24) are underlined in FIG. 12B. The mAb 1-23 VLCDR1 (SEQ ID NO:30), VLCDR2 (SEQ ID NO:31) and VLCDR3 (SEQ ID NO:32) are underlined in FIG. 13B. The mAb 1-25 VHCDR1 (SEQ ID NO:38), VHCDR2 (SEQ ID NO:39) and VHCDR3 (SEQ ID NO:40) are underlined in FIG. 14B. The mAb 1-25 VLCDR1 (SEQ ID NO:46), VLCDR2 (SEQ ID NO:47) and VLCDR3 (SEQ ID NO:48) are underlined in FIG. 15B.

Example 4

Saporin Conjugated Monoclonal Anti-TCblR/CD320 Antibody is Effective in Targeting and Destroying Cancer Cells Antibodies directly conjugated to saporin were generated in order to evaluate the efficacy of saporin directly conjugated to primary antibodies. This Example demonstrates enhanced targeting and destruction of cancer cells by saporin directly conjugated to monoclonal antibodies to TCblR.

The cell lines listed in Table 2 below were obtained from ATCC, and passage 2 and 3 cells were frozen and used in this study. Cells were cultured in Dulbecco's modified Eagle's minimal essential medium (DMEM) with 10% fetal bovine serum (FBS) and antibiotics. Monoclonal antibodies (mAb 1-10, mAb 1-19, and mAb 1-25) generated to the extracellular domain of TCblR were purified by affinity chromatography on a protein G agarose column and used for covalent conjugation of Saporin. The coupling of Saporin and purification of monoconjugate of the antibody was done at Advanced Targeting Systems (San Diego, Calif.). Covalent attachment of Saporin to antibody was accomplished by using a heterobifunctional crosslinker. The ratio of antibody to Saporin was chosen to provide mostly monoconjugate. The final product was separated by PAGE to elimate any di and triconjugates. The antibody-Saporin conjugates were stored in aliquots at −20° C. and used in the present study.

Determination of Optimum Concentration of mAb-Saporin Conjugate

HEK293 cells ($2 \times 10^3$ in 100 ul DMEM) were seeded in 96 well culture plates with 0.156-5 nM mAb-Saporin for 72 hours and viable cells were quantified by the MTS assay (Promega).

Effect of Cell Seeding Density on Efficacy of mAb-Saporin

Initial seeding density defines duration of the proliferative phase in the culture, and, therefore, cells seeded at lower density would continue to divide for a longer period compared to cells seeded at a higher density until the cell population reaches confluency. Since TCblR expression is highest in actively dividing cells and down-regulated in resting cells, cell lines were tested at seeding densities varying from 1,000-10,000 cells/well with 2.5 nM mAb-Saporin concentration.

Determination for mAb-Saporin Concentration for Inhibiting Cell Growth by 50% (IC50)

Since the toxic effect of mAb-Saporin was more pronounced in cell cultures seeded at lower density, the IC50 determinations were performed with cells seeded at 2,000 cells/well in 96 well plates with a mAb-Saporin concentration of 2.5 nM. The number of viable cells was determined by the MTS assay after 96 hours in culture.

Specificity of TCblR Pathway for Delivering the mAb-Saporin Toxin

Figure 16A:
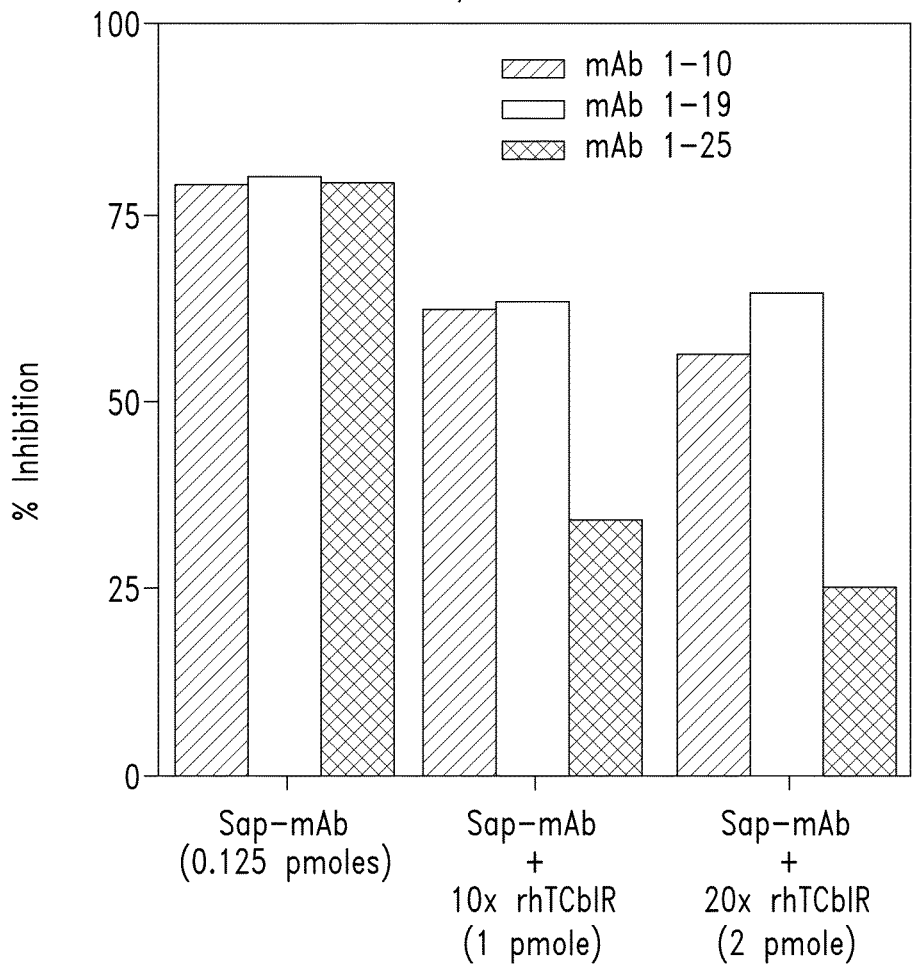
FIGS. 16A-16C are bar graphs that show the effect of recombinant extracellular TCblR on inhibition of cell proliferation by saporin-conjugated mAb.
Figure 16C:
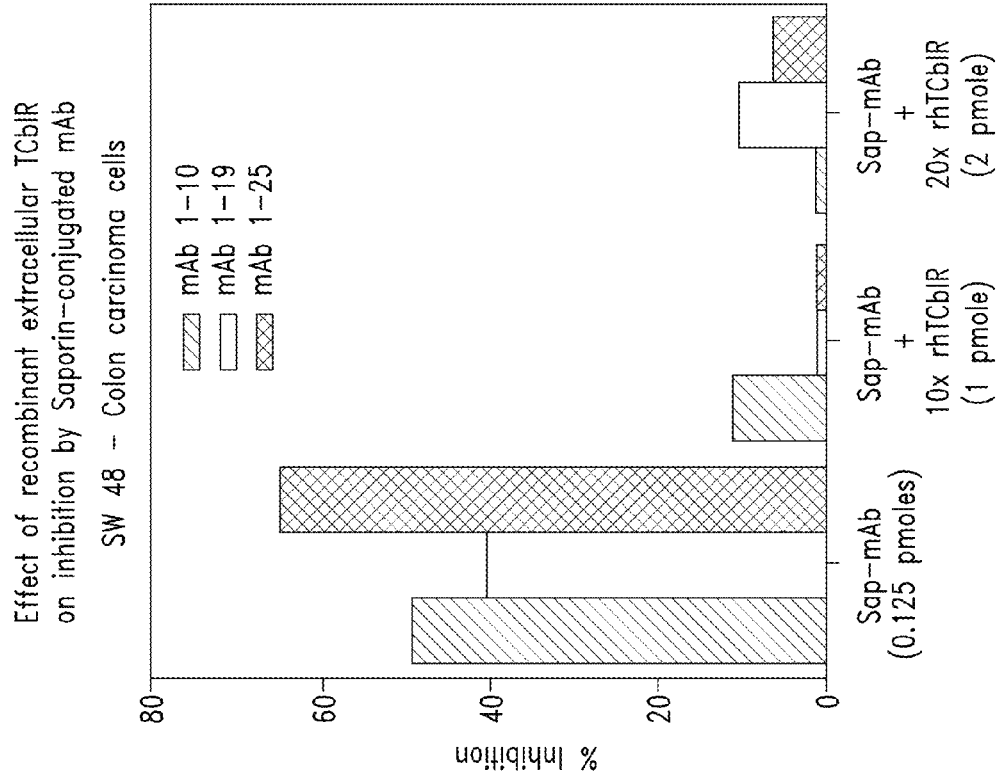
Figure 16B:
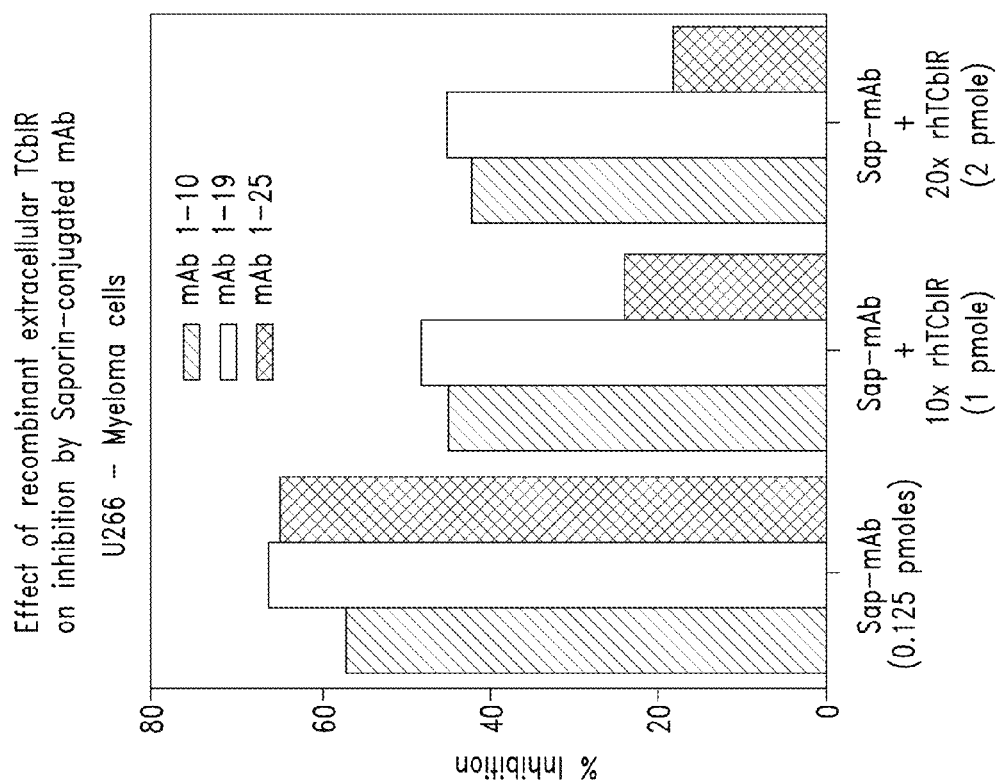

The specificity of the TCblR-mediated pathway for uptake and internalization of the mAb-Saporin complex was determined by adding recombinant soluble extracellular fragment of receptor to the culture medium. The soluble receptor competes with the cell surface receptor for the antibody, and thereby reduces the Ab-toxin available for cellular uptake resulting in a decrease in percent inhibition. For these studies, K562 cells, U266 cells, and SW48 cells were used. Cells were seeded in 96 well plates at 2,000 cells/well and the amount of mAb-Saporin-Ab used was equivalent to the IC50 concentration. As shown in FIG. 16, cells cultured with the recombinant extracellular TCblR demonstrated a decrease in percent inhibition.

Specificity of mAb-Saporin for the TCblR Receptor

A 100 fold excess primary mAb or normal mouse IgG was added to the incubation medium containing a mAb-Saporin concentration of 2.5 nM. A decrease in the mAb-Saporin induced inhibition of cell growth should be observed when excess primary Ab is present since the ratio of mAb-Saporin to unlabelled mAb should be lower and this increases the probability of unlabelled mAb binding to TCblR. The addition of normal mouse IgG should not result in a decrease in cell-kill since this cannot bind to TCblR and, therefore, would not compete with mAb-Saporin for binding to TCblR. As shown in FIG. 17, cells cultured with unlabeled, or unconjugated, mAb demonstrated a decrease in percent inhibition, while those cultured with normal mouse IgG did not have a decrease in percent inhibition compared to mAb-Saporin alone.

Effect of mAb-Saporin on Normal and Cancer Cells in Culture

In order to determine any differential effect of the mAb-Saporin in targeting cancer cells in culture, various normal and cancer cell lines seeded at 1,000, 2,000 and 4,000 cells/well were exposed mAb-Saporin at an antibody concentration of 2.5 nM.

Figure 18:
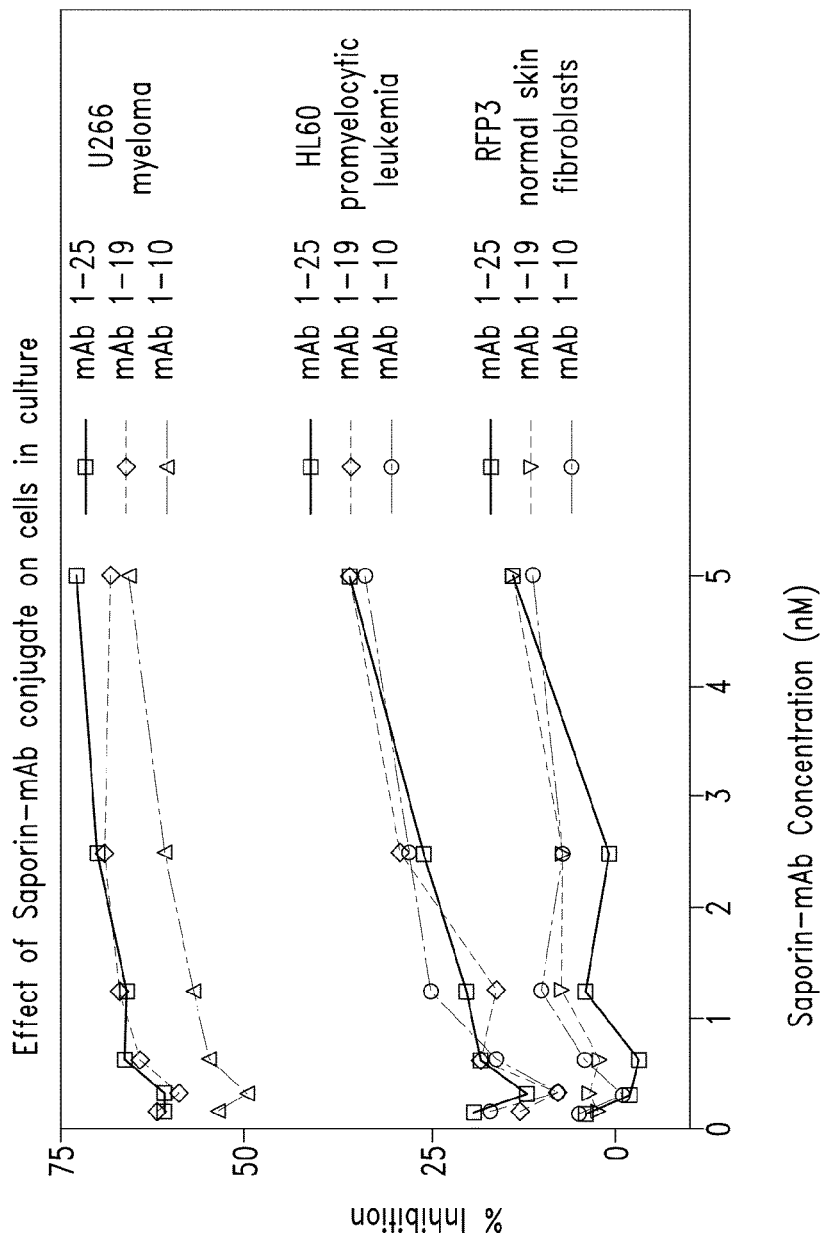
FIG. 18 is a line graph that shows the effect of saporin-conjugated mAb on cell growth in culture.
Figure 19:
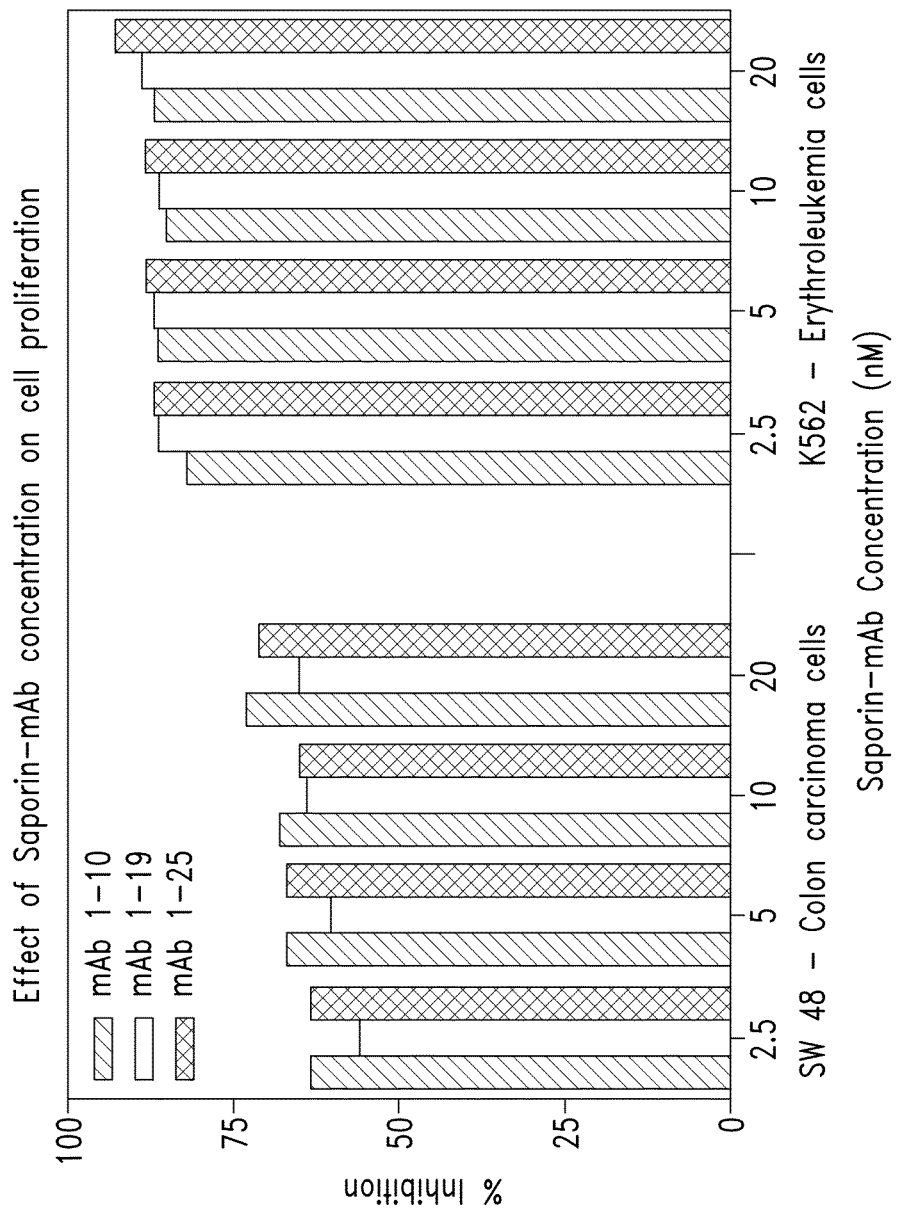
FIG. 19 is a bar graph that shows the effect of saporin-conjugated mAb concentration on cell proliferation in SW48 cells and K562 cells. For each different antibody concentration depicted, the bar at the left is mAb 1-10, the midde bar is mAb 1-19, and the bar at the right is mAb 1-25.
Figure 20:
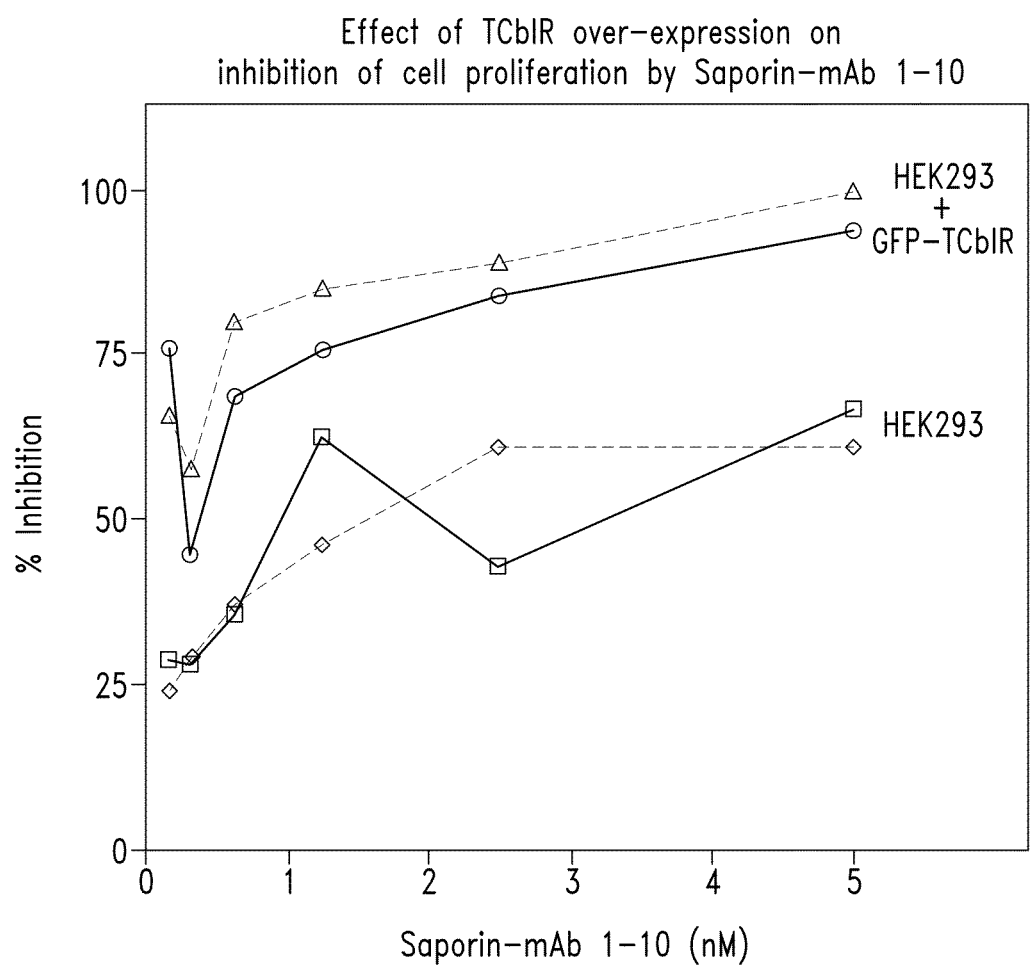
FIG. 20 is a line graph that shows the effect of TCblR over-expression on inhibition of cell proliferation by saporin-conjugated mAb 1-10. The square and diamond represent non-transfected HEK293 cells ("HEK293"), and the circle and triangle represent TCblR over-expressing HEK293 cells ("HEK293+GFP-TCblR").

A number of adherent cell cultures and suspension cultures were propagated in medium containing 0.156 to 5 nM mAb-Saporin. The effective concentration determined by percent inhibition of live cell number showed maximum effect at an antibody concentration of 2.5 to 5 nM (FIGS. 18-19). The effect was more pronounced in suspension cultures than in adherent cultures at all concentrations of the antibody tested. In cell lines with 50% or less inhibition of growth, increasing the antibody concentration did not increase the inhibition. In addition, HEK293 cells stably transfected to over-express TCblR were more severely affected compared to non-transfected HEK293 cells (FIG. 20). Two cell lines RFP3, a skin fibroblast cell line, and ED, a trophoblast line derived from human placenta, served as non-cancerous cell lines, and they were either not affected or minimally affected at the concentrations of the antibody tested. Based on the above data, the IC50 for most tumor cell lines appears to be below 100 pM. However, a mAb concentration of 2.5 nM was chosen for subsequent studies to ensure adequate extra cellular concentration of mAb-Saporin for all cell lines tested.

Figure 21:
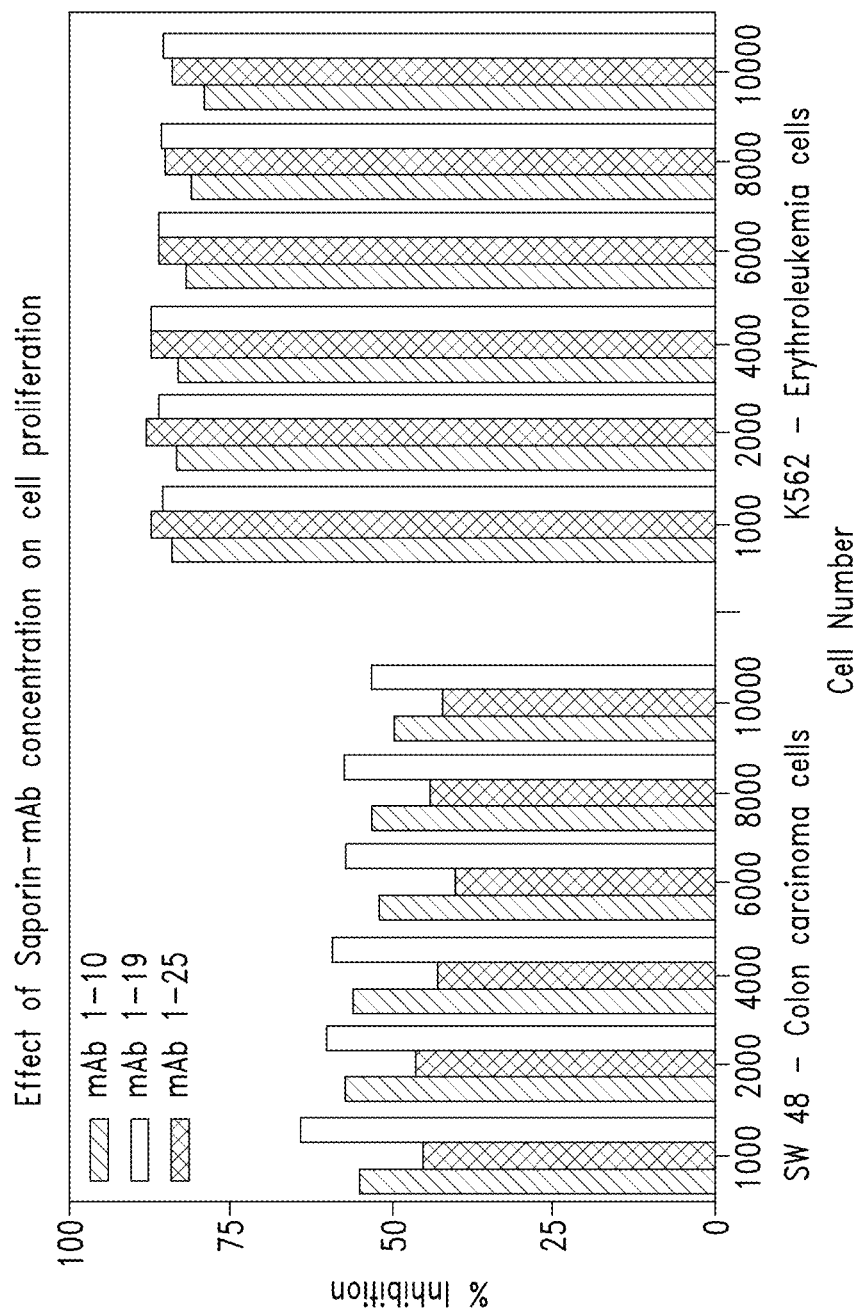
FIG. 21 is a bar graph that shows the effect of starting cell density on inhibition of cell proliferation by saporin-conjugated mAb in SW48 cells and K562 cells.
Figure 22:
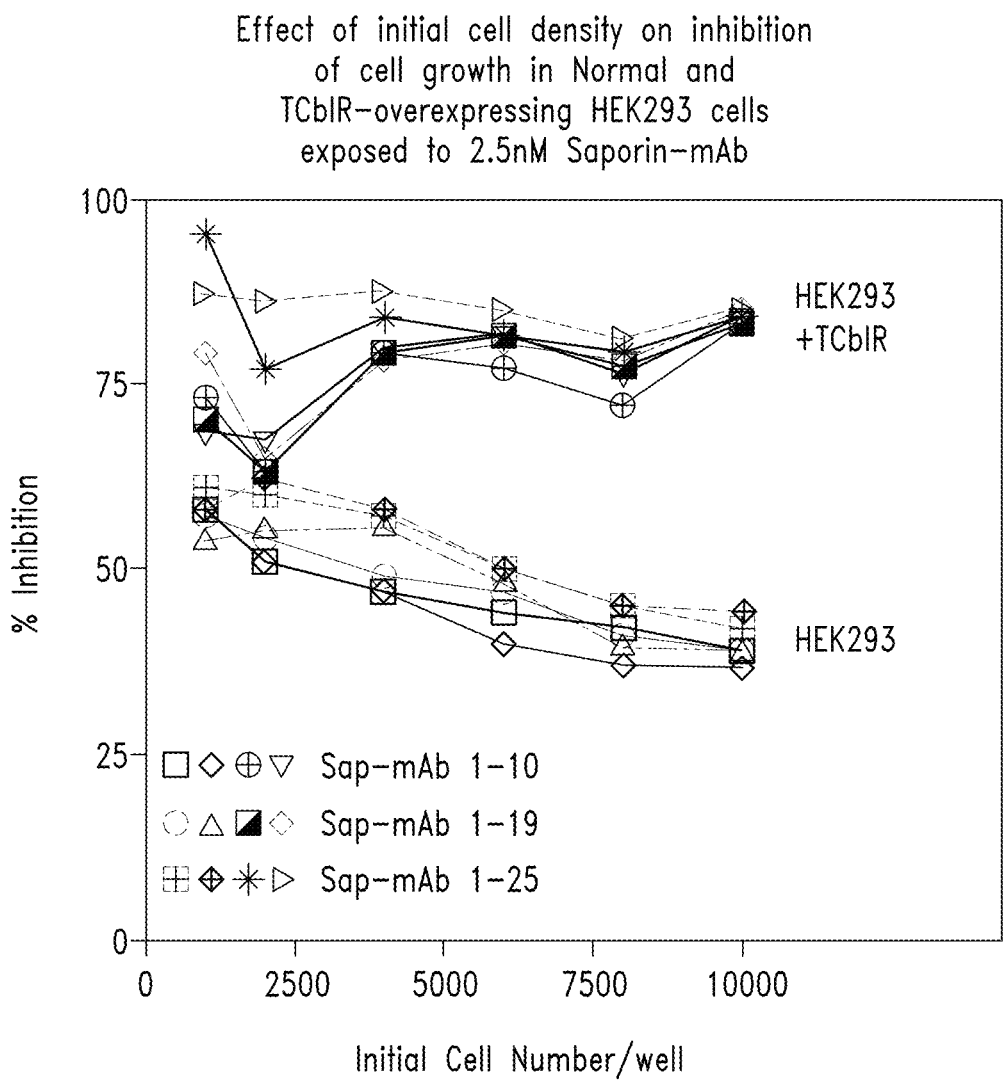
FIG. 22 is a line graph that shows the effect of initial cell density on inhibition of cell proliferation in normal and TCblR over-expressing HEK293 cells exposed to 2.5 nM saporin-conjugated mAb.

Since initial seeding cell density is likely to affect the rate of proliferation and time to confluence, a number of suspension and adherent cell lines were tested at an initial seeding density of 2,000-10,000 cells per well in 96 well plates. The effect of initial seeding density was more pronounced for the adherent cells in comparison to the suspension cultures (FIG. 21). No inhibition was observed with the RFP3 cells, while the ED cells did show some inhibition at lower cell density. Even though HEK 293 adherent cells showed decreased inhibition of cell growth with increasing seeding density as seen in other adherent lines, this trend was not seen with HEK293 cells stably transfected to over express TCblR (FIG. 22).

Since lower seeding density and higher receptor expression appear to have the more inhibitory effect on cell proliferation, the expression of functional TCblR expression in a number of tumor and normal cell lines was evaluated. Since TCblR expression appears to be cell cycle dependent, cell surface receptor expression was determined by evaluating TC-Cbl binding at various time points during a 96 hour culture period. As seen in Table 2, TCblR expression varied considerably among the various tumor lines. In most cell lines TCblR expression peaked between 8-48 h and was followed by a substantial decrease in TC-Cbl uptake by 96 h, a profile observed for most normal cell lines. In some tumor lines, TC-Cbl was substantially up regulated initially and did not decrease to the level seen in normal cells. On the other hand, some tumor lines expressed a moderate level of TCblR throughout the culture period without the peak and decrease seen in normal cells.

TABLE 2

TCblR Expression

| Cell Line | ATCC # | Cell Line Description | Doubling Time | TCblR Expression pg/10^6 cells | | | | |
|---|---|---|---|---|---|---|---|---|
| | | | | 8-18 hr | 24 hr | 48 hr | 72 hr | 96 hr |
| K-562 | CCL-243 | chronic myelogenous leukemia (CML) | 24-40 | 10 | 19 | 10 | 7 | 3 |
| HL-60 | CCL-240 | acute promyelocytic leukemia | 24 | 4 | 6 | 5 | 4 | 3 |
| Jurkat | TIB-152 | acute T-cell leukemia | 25-35 | 20 | 21 | 15 | 6 | 4 |
| U266B1 [U266] | TIB-196 | myeloma plasmacytoma | 55 | 10 | 10 | 7 | 7 | 8 |
| RPMI8226 | CCL-155 | plasmacytoma; myeloma, B lymphocyte | 60-70 | 6 | 15 | 15 | 8 | 7 |
| NCI-H929 [H929] | CRL-9068 | Plasmacytoma, Myeloma | 70 | 20 | 24 | 24 | 33 | 15 |
| U4937 (U937?) | CRL-1593.2 | monocytic cell, histocytic lymphoma | 20-48 | 9 | 9 | 10 | 3 | 3 |
| SW48 [SW-48] | CCL-231 | colorectal adenocarcinoma, epithelial | 35 | 20 | 37 | 18 | 10 | 7 |
| SW480 [SW-480] | CCL-228 | colorectal adenocarcinoma, epithelial | 25-48 | 19 | 15 | 12 | 7 | 10 |
| RKO | CRL-2577 | carcinoma colon, epithelial | 14 | 26 | 27 | 11 | 8 | 8 |
| LoVo | CCL-229 | colorectal adenocarcinoma, epithelial | 36-48 | 9 | 7 | 10 | 12 | 14 |
| Caco-2 | HTB-37 | colorectal adenocarcinoma | 24-62 | 6 | 8 | 7 | 5 | 4 |
| Hep G2 | HB-8065 | hepatocellular carcinoma (epithelial) | 50-60 | 17 | 14 | 9 | 3 | 3 |
| Hep 3B | HB-8064 | hepatocellular carcinoma (epithelial) | 40-50 | 11 | 11 | 10 | 9 | 6 |
| KB | CCL-17 | HeLa Derivatives | 30-40 | 38 | 16 | 15 | 11 | 5 |
| MDA-MB-231 | HTB-26 | adenocarcinoma, mammary gland; breast | 50-60 | 33 | 45 | 10 | 6 | 8 |

TABLE 2-continued

TCbIR Expression

| Cell Line | ATCC # | Cell Line Description | Doubling Time | TCbIR Expression pg/10^6 cells | | | | |
|---|---|---|---|---|---|---|---|---|
| | | | | 8-18 hr | 24 hr | 48 hr | 72 hr | 96 hr |
| MCF7 | HTB-22 | adenocarcinoma, mammary gland; breast | 50 | 12 | 28 | 21 | 10 | 7 |
| HeLa | CCL-2 | cervix, adenocarcinoma(epithelial) | 48 | 13 | 12 | 13 | 9 | 9 |
| A431NS | CRL-1555 | epidermal carcinoma: skin | 80-100 | 3 | 3 | 4 | 4 | 3 |
| MIA PaCa-2 | CRL-1420 | Pancreatic carcinoma | 40 | 22 | 11 | 11 | 7 | 7 |
| PC-3 | CRL-1435 | prostate adenocarcinoma | 50 | 16 | 16 | 18 | 10 | 10 |
| U-373 MG | HTB-17 | identities in question | 24-48 | 19 | 8 | 8 | 6 | 7 |
| HEK-293 Normal | CRL-1573 | human embryonic kidney cell | 24-30 | 9 | 9 | 9 | 5 | 6 |
| EC304 (ECV 304?) | CRL-1998 | T24 (human bladder cell) derivative | 48 | 13 | 16 | 6 | 5 | 5 |
| ED | | embryonic cells derived from placenta | 48 | 8 | 13 | 2 | 2 | 2 |
| HUVEC-CS | CRL-2873 | human umbilical vein | 36 | 12 | 11 | 8 | 9 | 6 |
| RFP3 | | human fibroblast | 18-24 | 3 | 13 | 2 | 2 | 2 |
| MCH065 | | human fibroblast | | 6 | 6 | 8 | 8 | 6 |

Figures 23A, 23B:
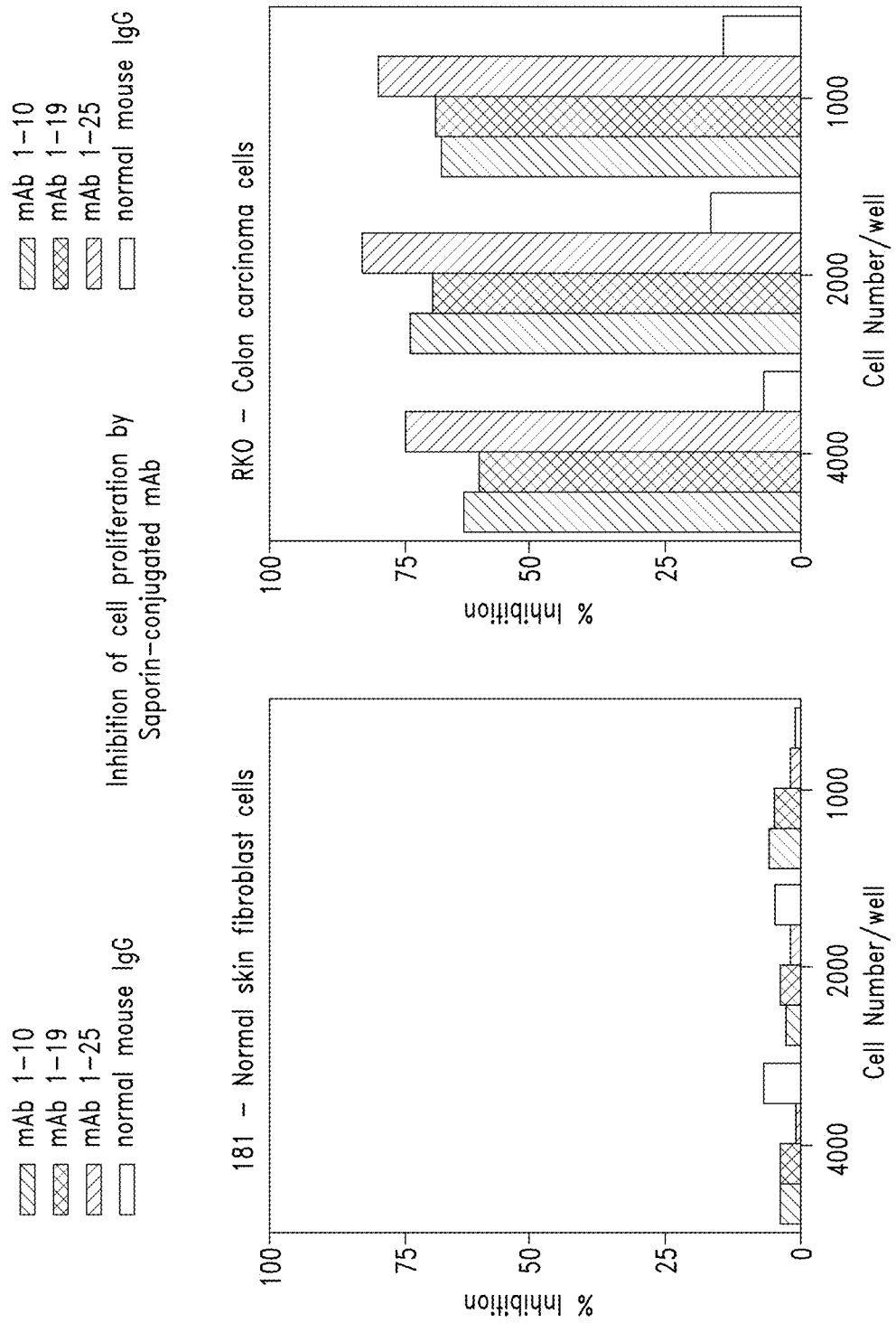
Figure 24:
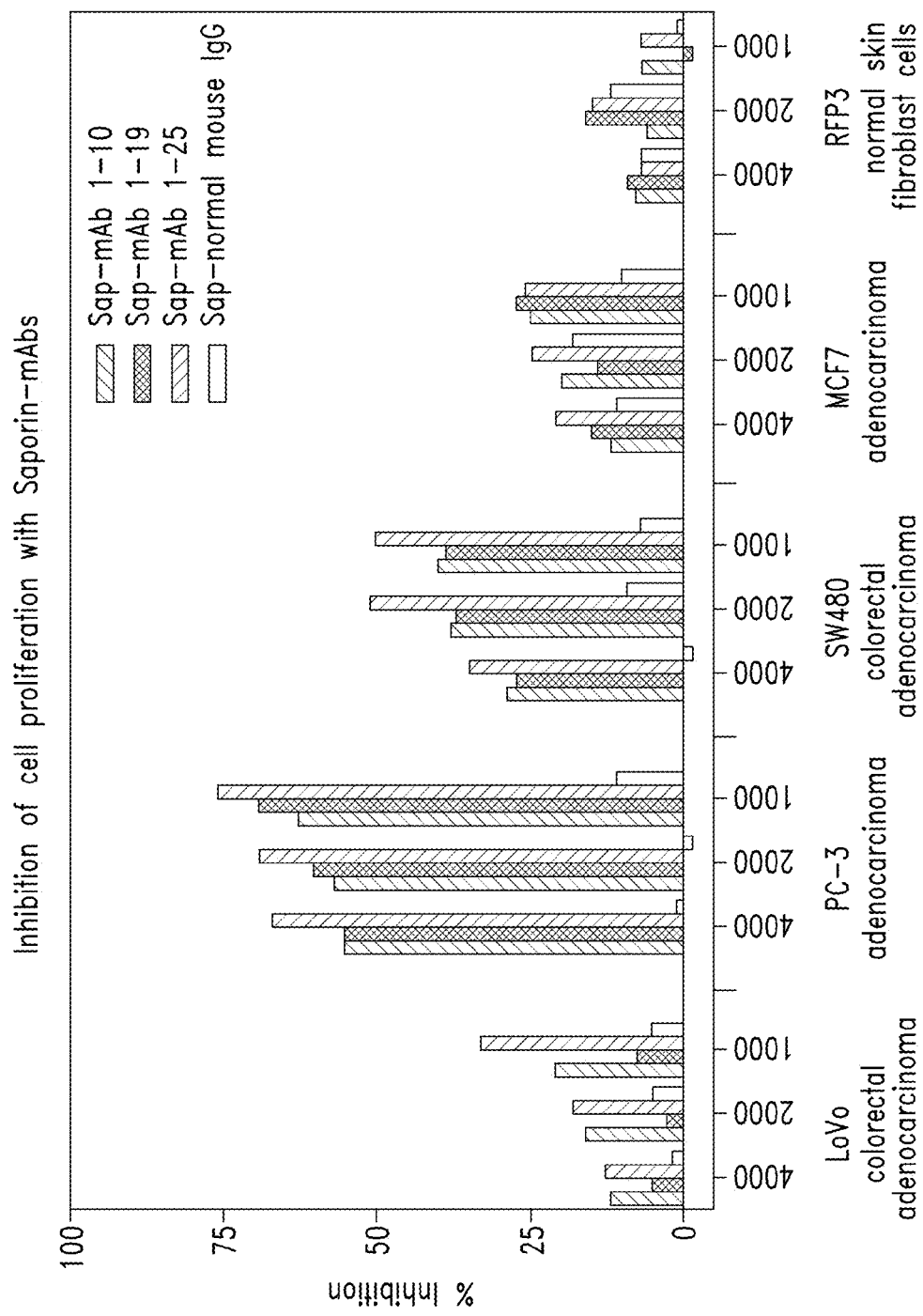
FIG. 24 is a bar graph that shows the inhibition of cell proliferation by saporin-conjugated mAb in LoVo cells, PC-3 cells, SW480 cells, MCF7 cells and RFP3 cells. For each treatment depicted, the bars from left to right refer to mAb 1-10, mAb 1-19, mAb 1-25, and normal mouse IgG.
Figure 25:
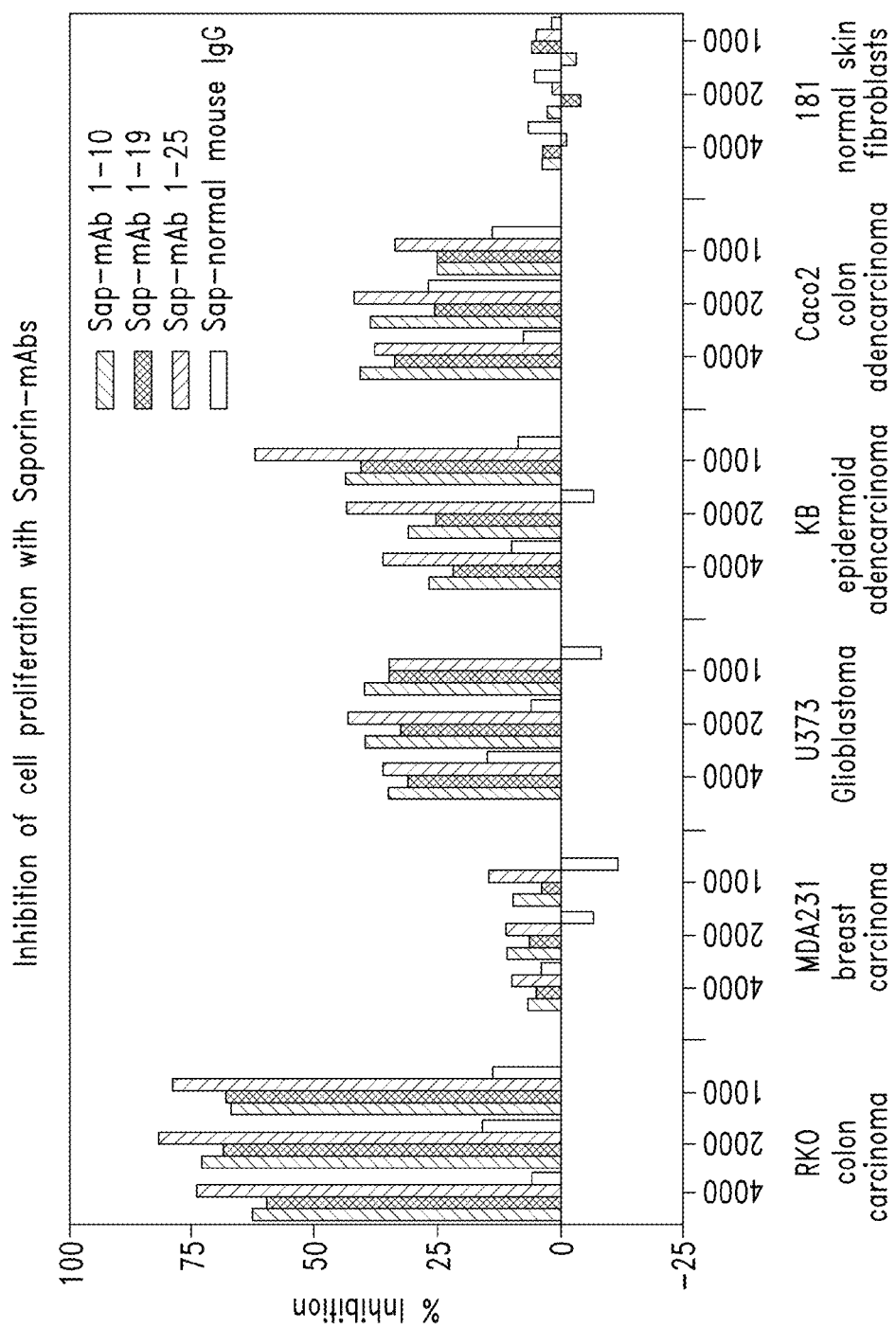
FIG. 25 is a bar graph that shows the inhibition of cell proliferation by saporin-conjugated mAb in RKO cells, MDA231 cells, U373 cells, KB cells, Caco2 cells and RFP3 cells. For each treatment depicted, the bars from left to right refer to mAb 1-10, mAb 1-19, mAb 1-25, and normal mouse IgG.

Because of the wide range of 8-48 h period for peak receptor expression in various tumor lines, the cytotoxic effect of the mAb-saporin was determined at three different initial cell densities of 1,000, 2,000 and 4,000 cells, and three monoclonal antibodies with specificity for different regions of the protein were evaluated (FIGS. 23-25). All three antibodies were effective as carriers of saporin and the average inhibition observed for a specific cell line was similar for all three antibodies. However, there were major differences in susceptibility of different cell lines to the mAb-Saporin conjugate. On average, most of the suspension cell lines showed higher inhibition of cell proliferation with K562 and RPMI18266 cells showing the most inhibition. Among the adherent cell lines, the effect was also varied with RKO, SW48, HeLa and PC3 cells showing the most inhibition and LoVo. Hep G2, Hep 3B, MCF7, MDA-MB-231 and MIA PaCa-2 cells showing least inhibition.

In summary, two of the three representative antibodies (TCbIRKB1-10 and TCbIRKB 1-19) selected were binding antibodies, in that binding of these antibodies to their epitope on TCbIR did not prevent the binding and internalization of the physiologic ligand, TC-Cbl. The third antibody (TCbl-RKB1-25) was a blocking antibody, since binding of this antibody to TCbIR, prevented the binding and cellular uptake of TC-Cbl. The epitope specificity of these antibodies and properties are described in Example 2. All three mAb-Saporin conjugates are fully functional in recognizing the target antigen with high affinity, an important requirement for mAbs to be used as carriers of drugs and toxins. Even though a marginal increase in internalization of mAb 1-10 and 1-19 is observed with TC-Cbl in the culture medium, the binding of the native ligand is not a prerequisite for antibody binding and internalization. Since in the absence of TC-Cbl, the apo receptor remains on the plasma membrane, TC-Cbl binding appears to trigger the necessary response for internalization. The effective binding and internalization of all antibodies, including the ligand blocking antibody, mAb 1-25 is strong evidence that antibody binding triggers a response similar to that of ligand TC-Cbl binding.

Example 5

Mapping the Functional Domains of TCbIR/CD320

The 282aa TCbIR contains a cytoplasmic domain, a transmembrane domain and an extracellular region that binds TC saturated with Cbl with high affinity (Quadros et al., (2009) Blood 113, 186-192). The binding and uptake of TC-Cbl requires $Ca^{++}$ and metabolic energy (DiGirolamo, P. M., and Huennekens, F. M. (1975) Arch Biochem Biophys 168, 386-393). TCbIR expression is highest in actively proliferating cells, suggesting cell-cycle association of this receptor expression (Hall, C. A. (1984) J Lab Clin Med 103, 70-81 and Amagasaki et al., (1990) Blood 76, 1380-1386). The first gene defect of TCbIR in a newborn with elevated methylmalonic acid (MMA) is due to a single aa deletion in the first LDLR-A domain resulting in decreased uptake of TC-Cbl (Quadros et al., (2010) Hum Mutat 31(8):924-929). This report describes the identification of the functional domains and amino acids critical for TC-Cbl binding and cellular uptake. The high affinity interaction of TCbIR with TC-Cbl was investigated using deletions and mutations of amino acid sequences in TCbIR.

Structurally, TCbIR belongs to the LDL receptor family of proteins and contains two LDLR type A domains separated by a cysteine rich CUB like domain (Quadros et al., (2009) Blood 113, 186-192). In all of these receptors, the LDLR-A domains are involved in ligand-binding (Esser et al., (1988) J Biol Chem 263, 13282-13290). Typically, LDL receptor family members are multi-ligand binding proteins; for example, the receptor-associated protein (RAP) binds to all LDLR family proteins and can hinder the binding of a wide variety of ligands (Bu, G. (2001) Int Rev Cytol 209, 79-116). TCbIR has high specificity for TC-Cbl, and the 29 fold lower affinity for apo TC ensures that only TC saturated with Cbl is taken up into cells. Ligands such as LDL and RAP do not affect TC-Cbl binding (Quadros et al., (2009) Blood 113, 186-192).

The LDLR family of proteins comprises variable repeat modules of about 40 amino acids called ligand binding domain (LB in LDLR) or complement-type repeat domain (CR in LRP1) (Esser et al., (1988) J Biol Chem 263, 13282-13290 and van Driel et al., (1987) J Biol Chem 262, 17443-

17449). Each repeat module contains six highly conserved cysteine residues linked by disulfide bonds in the pattern; one to three, two to five, and four to six (Bieri et al., (1995) *Biochemistry* 34, 13059-13065 and Fass et al., (1997) *Nature* 388, 691-693). Each repeat harbors a highly conserved calcium binding site (Brown et al., (1997) *Nature* 388, 629-630) where a calcium ion is coordinated by side chain carboxyl groups from four conserved acidic residues and two backbone carbonyl groups in a octahedral geometry. Each module is structurally independent (Kurniawan et al., (2000) *Protein Sci* 9, 1282-1293) and the disulfide bonds and calcium ion binding cage are critical for maintaining the integrity of the LDLR-A domain for ligand binding (Fass et al., (1997) *Nature* 388, 691-693).

Sequence alignment of the two LDLR-A domains of TCblR with other known LDLR-A modules resulted in the identification of sequences common to these motifs (FIG. 26) (Andersen et al., (2000) *J Biol Chem* 275, 21017-21024). Based on the sequence alignment, the acidic amino acids at position 85 and 86 in the first LDLR-A domain and position 163 and 164 in the second LDLR-A domain appear to be highly conserved and may be involved in coordination with calcium (Brown et al., (1997) *Nature* 388, 629-630).

Generation of TCblR-EGFP

To generate the fusion protein TCblR-EGFP, plasmid containing full-length TCblR cDNA in pcDNA3.1(+) was cut with Bbs I (NEB) and the linearized plasmid was treated with DNA Polymerase I, Large Fragment (Klenow, NEB) to generate blunt-ends. The linearized blunt-end plasmid was then was cut with EcoR I (NEB) to release the insert and the insert was purified by agarose gel electrophoresis and cloned into the vector pEGFP-N3 cut with Sma I (NEB) first and then with EcoR I.

Cellular Expression and Fate of TCblR

Cell surface expression of TCblR was visualized by binding of anti-TCblR monoclonal antibody and goat antimouse IgG-Qdot red secondary antibody. Cells stably expressing TCblR with EGFP tagged to the cytoplasmic end were cultured for 24 h on gelatin coated glass cover slips; washed with medium and incubated for 1 h at 4° C. with preformed primary-secondary antibody complex to facilitate binding of antibody to the cell surface receptor. The anti-TCblR primary and anti-mouse-Qdot secondary antibody complex was formed by incubation of anti-TCblR with secondary antibody at room temperature for 1 h. One set of cover slips was left at 4° C., while another set was moved to 37° C. One cover slip from each set was washed at specific time intervals, fixed in buffered 2% formalin and examined by fluorescent microscopy.

Generation of Deletion Constructs of TCblR cDNA

Human full-length TCblR cDNA in plasmid pOTB7 (Open Biosystems) was digested with EcoR I/Xho I and the cDNA was cloned into expression vector pcDNA3.1 (+). To produce the secreted form of the receptor, this plasmid was digested first with Kpn I to release the full-length cDNA and was subsequently digested with Pvu II to delete the transmembrane and cytoplasmic domains. The extracellular TCblR cDNA fragment was cloned into pcDNA3.1 (+) at Kpn I and EcoR V sites and also into pcDNA3.1 (−) mycHisA at EcoR I and Hind III sites respectively. To delete the C-terminal two N-glycosylation sites, the extracellular TCblR in pcDNA3.1 (+) plasmid was cut with Apa I to delete a 150 nt portion and religated. To generate a further deletion of the receptor by removing the second LDLR-A domain, extracellular TCblR in pcDNA3.1 (+) plasmid was cut with Pml I and Xba I to delete a 252 nt portion and religated. To delete the region between the two LDLR-A domains, extracellular TCblR in pcDNA3.1 (−) mycHisA was cut with Bsg I and Blp I to delete a 141 nt portion and religated. To remove the second LDLR-A domain, extracellular TCblR in pcDNA3.1 (−) mycHisA was cut with Sac I, and the vector and the insert were religated. To produce a TCblR cDNA fragment without the cytoplasmic domain, this region was amplified by PCR using forward primer: AAAAGAATTCCTGGACAGCGCGTGG (SEQ ID NO:57) and reverse primer: AAAAGCGGCCGCGAGC-CAGGACAAAAG (SEQ ID NO:58) containing the EcoR I and Not I sites respectively. The PCR product was digested with EcoR I and Not I, purified by agarose gel electrophoresis and cloned into vector pcDNA3.1 (+).

Site-Directed Mutagenesis

Substitution mutations pDE85, 86>LL and pDE163, 164>LL and deletion mutant p53-63del, were generated using the QuikChange lightening Site-Directed Mutagenesis Kit (Stratagene) following the manufacturer's instructions. The mutated constructs were produced using the extracellular TCblR cDNA in pcDNA3.1 (−) mycHisA plasmid as the template.

To investigate the role of the cytoplasmic domain in TC-Cbl binding and internalization, four amino acid substitution mutants, L264>A (i.e., amino acid residue 264 is mutated from a leucine to an alanine), L265>A, PDZ 1(E257>A, R258>A, L259>A) and PDZ 2 (E270>A, S271>A, L272>A), were generated. These four mutants were produced using the full-length TCblR cDNA in pcDNA3.1 (+) plasmid as the template and all mutations within each of the cDNA constructs were confirmed by sequencing.

Production of Secreted Forms of TCblR and Assay for TC-Cbl Binding

Various constructs with deletions and mutations of the TCblR cDNA were transfected into HEK293 cells using Lipofectamine 2000 reagent (Invitrogen). Stable transfectants expressing high levels of secreted form of TCblR were selected using geneticin resistance.

Previous results showed that full-length TCblR binds to both Con A and WGA, whereas the extracellular TCblR binds only to WGA (Quadros et al., (2005) *Biochem Biophys Res Commun* 327, 1006-1010). TC does not bind to either lectin; therefore, WGA can be used to separate receptor bound TC-[$^{57}$Co]Cbl from free TC-[$^{57}$Co]Cbl. In a typical assay, 1-50 ul of 1:10 diluted culture medium from transient or stable transfected HEK293 cells is incubated with 100 ul (10,000 cpm) preformed TC-[$^{57}$Co]Cbl in 1 ml of assay buffer (20 mM Tris/150 mM NaCl/0.5% Empigen BB, pH7.5) for 1 h at room temperature (RT) followed by 100 ul of a 50% suspension of WGA-agarose and mixing for an additional 1 h at 4° C. The matrix is pelleted by centrifuging at 1,000 g for 5 min and washed twice with 1 ml assay buffer. The radioactivity associated with the matrix is determined as a measure of receptor bound TC-Cbl. The TC-[$^{57}$Co]Cbl for the assay is prepared by incubating recombinant human TC (rhTC) with [$^{57}$Co]Cbl (MP Biomedicals) for 1 h at RT.

For the determination of the TC-Cbl binding affinity of the secreted form of TCblR, 0.02 pmoles of recombinant human TC (rhTC) saturated with [$^{57}$Co]Cbl was mixed with 0.04-1.18 pmoles of unlabeled TC-Cbl and incubated with an aliquot of the TCblR for 1 h at RT and assayed for binding as described above. The affinity constant (Ka) was determined by Scatchard analysis of the binding data.

Deletion constructs missing the glycosylation sites that resulted in loss of binding to lectins could not be tested for TC-Cbl binding using the WGA-agarose method to separate receptor bound TC-Cbl from free TC-Cbl and therefore an indirect assay method was devised to evaluate TC-Cbl binding to these truncated proteins. This assay utilized the ability of excess truncated TCblR proteins to compete with the full-length secreted form of TCblR for binding to a known amount of radiolabeled TC-Cbl. Decrease in binding of TC-Cbl to the full length TCblR was used as a measure of truncated TCblR competing with the full length TCblR for binding to a fixed amount of TC-Cbl.

Assay for Cellular Uptake of TC-Cbl

Cells ($0.5 \times 10^6$) were seeded in complete DMEM with 10% FBS and 2 mM glutamine in six-well plates. Next day, culture medium was removed from the plates and preformed TC-[$^{57}$Co]Cbl complex (40 pg $B_{12}$,16000 cpm) diluted in 1 ml DMEM was added to each well. After 1 h incubation at 37° C., medium was removed and cell layer was washed twice with 2 ml HBSS. Then 0.3 ml Trypsin/EDTA was added to the wells and incubated for 10 min at 37° C. followed by 1 ml HBSS/5 mM EDTA. The detached cells were collected by centrifugation for 5 min, at 3,000 rpm, 4° C. Supernatant was counted for radioactivity and represented membrane bound cell surface TC-Cbl counts released by trypsin/EDTA. The radioactivity remaining in the cell pellet represented internalized TC-Cbl.

Binding and Internalization of Anti-TCblR Antibody by Cell Surface TCblR

Fluorescent Qdot tagged monoclonal antibody 1-19 complex provided visualization of GFP tagged receptor dynamics in the cell. Internalization of antibody complex, representing TCblR mediated uptake, was time and temperature dependent. The fluorescent tag appeared to be uniformly dispersed throughout the cell surface at 4° C. At 37° C., the fluorescent tag appeared to segregate to specific regions with the fluorescence appearing more pronounced due to coalescing of the antibody tagged receptors within these regions. With time, the fluorescence appeared to diffuse and dissipate in the first 60 min but by 180 min, the nanoparticles appeared to segregate in the cytoplasm (data not shown).

Identifying the Regions Involved in TC-Cbl Binding

Figure 27A:
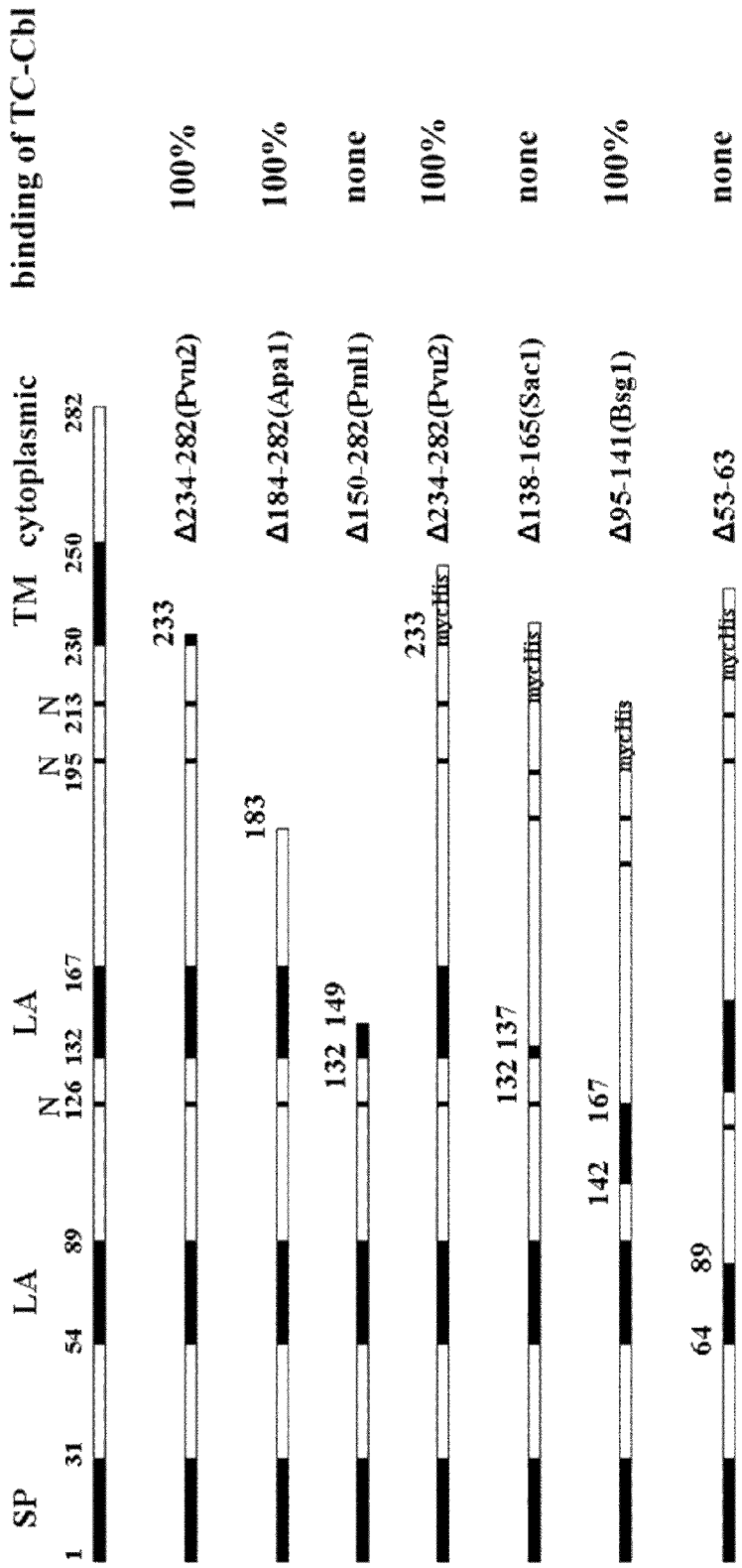

The secreted form of TCblR lacking the transmembrane and cytoplasmic domains binds TC-Cbl with the same affinity as native full-length receptor (Quadros et al., (2009) *Blood* 113, 186-192). Testing the various deletion constructs with or without a Myc-His tag, generated from the 233 aa secreted form of the receptor provided information on the regions of the protein involved in ligand binding (FIG. 27A). Deleting the C-terminal 49 aa that includes the two N-glycosylation sites had no effect on TC-Cbl binding. However, deleting part of the second LDLR-A domain along with the remaining C-terminal residues (aa 150-233) resulted in complete loss of ligand binding. Retaining all of the C-terminal residues and deleting only the N-terminal 11 residues (aa 53-63) of the first LDLR-A domain also resulted in complete loss of ligand binding.

Identifying Amino Acids Critical for TC-Cbl Binding

The specificity of TC-Cbl for the two LDLR-A domains with the consensus sequence for $Ca^{++}$ binding in the C-terminus of these domains and the absolute requirement of $Ca^{++}$ for TCblR/TC-Cbl interaction (Quadros et al., (2009) *Blood* 113, 186-192 and Quadros et al., (2005) *Biochem Biophys Res Commun* 327, 1006-1010), suggested the involvement of amino acids within these domains in the specificity for ligand binding and therefore the effect of mutating specific amino acids in this region, on TC-Cbl binding was tested. HEK293 cells were transfected with the mutated constructs to produce mutated receptor proteins. The receptor expression was confirmed by ELISA assay as previously described (Jiang et al., (2011) *Drug Deliv* 18, 74-78). In order to determine if these amino acids are critical for maintaining the module conformation necessary for ligand binding, we performed site-directed mutagenesis of amino acids D85 and E86 in the first LDLR-A domain and D163 and E164 in the second LDLR-A domain separately. Mutated receptors were tested for TC-Cbl binding by the assay described in methods section. The results showed that mutating the two amino acids in either of the LDLR domains, completely abolished TC-Cbl binding (FIG. 27B).

Figure 28:
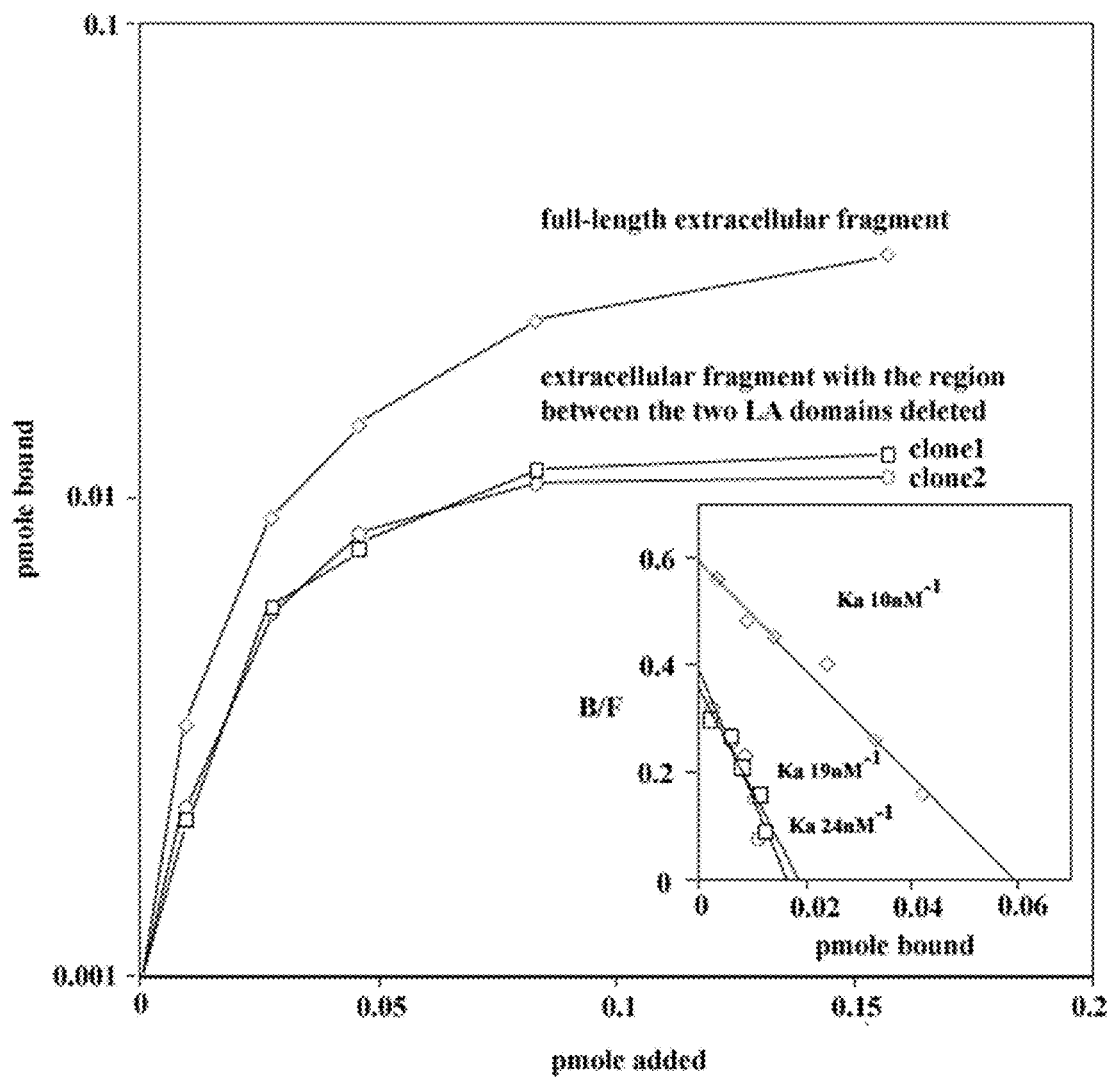
FIG. 28 is a line graph that shows the Kinetics of TC[$^{57}$Co] Cbl binding to the extracellular secreted form of TCblR with (-◇-) and without the CUB domain (-■-; -●-). Deleting the 55 amino acid CUB domain separating the two LDLR domains does not appear to drastically alter TC-Cbl binding as shown for the protein from two clones isolated by selecting for stable expression. Inset shows Scatchard analysis of the binding data.

Binding of TC-[$^{57}$Co]Cbl to the secreted form of recombinant TCblR with the cysteine rich 37 aa (95 to 131) region between the two LDLR-A domains deleted, showed little or no change in ligand binding with a Ka value that was similar to the full length receptor (FIG. 28).

Identifying Structural Domains Involved in TC-Cbl Uptake

Figure 29A:
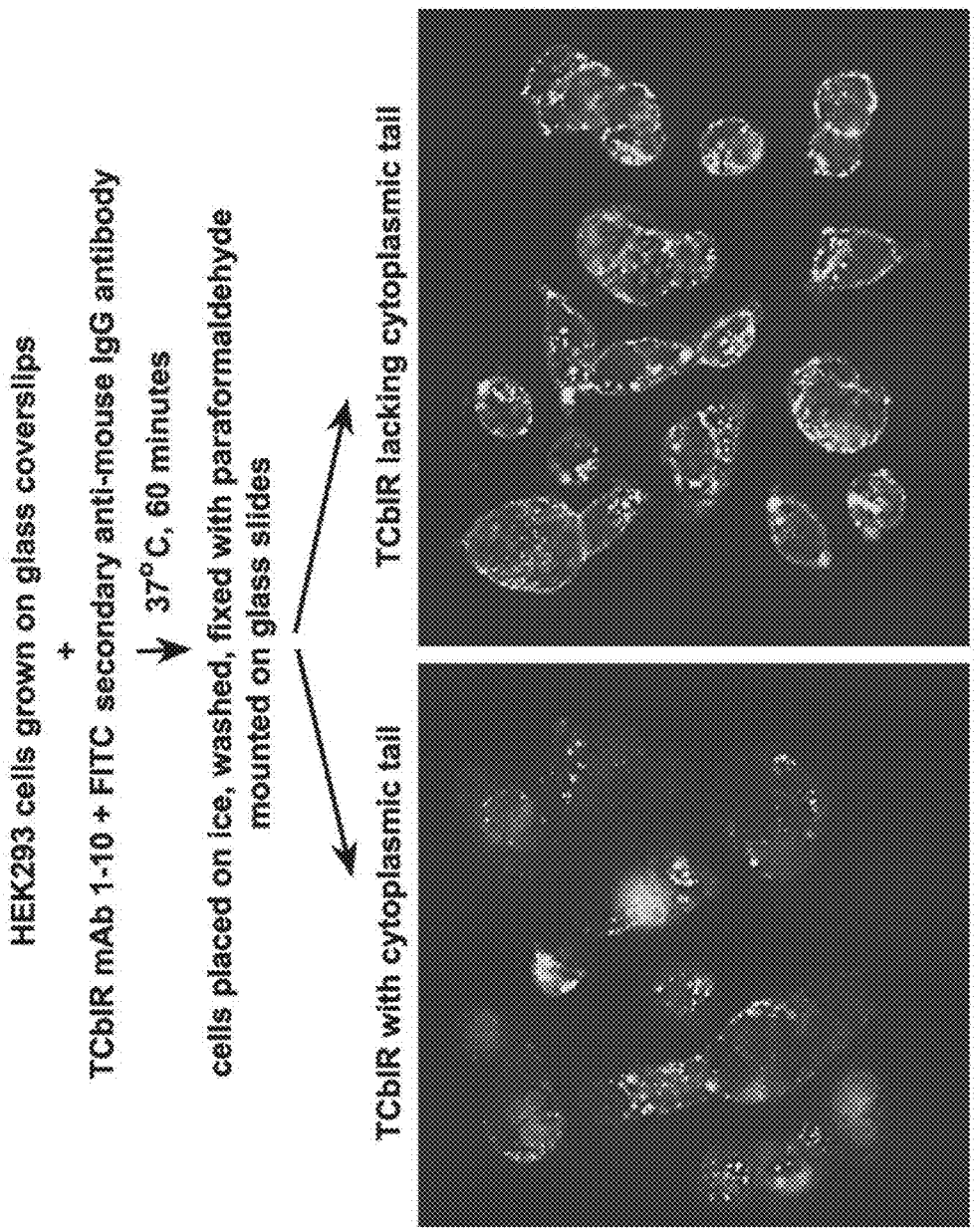
FIG. 29A is a micrograph that shows TC-Cbl uptake in cells engineered to express TCblR with the cytoplasmic tail deleted.
Figure 29B:
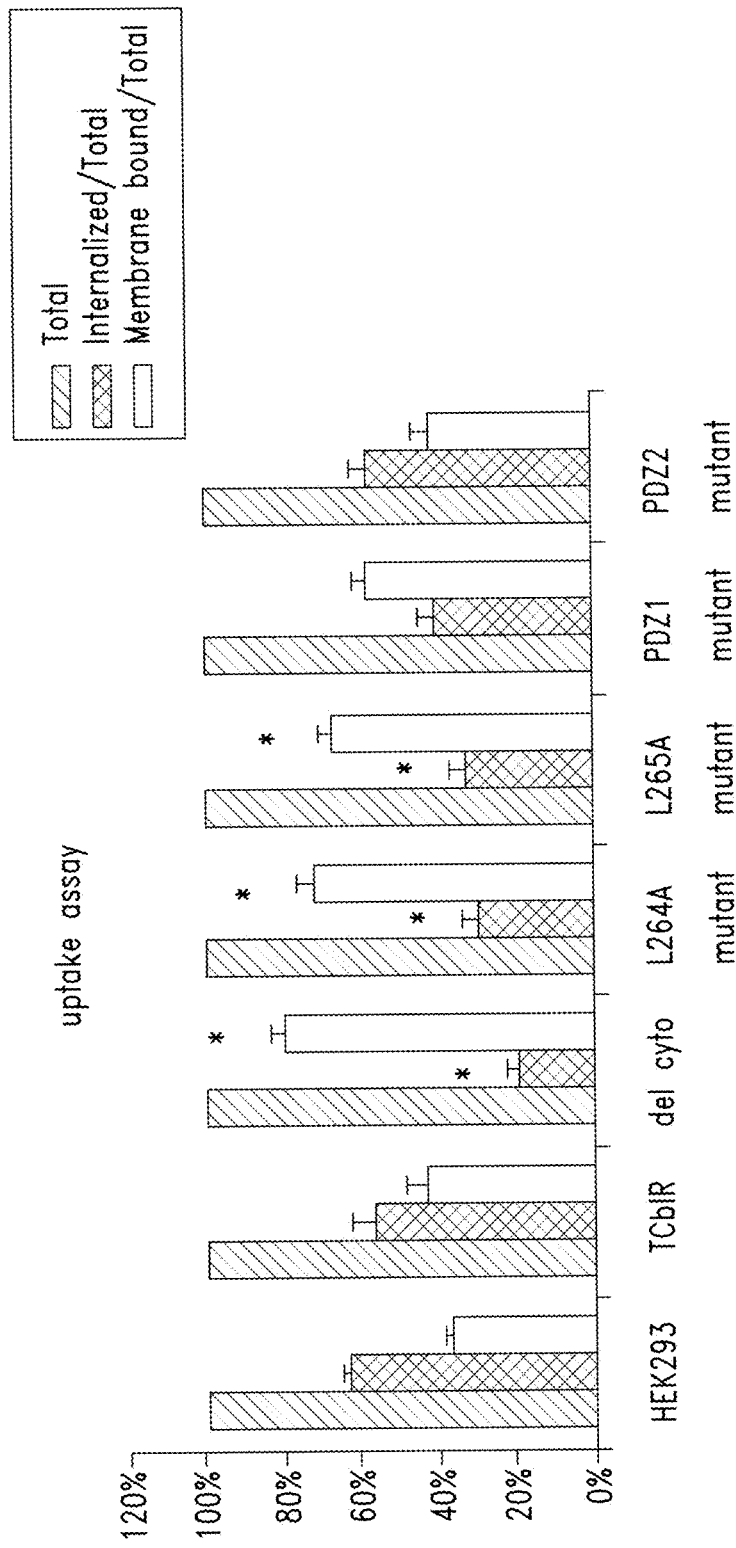
FIG. 29B is a bar graph that shows binding and internalization of TC-Cbl by membrane expressed TCblR with deletion or specific mutations in the 32 amino acid cytoplasmic domain of TCblR. Deletion of the 32 amino acid cytoplasmic tail has no effect on binding but internalization of TC-Cbl is severely compromised. Mutating L264, L265 or PDZ1 domain likewise affected internalization while mutating PDZ2 had no effect.

The binding of TC-Cbl by the secreted form of TCblR in which the transmembrane and cytoplasmic domains were deleted indicated that all of the structural determinants for TC-Cbl binding were present in the extracellular domain and that the cytoplasmic tail may play a role in the internalization of the membrane anchored TCblR along with its ligand, TC-Cbl. Deleting the cytoplasmic tail resulted in expression of a membrane-anchored receptor that bound TC-Cbl, but could not internalize the complex. The TCblR with the cytoplasmic tail expressed in HEK 293 cells, efficiently internalized anti TCblR antibody tagged with FITC-secondary antibody as indicated by segregation, diffusion and ultimately loss of fluorescence. The cells expressing TCblR without the cytoplasmic tail showed most of the flouresence on the cell surface indicating lack of internalization (FIG. 29A). Quantitative determination of binding and internalization of TC-[$^{57}$Co]Cbl in normal and TCblR overexpressing HEK 293 cells incubated at 37° C. for 1 hour, showed about 37-43% of the radiolabel on the membrane while 57-63% was internalized. In contrast, HEK293 cells expressing TCblR with the cytoplasmic tail deleted failed to internalize the TC-[$^{57}$Co]Cbl as indicated by 80% of the TCblR-bound radiolabel remaining on the cell surface (FIG. 29B). A similar decrease was observed when specific amino acids (L264A and L265A) within the cytoplasmic tail were mutated. Mutating each of the PDZ domains within this region also decreased internalization, albeit to a lesser degree (FIG. 29B).

Identifying Cytoplasmic Sequences Involved in Internalization of TC-Cbl

To further characterize the specific amino acids involved in internalization of TC-Cbl, potential functional sites were identified in the cytoplasmic region using ELM software (The Eukaryotic Linear Motif resource for functional sites in protein); namely PDZ domain binding motif, QERL (AA256-259) [SEQ ID NO:59] and KESL (AA269-272) [SEQ ID NO:60] and a dileucine-based signal sequence RPLGLL (AA260-265) [SEQ ID NO:61]. To test if they are functional signal sequences, four stable HEK293 cell lines were generated that over express four mutated TCblR, namely QAAA (PDZ1) [SEQ ID NO:62], KAAA (PDZ2) [SEQ ID NO:63], RPLGAL (L264A) [SEQ ID NO:64], and RPLGLA (L265A) [SEQ ID NO:65]. Uptake of TC-[$^{57}$Co]Cbl by the four stable cell lines expressing the mutated proteins showed significantly decreased uptake in cells expressing the RPLGLL (SEQ ID NO:61) and the PDZ mutations (FIG. 29B).

In summary, the membrane anchor and the cytoplasmic domains as well as the N-glycosylation sites in the extracellular domain of TCblR are not necessary for TC-Cbl binding. Deleting the cysteine-rich region separating the two LDLR-A domains does not affect TC-Cbl binding. The two LDLR-A domains with the negatively charged acidic residues involved in Ca++ binding are critical determinants of ligand binding. The cytoplasmic tail appears to be critical for internalizing the ligand. Within this region, the RPLGLL motif and the PDZ binding domains appear to be involved in initiating and completing the process of ligand internalization.

According to the methods described herein, anti-TCblR antibodies specific for the functional domains and amino acids critical for TC-Cbl binding and cellular uptake can be used to treat hyperproliferative diseases and disorders. For example, the regions critical for TC-Cbl binding may be targeted when generating blocking antibodies. In particular, anti-TCblR antibodies that block the binding of TC-Cbl to TCblR, and thereby interfering with cellular uptake of cobalamin, will recognize an epitope at or near one of the two LDLR-A domains. In particular, a blocking antibody may recognize the region including amino acid residues 54-89 or 132-167. Within these LDLR-A domains, it has been demonstrated that amino acid residues 53-63, 85-86, 150-167 and 163-164 are involved in TC-Cbl binding to TCblR.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An isolated antibody, or an antigen-binding fragment thereof, that binds to human transcobalamin receptor (TCblR), wherein said antibody or fragment thereof comprises: (i) a VH region comprising VHCDR1, VHCDR2 and VHCDR3 amino acid sequences set forth in SEQ ID NOs:38, 39 and 40, respectively, and (ii) a VL region comprising VLCDR1, VLCDR2 and VLCDR3 amino acid sequences set forth in SEQ ID NOs:46, 47 and 48, respectively.

2. The isolated antibody, or antigen-binding fragment thereof, according to claim 1, wherein the VH region comprises the amino acid sequence set forth in SEQ ID NO:37 or the VL region comprises the amino acid sequence set forth in SEQ ID NO:45.

3. An isolated antibody, or antigen-binding fragment thereof, that binds to human transcobalamin receptor (TCblR), wherein said antibody or fragment thereof comprises a VH region comprising the amino acid sequence set forth in SEQ ID NO:37 and a VL region.

4. An isolated antibody, or an antigen-binding fragment thereof, that binds to human transcobalamin receptor (TCblR), wherein said antibody or fragment thereof comprises a VL region comprising the amino acid sequence set forth in SEQ ID NO:45 and a VH region.

5. The isolated antibody or antigen-binding fragment thereof, according to claim 1, wherein the antibody is humanized.

6. The isolated antibody or antigen-binding fragment thereof, according to claim 1, wherein the antibody is monoclonal.

7. The isolated antibody, or antigen-binding fragment thereof, according to claim 1, wherein the antibody is conjugated to an agent selected from the group consisting of a chemotherapeutic, a drug, a toxin and an imaging compound.

8. The isolated antibody, or antigen-binding fragment thereof, according to claim 1, wherein the antibody inhibits cobalamin (Cbl) from binding TCblR.

9. A composition comprising a physiologically acceptable carrier and a therapeutically effective amount of the isolated antibody, or antigen-binding fragment thereof, according to claim 1.

10. A kit comprising the composition of claim 9.

11. The isolated antibody, or antigen-binding fragment thereof, according to claim 3, wherein the antibody is humanized.

12. The isolated antibody, or antigen-binding fragment thereof, according to claim 3, wherein the antibody is monoclonal.

13. The isolated antibody, or antigen-binding fragment thereof, according to claim 3, wherein the antibody is conjugated to an agent selected from the group consisting of a chemotherapeutic, a drug, a toxin and an imaging compound.

14. The isolated antibody, or antigen-binding fragment thereof, according to claim 4, wherein the antibody is humanized.

15. The isolated antibody, or antigen-binding fragment thereof, according to claim 4, wherein the antibody is monoclonal.

16. The isolated antibody, or antigen-binding fragment thereof, according to claim 4, wherein the antibody is conjugated to an agent selected from the group consisting of a chemotherapeutic, a drug, a toxin and an imaging compound.

17. The isolated antibody, or antigen-binding fragment thereof, according to claim 2, wherein the VH region comprises the amino acid sequence set forth in SEQ ID NO:37 and the VL region comprises the amino acid sequence set forth in SEQ ID NO:45.

* * * * *

SEQUENCE LISTING

```
<160> NUMBER OF SEQ ID NOS: 65

<210> SEQ ID NO 1
<211> LENGTH: 414
<212> TYPE: DNA
<213> ORGANISM: Mus musculus

<400> SEQUENCE: 1
atgagagtgc tgattccttt gtggctgttc acagcctttc ctggtatcct gtctgatgtg      60
cagcttcagg agtcgggacc tggcctggtg aaaccttctc agtctctgtc cctcacctgc     120
actgtccttg gctattcaat caccagtgat tatgcctgga actggatccg gcagtttcca     180
ggaaacaaac tggagtggat gggctacata agctttagtg gtaacattcg ttacaacccg     240
tctctcgaga gtcgaatctc tatcactcga gacacatcca agagccagtt cttcctgcag     300
ttgaattctg tgactactga ggacagaggc acatattact gtgcaagagc gggactggga     360
cgagtgttct actttgacta ctggggccaa ggcaccgctc tcacagtctc ctca          414

<210> SEQ ID NO 2
<211> LENGTH: 27
<212> TYPE: DNA
<213> ORGANISM: Mus musculus

<400> SEQUENCE: 2
ggctattcaa tcaccagtga ttatgcc                                         27

<210> SEQ ID NO 3
<211> LENGTH: 21
<212> TYPE: DNA
<213> ORGANISM: Mus musculus

<400> SEQUENCE: 3
ataagcttta gtggtaacat t                                               21

<210> SEQ ID NO 4
<211> LENGTH: 39
<212> TYPE: DNA
<213> ORGANISM: Mus musculus

<400> SEQUENCE: 4
gcaagagcgg gactgggacg agtgttctac tttgactac                            39

<210> SEQ ID NO 5
<211> LENGTH: 138
<212> TYPE: PRT
<213> ORGANISM: Mus musculus

<400> SEQUENCE: 5
```

```
Met Arg Val Leu Ile Pro Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Leu Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Phe Ser Gly Asn Ile Arg Tyr Asn Pro
65                  70                  75                  80

Ser Leu Glu Ser Arg Ile Ser Ile Thr Arg Asp Thr Ser Lys Ser Gln
                85                  90                  95

Phe Phe Leu Gln Leu Asn Ser Val Thr Thr Glu Asp Arg Gly Thr Tyr
            100                 105                 110

Tyr Cys Ala Arg Ala Gly Leu Gly Arg Val Phe Tyr Phe Asp Tyr Trp
        115                 120                 125

Gly Gln Gly Thr Ala Leu Thr Val Ser Ser
        130                 135

<210> SEQ ID NO 6
<211> LENGTH: 9
<212> TYPE: PRT
<213> ORGANISM: Mus musculus

<400> SEQUENCE: 6

Gly Tyr Ser Ile Thr Ser Asp Tyr Ala
1               5

<210> SEQ ID NO 7
<211> LENGTH: 7
<212> TYPE: PRT
<213> ORGANISM: Mus musculus

<400> SEQUENCE: 7

Ile Ser Phe Ser Gly Asn Ile
1               5

<210> SEQ ID NO 8
<211> LENGTH: 13
<212> TYPE: PRT
<213> ORGANISM: Mus musculus

<400> SEQUENCE: 8

Ala Arg Ala Gly Leu Gly Arg Val Phe Tyr Phe Asp Tyr
1               5                   10

<210> SEQ ID NO 9
<211> LENGTH: 399
<212> TYPE: DNA
<213> ORGANISM: Mus musculus

<400> SEQUENCE: 9
atggattcac aggcccaggt tcttatgtta ctgctgctat gggtatctgg tacctgtggg     60
gacattgtga tgtcacagtc tccatcctcc ctagctgtgt cagttggaga gaaggttact    120
atgagctgca agtccagtca gagccttttta tatagtagca atcaaaagaa ctacttggcc    180
tggtaccagc agaaaccagg gcagtctcct caactgttga ttttccgggc atccaccagg    240
gaatctgggg tccctgatcg cttcacaggc agtggatctg gacagattt cactctcacc    300
```

```
atcagcagtg tgaagcctga agacctggca gtttatttct gtcagcaata ttataactat    360
ccattcacgt tcggctcggg gacaacgttg gagataaaa                           399
```

<210> SEQ ID NO 10
<211> LENGTH: 36
<212> TYPE: DNA
<213> ORGANISM: Mus musculus

<400> SEQUENCE: 10

```
cagagccttt tatatagtag caatcaaaag aactac                              36
```

<210> SEQ ID NO 11
<211> LENGTH: 9
<212> TYPE: DNA
<213> ORGANISM: Mus musculus

<400> SEQUENCE: 11

```
cgggcatcc                                                             9
```

<210> SEQ ID NO 12
<211> LENGTH: 27
<212> TYPE: DNA
<213> ORGANISM: Mus musculus

<400> SEQUENCE: 12

```
cagcaatatt ataactatcc attcacg                                        27
```

<210> SEQ ID NO 13
<211> LENGTH: 133
<212> TYPE: PRT
<213> ORGANISM: Mus musculus

<400> SEQUENCE: 13

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Ser Pro Gln Leu Leu Ile Phe Arg Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Pro Glu Asp Leu Ala Val Tyr
            100                 105                 110

Phe Cys Gln Gln Tyr Tyr Asn Tyr Pro Phe Thr Phe Gly Ser Gly Thr
        115                 120                 125

Thr Leu Glu Ile Lys
    130

<210> SEQ ID NO 14
<211> LENGTH: 12
<212> TYPE: PRT
<213> ORGANISM: Mus musculus

<400> SEQUENCE: 14

Gln Ser Leu Leu Tyr Ser Ser Asn Gln Lys Asn Tyr
1               5                   10

<210> SEQ ID NO 15
<211> LENGTH: 3
<212> TYPE: PRT
<213> ORGANISM: Mus musculus

<400> SEQUENCE: 15

Arg Ala Ser
1

<210> SEQ ID NO 16
<211> LENGTH: 9
<212> TYPE: PRT
<213> ORGANISM: Mus musculus

<400> SEQUENCE: 16

Gln Gln Tyr Tyr Asn Tyr Pro Phe Thr
1               5

<210> SEQ ID NO 17
<211> LENGTH: 411
<212> TYPE: DNA
<213> ORGANISM: Mus musculus

<400> SEQUENCE: 17

```
atgagagtgc tgattctttt gtggctgttc aaagcctttc ctggtatcct gtctgatgtg      60
cagcttcagg agtcgggacc tggcctggtg aaaccttctc agtctctgtc cctcacctgc     120
actgtcactg gctactcaat caccagtgat tatgcctgga actggatccg gcagtttcct     180
ggaaacaaac tggagtggat gggctacata gcctacacta taggactttt ctacacccca     240
tctctcgaaa gtcgaatctc tatcactcgc gacacatcca agaaccagtt cttcctgcag     300
ttgaattctg tgactactga ggacacaggc acatattact gtgcacgaaa ctccggtaaa     360
acctacggct ttacttactg gggccaaggg actctagtca ctgtctctgc a              411
```

<210> SEQ ID NO 18
<211> LENGTH: 27
<212> TYPE: DNA
<213> ORGANISM: Mus musculus

<400> SEQUENCE: 18

```
ggctactcaa tcaccagtga ttatgcc                                           27
```

<210> SEQ ID NO 19
<211> LENGTH: 21
<212> TYPE: DNA
<213> ORGANISM: Mus musculus

<400> SEQUENCE: 19

```
atagcctaca ctaataggac t                                                 21
```

<210> SEQ ID NO 20
<211> LENGTH: 36
<212> TYPE: DNA
<213> ORGANISM: Mus musculus

<400> SEQUENCE: 20

```
gcacgaaact ccggtaaaac ctacggcttt acttac                                 36
```

<210> SEQ ID NO 21
<211> LENGTH: 137
<212> TYPE: PRT

<213> ORGANISM: Mus musculus

<400> SEQUENCE: 21

Met Arg Val Leu Ile Leu Leu Trp Leu Phe Lys Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ala Tyr Thr Asn Arg Thr Phe Tyr Thr Pro
65                  70                  75                  80

Ser Leu Glu Ser Arg Ile Ser Ile Thr Arg Asp Thr Ser Lys Asn Gln
                85                  90                  95

Phe Phe Leu Gln Leu Asn Ser Val Thr Thr Glu Asp Thr Gly Thr Tyr
            100                 105                 110

Tyr Cys Ala Arg Asn Ser Gly Lys Thr Tyr Gly Phe Thr Tyr Trp Gly
        115                 120                 125

Gln Gly Thr Leu Val Thr Val Ser Ala
    130                 135

<210> SEQ ID NO 22
<211> LENGTH: 9
<212> TYPE: PRT
<213> ORGANISM: Mus musculus

<400> SEQUENCE: 22

Gly Tyr Ser Ile Thr Ser Asp Tyr Ala
1               5

<210> SEQ ID NO 23
<211> LENGTH: 7
<212> TYPE: PRT
<213> ORGANISM: Mus musculus

<400> SEQUENCE: 23

Ile Ala Tyr Thr Asn Arg Thr
1               5

<210> SEQ ID NO 24
<211> LENGTH: 12
<212> TYPE: PRT
<213> ORGANISM: Mus musculus

<400> SEQUENCE: 24

Ala Arg Asn Ser Gly Lys Thr Tyr Gly Phe Thr Tyr
1               5                   10

<210> SEQ ID NO 25
<211> LENGTH: 399
<212> TYPE: DNA
<213> ORGANISM: Mus musculus

<400> SEQUENCE: 25
atggattcac aggcccaggt tcttatgtta ctgctgctat gggtatctgg tacctgtggg    60
gacattgtga tgtcacagtc tccatcctcc ctagttgtgt caattggaga gaaggttact   120
atgagctgca gtccagtca gcggcttttta tatagtgcca atcaaaagaa ctacttggcc   180
tggtaccagc agaaaccagg gcagtctcct aaactgctga tttactgggc atccactagg   240

```
gaatctgggg tccctgatcg cttcacaggc agtggatctg ggacagattt cactctcacc      300
atcagcagtg tgagggctga agacctggca ctttattact gtcagcaatt ttataactat      360
ccattaacgt tcggctcggg gacaaagttg gaaataaaa                             399
```

<210> SEQ ID NO 26
<211> LENGTH: 36
<212> TYPE: DNA
<213> ORGANISM: Mus musculus

<400> SEQUENCE: 26

```
cagcggcttt tatatagtgc aatcaaaag aactac                                 36
```

<210> SEQ ID NO 27
<211> LENGTH: 9
<212> TYPE: DNA
<213> ORGANISM: Mus musculus

<400> SEQUENCE: 27

```
tgggcatcc                                                              9
```

<210> SEQ ID NO 28
<211> LENGTH: 27
<212> TYPE: DNA
<213> ORGANISM: Mus musculus

<400> SEQUENCE: 28

```
cagcaatttt ataactatcc attaacg                                          27
```

<210> SEQ ID NO 29
<211> LENGTH: 133
<212> TYPE: PRT
<213> ORGANISM: Mus musculus

<400> SEQUENCE: 29

```
Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Val
            20                  25                  30

Val Ser Ile Gly Glu Lys Val Thr Met Ser Cys Lys Ser Ser Gln Arg
        35                  40                  45

Leu Leu Tyr Ser Ala Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Arg Ala Glu Asp Leu Ala Leu Tyr
            100                 105                 110

Tyr Cys Gln Gln Phe Tyr Asn Tyr Pro Leu Thr Phe Gly Ser Gly Thr
        115                 120                 125

Lys Leu Glu Ile Lys
    130
```

<210> SEQ ID NO 30
<211> LENGTH: 12
<212> TYPE: PRT
<213> ORGANISM: Mus musculus

<400> SEQUENCE: 30

Gln Arg Leu Leu Tyr Ser Ala Asn Gln Lys Asn Tyr
1               5                   10

<210> SEQ ID NO 31
<211> LENGTH: 3
<212> TYPE: PRT
<213> ORGANISM: Mus musculus

<400> SEQUENCE: 31

Trp Ala Ser
1

<210> SEQ ID NO 32
<211> LENGTH: 9
<212> TYPE: PRT
<213> ORGANISM: Mus musculus

<400> SEQUENCE: 32

Gln Gln Phe Tyr Asn Tyr Pro Leu Thr
1               5

<210> SEQ ID NO 33
<211> LENGTH: 411
<212> TYPE: DNA
<213> ORGANISM: Mus musculus

<400> SEQUENCE: 33

```
atgagagtgc tgattctttt gtgcctgttc acagcctttc ctggtatcct gtctgatgtg     60
cagcttcagg agtcaggacc tgacctggtg aaaccttctc agtcactttc gatcacctgc    120
actgtcactg gctactccat caccagtgat tatagctggc actggatccg gcagtttcca    180
ggaaacaaac tggaatggat gggctacata cactccagtg gtatcactaa ctacaaccca    240
tctctcaaaa gtcgaatctc tatcactcga gacacatcca agaaccagtt cttcctgcac    300
ttgagttcta tgactaatga ggacacagcc acatattact gtacaagacc tccggtagta    360
acccggtact cgatgtctg gggcgcaggg accacggtca ccgtctcctc a              411
```

<210> SEQ ID NO 34
<211> LENGTH: 27
<212> TYPE: DNA
<213> ORGANISM: Mus musculus

<400> SEQUENCE: 34
ggctactcca tcaccagtga ttatagc                                         27

<210> SEQ ID NO 35
<211> LENGTH: 21
<212> TYPE: DNA
<213> ORGANISM: Mus musculus

<400> SEQUENCE: 35
atacactcca gtggtatcac t                                               21

<210> SEQ ID NO 36
<211> LENGTH: 36
<212> TYPE: DNA
<213> ORGANISM: Mus musculus

<400> SEQUENCE: 36
acaagacctc cggtagtaac ccggtacttc gatgtc                               36

<210> SEQ ID NO 37
<211> LENGTH: 137
<212> TYPE: PRT
<213> ORGANISM: Mus musculus

<400> SEQUENCE: 37

Met Arg Val Leu Ile Leu Leu Cys Leu Phe Thr Ala Phe Pro Gly Ile
1               5                   10                  15

Leu Ser Asp Val Gln Leu Gln Glu Ser Gly Pro Asp Leu Val Lys Pro
            20                  25                  30

Ser Gln Ser Leu Ser Ile Thr Cys Thr Val Thr Gly Tyr Ser Ile Thr
        35                  40                  45

Ser Asp Tyr Ser Trp His Trp Ile Arg Gln Phe Pro Gly Asn Lys Leu
    50                  55                  60

Glu Trp Met Gly Tyr Ile His Ser Ser Gly Ile Thr Asn Tyr Asn Pro
65                  70                  75                  80

Ser Leu Lys Ser Arg Ile Ser Ile Thr Arg Asp Thr Ser Lys Asn Gln
                85                  90                  95

Phe Phe Leu His Leu Ser Ser Met Thr Asn Glu Asp Thr Ala Thr Tyr
            100                 105                 110

Tyr Cys Thr Arg Pro Pro Val Val Thr Arg Tyr Phe Asp Val Trp Gly
        115                 120                 125

Ala Gly Thr Thr Val Thr Val Ser Ser
    130                 135

<210> SEQ ID NO 38
<211> LENGTH: 9
<212> TYPE: PRT
<213> ORGANISM: Mus musculus

<400> SEQUENCE: 38

Gly Tyr Ser Ile Thr Ser Asp Tyr Ser
1               5

<210> SEQ ID NO 39
<211> LENGTH: 7
<212> TYPE: PRT
<213> ORGANISM: Mus musculus

<400> SEQUENCE: 39

Ile His Ser Ser Gly Ile Thr
1               5

<210> SEQ ID NO 40
<211> LENGTH: 12
<212> TYPE: PRT
<213> ORGANISM: Mus musculus

<400> SEQUENCE: 40

Thr Arg Pro Pro Val Val Thr Arg Tyr Phe Asp Val
1               5                   10

<210> SEQ ID NO 41
<211> LENGTH: 399
<212> TYPE: DNA
<213> ORGANISM: Mus musculus

<400> SEQUENCE: 41
atggaatcac agactcaggt cctcatgtcc ctgctgttct gggtatctgg tacctgtggg      60
gacattgtga tgacacagtc tccatcctcc ctgactgtga cagcaggaga gaaggtcact     120

```
atgagctgca agtccagtca gggtctgtta gacagtggaa atcaaaagaa ctacttgacc    180
tggtaccagc agaaaccagg gcagcctcct aaactgttga tctactgggc atccactagg    240
aaatctgggg tccctgatcg cttcacaggc agtggatctg gaacagattt cactctcacc    300
atcagcagtg tgcaggctga agacctggca gtttattact gtcagaatga ttatacttat    360
cctctcacgt tcggtgctgg gaccaagctg gagctgaaa                           399
```

<210> SEQ ID NO 42
<211> LENGTH: 36
<212> TYPE: DNA
<213> ORGANISM: Mus musculus

<400> SEQUENCE: 42

```
cagggtctgt tagacagtgg aaatcaaaag aactac                               36
```

<210> SEQ ID NO 43
<211> LENGTH: 9
<212> TYPE: DNA
<213> ORGANISM: Mus musculus

<400> SEQUENCE: 43

```
tgggcatcc                                                              9
```

<210> SEQ ID NO 44
<211> LENGTH: 27
<212> TYPE: DNA
<213> ORGANISM: Mus musculus

<400> SEQUENCE: 44

```
cagaatgatt atacttatcc tctcacg                                          27
```

<210> SEQ ID NO 45
<211> LENGTH: 133
<212> TYPE: PRT
<213> ORGANISM: Mus musculus

<400> SEQUENCE: 45

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Gly
        35                  40                  45

Leu Leu Asp Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Lys Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Thr Tyr Pro Leu Thr Phe Gly Ala Gly Thr
        115                 120                 125

Lys Leu Glu Leu Lys
    130

<210> SEQ ID NO 46
<211> LENGTH: 12
<212> TYPE: PRT

<213> ORGANISM: Mus musculus

<400> SEQUENCE: 46

Gln Gly Leu Leu Asp Ser Gly Asn Gln Lys Asn Tyr
1               5                   10

<210> SEQ ID NO 47
<211> LENGTH: 3
<212> TYPE: PRT
<213> ORGANISM: Mus musculus

<400> SEQUENCE: 47

Trp Ala Ser
1

<210> SEQ ID NO 48
<211> LENGTH: 9
<212> TYPE: PRT
<213> ORGANISM: Mus musculus

<400> SEQUENCE: 48

Gln Asn Asp Tyr Thr Tyr Pro Leu Thr
1               5

<210> SEQ ID NO 49
<211> LENGTH: 1283
<212> TYPE: DNA
<213> ORGANISM: Homo sapiens

<400> SEQUENCE: 49

```
gtgcgcgtgc gcagggataa agagcggtc tggacagcgc gtggccggcg ccgctgtggg        60
gacagcatga gcggcggttg gatggcgcag gttggagcgt ggcgaacagg ggctctgggc       120
ctggcgctgc tgctgctgct cggcctcgga ctaggcctgg aggccgccgc gagcccgctt       180
tccaccccga cctctgccca ggccgcaggc cccagctcag gctcgtgccc acccaccaag       240
ttccagtgcc gcaccagtgg cttatgcgtg ccccctcacct ggcgctgcga cagggacttg       300
gactgcagcg atggcagcga tgaggaggag tgcaggattg agccatgtac ccagaaaggg       360
caatgcccac cgcccctgg cctcccctgc ccctgcaccg cgtcagtga ctgctctggg       420
ggaactgaca agaaactgcg caactgcagc cgcctggcct gcctagcagg cgagctccgt       480
tgcacgctga gcgatgactg cattccactc acgtggcgct cgacggcca cccagactgt       540
cccgactcca gcgacgagct cggctgtgga accaatgaga tcctcccgga agggatgcc       600
acaaccatgg ggccccctgt gaccctggag agtgtcacct ctctcaggaa tgccacaacc       660
atggggcccc tgtgaccct ggagagtgtc cctctgtcg gaatgccac atcctcctct       720
gccggagacc agtctggaag cccaactgcc tatgggtta ttgcagctgc tgcggtgctc       780
agtgcaagcc tggtcaccgc caccctcctc cttttgtcct ggctccgagc ccaggagcgc       840
ctccgcccac tggggttact ggtggccatg aaggagtccc tgctgctgtc agaacagaag       900
acctcgctgc cctgaggaca agcacttgcc accaccgtca ctcagccctg ggcgtagccg       960
gacaggagga gagcagtgat gcggatgggt acccgggcac accagccctc agagacctga      1020
gctcttctgg ccacgtggaa cctcgaaccc gagctcctgc agaagtggcc ctggagattg      1080
agggtccctg gacactccct atggagatcc ggggagctag gatgggaac ctgccacagc      1140
cagaactgag gggctggccc caggcagctc cagggggta gaacggccct gtgcttaaga      1200
cactcctgct gccccgtctg agggtggcga ttaaagttgc ttcacatcct caaaaaaaaa      1260
```

```
aaaaaaaaaa aaaaaaaaaa aaa                                        1283

<210> SEQ ID NO 50
<211> LENGTH: 849
<212> TYPE: DNA
<213> ORGANISM: Homo sapiens

<400> SEQUENCE: 50
atgagcggcg gttggatggc gcaggttgga gcgtggcgaa caggggctct gggcctggcg     60
ctgctgctgc tgctcggcct cggactaggc ctggaggccg ccgcgagccc gctttccacc    120
ccgacctctg cccaggccgc aggccccagc tcaggctcgt gcccacccac caagttccag    180
tgccgcacca gtggcttatg cgtgcccctc acctggcgct gcgacaggga cttggactgc    240
agcgatggca gcgatgagga ggagtgcagg attgagccat gtacccagaa agggcaatgc    300
ccaccgcccc ctggcctccc ctgccctgc accggcgtca gtgactgctc tgggggaact    360
gacaagaaac tgcgcaactg cagccgcctg gcctgcctag caggcgagct ccgttgcacg    420
ctgagcgatg actgcattcc actcacgtgg cgctgcgacg ccacccaga ctgtcccgac    480 tccagcgacg agctcggctg tggaaccaat gagatcctcc cggaagggga tgccacaacc    540
atggggcccc tgtgaccct ggagagtgtc acctctctca ggaatgccac aaccatgggg    600 cccccctgtga ccctggagag tgtccctct gtcgggaatg ccacatcctc ctctgccgga    660
gaccagtctg gaagcccaac tgcctatggg gttattgcag ctgctgcggt gctcagtgca    720
agcctggtca ccgccaccct cctccttttg tcctggctcc gagcccagga gcgcctccgc    780
ccactggggt tactggtggc catgaaggag tccctgctgc tgtcagaaca gaagacctcg    840
ctgccttaa                                                            849

<210> SEQ ID NO 51
<211> LENGTH: 1254
<212> TYPE: DNA
<213> ORGANISM: Homo sapiens

<400> SEQUENCE: 51
ctggacagcg cgtggccggc gccgctgtgg ggacagcatg agcggcggtt ggatggcgca     60
ggttggagcg tggcgaacag gggctctggg cctggcgctg ctgctgctgc tcggcctcgg    120
actaggcctg gaggccgccg cgagcccgct ttccacccg acctctgccc aggccgcagg    180
ccccagctca ggctcgtgcc cacccaccaa gttccagtgc cgcaccagtg gcttatgcgt    240 gccccctcacc tggcgctgcg acagggactt ggactcagc gatggcagcg atgaggagga    300
gtgcaggatt gagccatgta cccagaaagg gcaatgccca ccgcccctg gcctcccctg    360 ccctgcacc ggcgtcagtg actgctctgg gggaactgac aagaaactgc gcaactgcag    420
ccgcctggcc tgcctagcag gcgagctccg ttgcacgctg agcgatgact gcattccact    480
cacgtggcgc tgcgacggcc acccagactg tcccgactcc agcgacgagc tcggctgtgg    540
aaccaatgag atcctcccgg aagggatgc cacaaccatg gggcccctg tgaccctgga    600 gagtgtcacc tctctcagga atgccacaac catggggccc cctgtgaccc tggagagtgt    660
cccctctgtc gggaatgcca catcctcctc tgccggagac cagtctggaa gcccaactgc    720
ctatggggtt attgcagctg ctgcggtgct cagtgcaagc ctggtcaccg ccaccctcct    780
ccttttgtcc tggctccgag cccaggagc cctccgccca ctggggttac tggtggccat    840
gaaggagtcc ctgctgctgt cagaacagaa gacctcgctg ccctgaggac aagcacttgc    900
caccaccgtc actcagccct gggcgtagcc ggacaggagg agagcagtga tgcggatggg    960
```

-continued

```
tacccgggca caccagccct cagagacctg agctcttctg gccacgtgga acctcgaacc    1020
cgagctcctg cagaagtggc cctggagatt gagggtccct ggacactccc tatggagatc    1080
cggggagcta ggatggggaa cctgccacag ccagaactga ggggctggcc ccaggcagct    1140
cccaggggt agaacggccc tgtgcttaag acactcctgc tgccccgtct gagggtggcg     1200
attaaagttg cttcacatcc tcaaaaaaaa aaaaaaaaaa aaaaaaaaaa aaaa           1254
```

<210> SEQ ID NO 52
<211> LENGTH: 1235
<212> TYPE: DNA
<213> ORGANISM: Homo sapiens

<400> SEQUENCE: 52

```
ggcgccgctg tggggacagc atgagcggcg gttggatggc gcaggttgga gcgtggcgaa      60
caggggctct gggcctggcg ctgctgctgc tgctcggcct cggactaggc ctggaggccg     120
ccgcgagccc gctttccacc ccgacctctg cccaggccgc aggccccagc tcaggctcgt     180
gcccacccac caagttccag tgccgcacca gtggcttatg cgtgcccctc acctggcgct     240
gcgacaggga cttggactgc agcgatggca gcgatgagga ggagtgcagg attgagccat     300
gtacccagaa agggcaatgc ccaccgcccc tggcctcccc ctgcccctgc accggcgtca     360
gtgactgctc tgggggaact gacaagaaac tgcgcaactg cagccgcctg gcctgcctag     420
caggcgagct ccgttgcacg ctgagcgatg actgcattcc actcacgtgg cgctgcgacg     480
gccacccaga ctgtcccgac tccagcgacg agctcggctg tggaaccaat gagatcctcc     540
cggaagggga tgccacaacc atggggcccc ctgtgaccct ggagagtgtc acctctctca     600
ggaatgccac aacctatggg cccctgtga ccctggagag tgtcccctct gtcgggaatg      660
ccacatcctc ctctgccgga gaccagtctg gaagcccaac tgcctatggg gttattgcag     720
ctgctgcggt gctcagtgca agcctggtca ccgccaccct cctccttttg tcctggctcc     780
gagcccagga gcgcctccgc ccactggggt tactggtggc catgaaggag tccctgctgc     840
tgtcagaaca aagacctcg ctgccctgag gacaagcact gccaccacc gtcactcagc       900
cctgggcgta gccggacagg aggagagcag tgatgcggat gggtacccgg gcacaccagc     960
cctcagagac ctgagctctt ctggccacgt ggaacctcga acccgagctc ctgcagaagt    1020
ggccctggag attgagggtc cctggacact ccctatggag atccggggag ctaggatggg    1080
gaacctgcca cagccagaac tgagggctg ccccaggca gctcccaggg ggtagaacgg      1140
ccctgtgctt aagacactcc tgctgccccg tctgagggtg gcgattaaag ttgcttcaca    1200
tccttaaaaa aaaaaaaaaa aaaaaaaaaa aaaaa                                1235
```

<210> SEQ ID NO 53
<211> LENGTH: 282
<212> TYPE: PRT
<213> ORGANISM: Homo sapiens

<400> SEQUENCE: 53

```
Met Ser Gly Gly Trp Met Ala Gln Val Gly Ala Trp Arg Thr Gly Ala
 1               5                  10                  15

Leu Gly Leu Ala Leu Leu Leu Leu Gly Leu Gly Leu Gly Leu Glu
                20                  25                  30

Ala Ala Ala Ser Pro Leu Ser Thr Pro Thr Ser Ala Gln Ala Ala Gly
            35                  40                  45

Pro Ser Ser Gly Ser Cys Pro Thr Lys Phe Gln Cys Arg Thr Ser
```

```
                50                  55                  60
Gly Leu Cys Val Pro Leu Thr Trp Arg Cys Asp Arg Asp Leu Asp Cys
 65                  70                  75                  80

Ser Asp Gly Ser Asp Glu Glu Cys Arg Ile Glu Pro Cys Thr Gln
                 85                  90                  95

Lys Gly Gln Cys Pro Pro Pro Gly Leu Pro Cys Pro Cys Thr Gly
                100                 105                 110

Val Ser Asp Cys Ser Gly Gly Thr Asp Lys Lys Leu Arg Asn Cys Ser
                115                 120                 125

Arg Leu Ala Cys Leu Ala Gly Glu Leu Arg Cys Thr Leu Ser Asp Asp
                130                 135                 140

Cys Ile Pro Leu Thr Trp Arg Cys Asp Gly His Pro Asp Cys Pro Asp
145                 150                 155                 160

Ser Ser Asp Glu Leu Gly Cys Gly Thr Asn Glu Ile Leu Pro Glu Gly
                165                 170                 175

Asp Ala Thr Thr Met Gly Pro Pro Val Thr Leu Glu Ser Val Thr Ser
                180                 185                 190

Leu Arg Asn Ala Thr Thr Met Gly Pro Pro Val Thr Leu Glu Ser Val
                195                 200                 205

Pro Ser Val Gly Asn Ala Thr Ser Ser Ser Ala Gly Asp Gln Ser Gly
                210                 215                 220

Ser Pro Thr Ala Tyr Gly Val Ile Ala Ala Ala Val Leu Ser Ala
225                 230                 235                 240

Ser Leu Val Thr Ala Thr Leu Leu Leu Ser Trp Leu Arg Ala Gln
                245                 250                 255

Glu Arg Leu Arg Pro Leu Gly Leu Leu Val Ala Met Lys Glu Ser Leu
                260                 265                 270

Leu Leu Ser Glu Gln Lys Thr Ser Leu Pro
                275                 280

<210> SEQ ID NO 54
<211> LENGTH: 14
<212> TYPE: PRT
<213> ORGANISM: Artificial Sequence
<220> FEATURE:
<223> OTHER INFORMATION: Peptide spacer

<400> SEQUENCE: 54

Glu Gly Lys Ser Ser Gly Ser Gly Ser Glu Ser Lys Val Asp
1               5                   10

<210> SEQ ID NO 55
<211> LENGTH: 18
<212> TYPE: PRT
<213> ORGANISM: Artificial Sequence
<220> FEATURE:
<223> OTHER INFORMATION: Peptide spacer

<400> SEQUENCE: 55

Lys Glu Ser Gly Ser Val Ser Ser Glu Gln Leu Ala Gln Phe Arg Ser
1               5                   10                  15

Leu Asp

<210> SEQ ID NO 56
<211> LENGTH: 5
<212> TYPE: PRT
<213> ORGANISM: Artificial Sequence
<220> FEATURE:
<223> OTHER INFORMATION: Flexible polylinke
```

<400> SEQUENCE: 56

Gly Gly Gly Gly Ser
1               5

<210> SEQ ID NO 57
<211> LENGTH: 25
<212> TYPE: DNA
<213> ORGANISM: Homo sapiens

<400> SEQUENCE: 57
aaaagaattc ctggacagcg cgtgg                                         25

<210> SEQ ID NO 58
<211> LENGTH: 27
<212> TYPE: DNA
<213> ORGANISM: Homo sapiens

<400> SEQUENCE: 58
aaaagcggcc gcgagccagg acaaaag                                       27

<210> SEQ ID NO 59
<211> LENGTH: 4
<212> TYPE: PRT
<213> ORGANISM: Homo sapiens

<400> SEQUENCE: 59

Gln Glu Arg Leu
1

<210> SEQ ID NO 60
<211> LENGTH: 4
<212> TYPE: PRT
<213> ORGANISM: Homo sapiens

<400> SEQUENCE: 60

Lys Glu Ser Leu
1

<210> SEQ ID NO 61
<211> LENGTH: 6
<212> TYPE: PRT
<213> ORGANISM: Homo sapiens

<400> SEQUENCE: 61

Arg Pro Leu Gly Leu Leu
1               5

<210> SEQ ID NO 62
<211> LENGTH: 4
<212> TYPE: PRT
<213> ORGANISM: Artificial Sequence
<220> FEATURE:
<223> OTHER INFORMATION: Mutated TC-Cbl internalization functional sites

<400> SEQUENCE: 62

Gln Ala Ala Ala
1

<210> SEQ ID NO 63
<211> LENGTH: 4
<212> TYPE: PRT
<213> ORGANISM: Artificial Sequence
<220> FEATURE:
<223> OTHER INFORMATION: Mutated TC-Cbl internalization functional sites

```
<400> SEQUENCE: 63

Lys Ala Ala Ala
1

<210> SEQ ID NO 64
<211> LENGTH: 6
<212> TYPE: PRT
<213> ORGANISM: Artificial Sequence
<220> FEATURE:
<223> OTHER INFORMATION: Mutated TC-Cbl internalization functional sites

<400> SEQUENCE: 64

Arg Pro Leu Gly Ala Leu
1               5

<210> SEQ ID NO 65
<211> LENGTH: 6
<212> TYPE: PRT
<213> ORGANISM: Artificial Sequence
<220> FEATURE:
<223> OTHER INFORMATION: Mutated TC-Cbl internalization functional sites

<400> SEQUENCE: 65

Arg Pro Leu Gly Leu Ala
1               5
```